(12) United States Patent
Grindrod et al.

(10) Patent No.: US 10,745,352 B2
(45) Date of Patent: *Aug. 18, 2020

(54) DUAL FUNCTION MOLECULES FOR HISTONE DEACETYLASE INHIBITION AND ATAXIA TELANGIECTASIA MUTATED ACTIVATION AND METHODS OF USE THEREOF

(71) Applicant: Shuttle Pharmaceuticals, Inc., Rockville, MD (US)

(72) Inventors: Scott Grindrod, Rockville, MD (US); Mira Jung, Rockville, MD (US); Milton Brown, Rockville, MD (US); Anatoly Dritschilo, Rockville, MD (US)

(73) Assignee: Shuttle Pharmaceuticals, Inc., Rockville, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/555,386

(22) PCT Filed: Mar. 3, 2016

(86) PCT No.: PCT/US2016/020573
§ 371 (c)(1),
(2) Date: Sep. 1, 2017

(87) PCT Pub. No.: WO2016/141122
PCT Pub. Date: Sep. 9, 2016

(65) Prior Publication Data
US 2018/0044292 A1     Feb. 15, 2018

Related U.S. Application Data

(63) Continuation of application No. 14/636,736, filed on Mar. 3, 2015, now Pat. No. 9,809,539.

(51) Int. Cl.
| | | |
|---|---|---|
| C07D 403/14 | (2006.01) |
| A61K 31/404 | (2006.01) |
| C07D 209/42 | (2006.01) |
| A61K 31/573 | (2006.01) |
| A61K 45/06 | (2006.01) |
| A61N 5/00 | (2006.01) |
| C07D 209/20 | (2006.01) |
| A61N 5/10 | (2006.01) |

(52) U.S. Cl.
CPC .......... *C07D 209/42* (2013.01); *A61K 31/404* (2013.01); *A61K 31/573* (2013.01); *A61K 45/06* (2013.01); *A61N 5/00* (2013.01); *C07D 209/20* (2013.01); *C07D 403/14* (2013.01); *A61K 2300/00* (2013.01); *A61N 2005/1098* (2013.01)

(58) Field of Classification Search
None
See application file for complete search history.

(56) References Cited

U.S. PATENT DOCUMENTS

| 2005/0014839 A1 | 1/2005 | Kozikowski et al. |
| 2005/0032831 A1 | 2/2005 | Kozikowski et al. |

FOREIGN PATENT DOCUMENTS

| WO | 2008117935 A1 | 10/2008 |
| WO | 2014090398 A1 | 6/2014 |
| WO | 2014178606 A1 | 11/2014 |

OTHER PUBLICATIONS

STN Registry entry for CAS RN 1026059-94-8; entered STN Registry database Jun. 6, 2008, Accessed Sep. 17, 2018.*
Lin et al., Zhongguo Yaoke Daxue Xuebao, 35 (2), 2004, pp. 106-109.*
International Search Report for PCT/US16/20573 dated May 20, 2016.

* cited by examiner

*Primary Examiner* — Alicia L Otton
(74) *Attorney, Agent, or Firm* — Morgan, Lewis & Bockius LLP

(57) ABSTRACT

Dual function compounds are provided that may be inhibitors of histone deacetylase (HDAC) and activators of ataxia telangiectasia mutated (ATM). Pharmaceutical compositions and methods of use are also provided that utilize such compounds.

4 Claims, 20 Drawing Sheets

SP-1-161

SP-1-163

SP-1-169-RACEMIC

SP-1-171-RACEMIC

SP-1-229

A102

A103

A104

SP-1-303

SP-1-161

SP-1-163

SP-1-169

SP-1-171

SP-1-229

A102

A103

A104

SP-1-303

| Compound/time | Fold Change in p-ATM |
|---|---|
| Untreated | 0.000 |
| KU55399 [10 µM] 1hr | -0.064 |
| DMSO | 0.071 |
| IR [6 Gy] 30 min | 1.057 |
| SP-1-105 [1 µM] 30 min | 0.656 |
| SP-1-105 [1 µM] 1hr | 0.408 |
| SP-1-105 [1 µM] 2hrs | 0.165 |
| SP-1-105 [1 µM] 4hrs | 0.121 |
| SP-1-105 [1 µM] 6hrs | 0.265 |

| Compound/time | Fold Change in p-ATM |
|---|---|
| Untreated | 0.000 |
| KU55399 [10 µM] 1hr | -0.105 |
| DMSO | 0.205 |
| IR [6 Gy] 30 min | 1.287 |
| DIM [0.5 µM] 30 min | 1.063 |
| SP-1-161 [1µM] 30 min | 0.742 |
| SP-1-161 [1µM] 1hr | 1.098 |
| SP-1-161 [1µM] 2hrs | 1.259 |
| SP-1-161 [1µM] 4hrs | 1.303 |
| SP-1-161 [1µM] 6hrs | 0.698 |

| Compound | Fold Change in p-ATM |
|---|---|
| Untreated | 0.000 |
| KU55399 [10 μM] 1 Hr. | -0.105 |
| DMSO | 0.205 |
| IR [6 Gy] 30 min | 1.287 |
| DIM [0.5 μM] 30 min | 1.063 |
| SP-1-163 [1μM] 30 min | 1.128 |
| SP-1-163 [1μM] 1hr | 1.283 |
| SP-1-163 [1μM] 2hrs | 1.328 |
| SP-1-163 [1μM] 4hrs | 1.269 |
| SP-1-163 [1μM] 6hrs | 0.952 |

| Compound/time | Fold Change in p-ATM |
|---|---|
| Untreated | 0.000 |
| KU55399 [10 µM] 1hr | -0.150 |
| DMSO | 0.051 |
| IR [6 Gy] 30 min | 1.320 |
| DIM [0.5 µM] 30 min | 1.224 |
| SP-1-169 [1µM] 30 min | 0.623 |
| SP-1-169 [1µM] 1hr | 0.820 |
| SP-1-169 [1µM] 2hrs | 0.929 |
| SP-1-169 [1µM] 4hrs | 1.173 |
| SP-1-169 [1µM] 6hrs | 0.654 |

| Cell Line | Compound | MTT Cytotoxicity Assay | Clonogenic Cytotoxicity Assay |
|---|---|---|---|
| | | $IC_{50}$ [μM] | $IC_{50}$ [μM] |
| 184A1 | SP-1-161 | 0.416 | 0.276 |
| | SP-1-163 | 0.506 | 0.259 |
| | SP-1-169 | 5.281 | 1.807 |
| | Sp-1-171 | 5.783 | 0.859 |
| MCF7 | SP-1-161 | 5.508 | 0.771 |
| | SP-1-163 | 24.050 | 0.879 |
| | SP-1-169 | 39.660 | 9.851 |
| | Sp-1-171 | 6.411 | 1.248 |

Fig. 9

| Compound | 184A1 | | | MCF7 | | |
|---|---|---|---|---|---|---|
| | D0 | α | β | D0 | α | β |
| DMSO [0.1 %] | 1.01 | 0.21 | 0.08 | 1.61 | 0.25 | 0.03 |
| DIM [0.3 µM] | 1.14 | 0.053 | 0.065 | 1.30 | 0.49 | 0.03 |
| SP-1-161 | 1.36 [0.2 µM] | 0.18 | 0.05 | 1.12 [0.7 µM] | 0.42 | 0.05 |

Fig. 10

| | | MTT IC$_{50}$ [μM] | | | |
|---|---|---|---|---|---|
| Origin | Cell line | SP-1-161 | SP-1-229 | SP-1-303 | SAHA |
| Breast | | | | | |
| NBE | MCF10A | 1.68 | 33.64 | 5.26 | 4.32 |
| BC | MCF7 | 4.55 | 4.51 | 0.15 | 3.62 |
| Prostate | | | | | |
| NPE | RWPE1 | 57.89 | 105.7 | 14.71 | |
| adenocar | PC3 | 3.79 | 1.37 | 0.38 | 1.06 |
| Cervix | | | | | |
| epidermoid cervixcarc | CasKi | 1.99 | 9.15 | 5.73 | 1.95 |
| H&N | | | | | |
| RR Squamous Carcinoma | SQ20B | 4.9 | 25.96 | 7.64 | 2.41 |

Fig. 13

DUAL FUNCTION MOLECULES FOR HISTONE DEACETYLASE INHIBITION AND ATAXIA TELANGIECTASIA MUTATED ACTIVATION AND METHODS OF USE THEREOF

CROSS-REFERENCE TO RELATED APPLICATIONS

The present application is a U.S. National Stage Application based on International Application No. PCT/US2016/020573, filed Mar. 3, 2016, which claims the benefit of priority to U.S. Non-Provisional application Ser. No. 14/636,736, filed Mar. 3, 2015, the entirety of which are incorporated herein by reference.

FIELD OF THE INVENTION

The present invention relates generally to compounds that inhibit histone deacetylase (HDAC) and activate ataxia telangiectasia mutated (ATM) and more particularly, but not exclusively, to dual function compounds that may inhibit HDAC and activate ATM and pharmaceutical compositions and methods of treating diseases that may beneficially utilize such compounds.

BACKGROUND OF THE INVENTION

A variety of diseases are known in the field to elude common treatment methods. For example, certain diseases and disorders that implicate the histone deacetylase (HDAC) proteins have continued to evade known therapeutics and treatment methodologies.

Accordingly, a need exists in the field for compounds, compositions, and methods for treating such elusive diseases and disorders, including certain cancers and neurological disorders.

SUMMARY OF THE INVENTION

The present invention meets the needs in the field by providing dual function compounds that may inhibit HDAC and activate ATM and may be used in the treatment of certain cancers, neurological disorders, and immunological disorders. Indeed, the compounds of the invention may be used in pharmaceutical compositions and methods of treatment in combating these and other related diseases.

In a first aspect, the invention includes a compound, such as a dual function, compound having the formula:

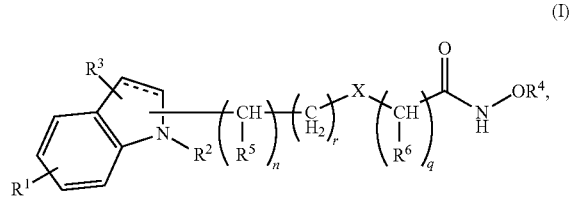

(I)

wherein $R^1$, $R^3$, $R^7$, and $R^8$ may be independently selected from the group consisting of H, hydroxy, halogen and, optionally substituted, alkyl, alkenyl, alkynyl, cycloalkyl, aryl, heterocycle, heteroaryl, amino, alkoxy, carboxy, carbalkoxy, carboxamido, sulfonyl, sulfinyl, monoalkylaminosulfinyl, dialkylaminosulfinyl, monoalkylaminosufonyl, dialkylaminosulfonyl, alkylsulfonylamino, hydroxysulfonyloxy, alkoxysulfonyloxy, alkylsulfonyloxy, hydroxysulfonyl, alkoxysulfonyl, alkylsulfonylalkyl, monoalkylaminosulfonylalkyl, dialkylaminosulfonylalkyl, monoalkylaminosulfinylalkyl, and dialkylaminosulfinylalkyl.

$R^2$ and $R^9$ may be independently selected from the group consisting of H and, optionally substituted, sulfinyl, sulfonyl, alkyl, alkenyl, cycloalkyl, aryl, heterocycle, and heteroaryl.

$R^4$ may be selected from the group consisting of H and optionally substituted alkyl.

$R^5$ may be selected from the group consisting of H, and optionally substituted alkyl and indole.

$R^6$ may be selected from the group consisting of H and optionally substituted alkyl.

X may be selected from the group consisting of:

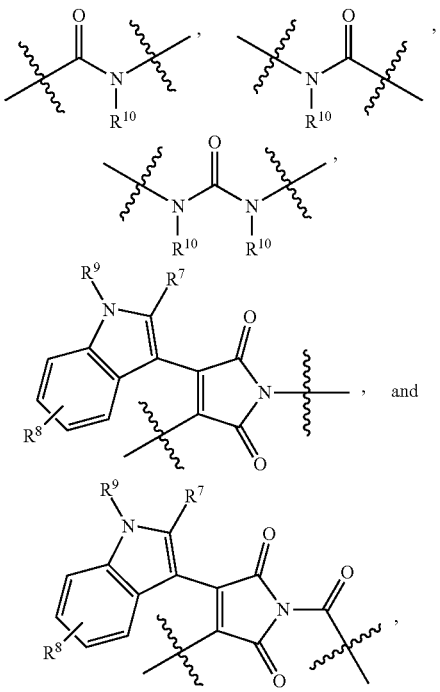

wherein $R^{10}$ may be selected from the group consisting of H and, optionally substituted, alkyl, alkenyl, cycloalkyl, aryl, heterocycle, and heteroaryl. In some aspects, when X is maleimide or N-carbonylmaleimide, n+r=0.

n may be 0 or 1; r may be an integer from 0 to 3; q may be an integer from 3 to 10; the dashed line may indicate the presence of a single bond or a double bond as allowed; with the proviso that, where X is a substituent other than maleimide or N-carbonylmaleimide and $R^5$ is a substituent other than indole, then $R^3$ is a substituent selected from the group consisting of hydroxy, halogen and, optionally substituted, alkyl, alkenyl, alkynyl, cycloalkyl, aryl, heterocycle, heteroaryl, amino, alkoxy, carboxy, carbalkoxy, carboxamido, sulfonyl, sulfinyl, monoalkylaminosulfinyl, dialkylaminosulfinyl, mono alkylaminosufonyl, dialkylaminosulfonyl, alkylsulfonylamino, hydroxysulfonyloxy, alkoxysulfonyloxy, alkylsulfonyloxy, hydroxysulfonyl, alkoxysulfonyl, alkylsulfonylalkyl, monoalkylaminosulfonylalkyl, dialkylaminosulfonylalkyl, mono alkylaminosulfinylalkyl, and dialkylaminosulfinylalkyl, with the dashed line indicating the presence of a double bond; and the pharmaceutically acceptable salts of the compound of Formula I.

In some embodiments, q may be an integer from 4 to 6. For example, q may be 5. Moreover, in certain embodiments of Formula I, where X is a substituent other than maleimide or N-carbonylmaleimide and $R^5$ is a substituent other than indole, then $R^3$ is 2-alkyl or 3-alkyl. In some embodiments, $R_3$ and/or $R_7$ may be methyl.

In one embodiment, the compound of Formula I may be a compound selected from the group consisting of:

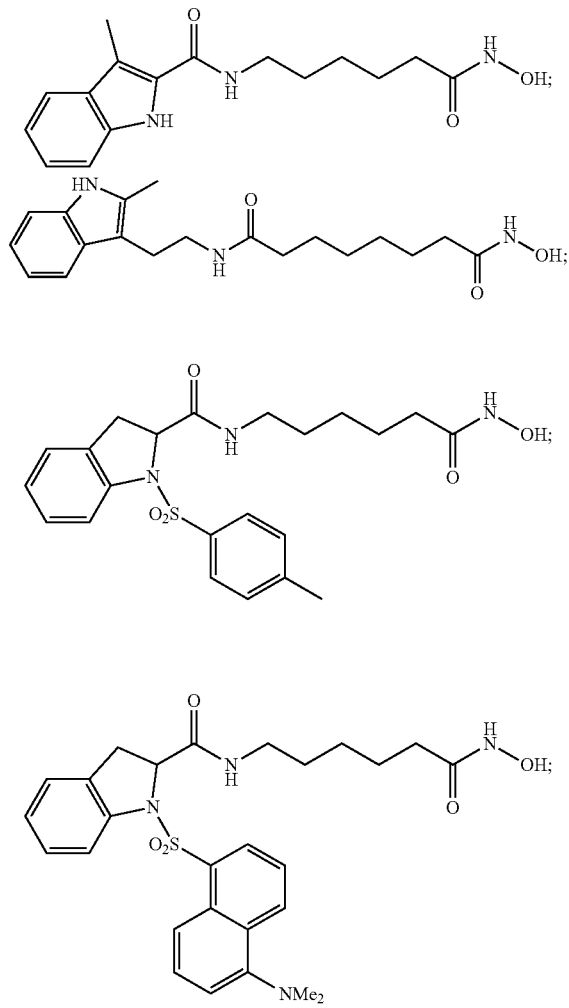

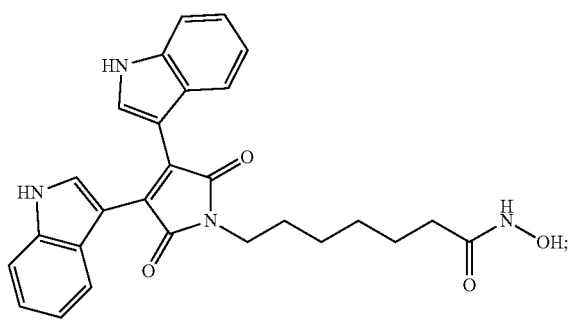

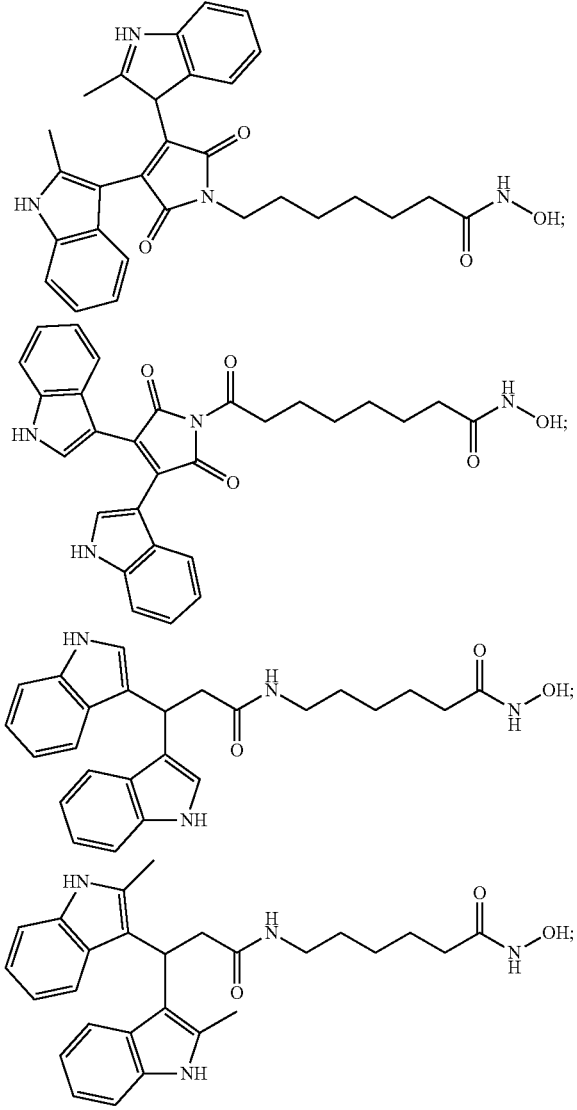

and the pharmaceutically acceptable salts thereof.

In a further embodiment, the compound of Formula I may be a compound having the formula:

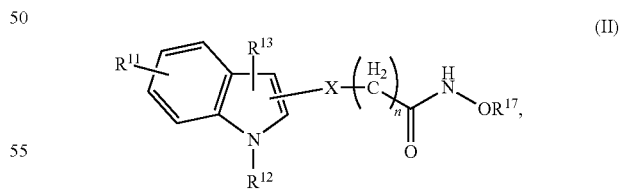

(II)

wherein $R^{11}$, $R^{13}$, $R^{14}$, and $R^{16}$ may be independently selected from the group consisting of H, hydroxyl, halogen and, optionally substituted, alkyl, alkenyl, alkynyl, cycloalkyl, aryl, heterocycle, heteroaryl, amino, alkoxy, carboxy, carbalkoxy, carboxamido, sulfonyl, sulfinyl, monoalkylaminosulfinyl, dialkylaminosulfinyl, monoalkylaminosufonyl, dialkylaminosulfonyl, alkylsulfonylamino, hydroxysulfonyloxy, alkoxysulfonyloxy, alkylsulfonyloxy, hydroxysulfonyl, alkoxysulfonyl, alkylsulfonylalkyl, monoalkylaminosulfonylalkyl, dialkylaminosulfonylalkyl, monoalkylaminosulfinylalkyl, and dialkylaminosulfinylalkyl.

X may be selected from the group consisting of:

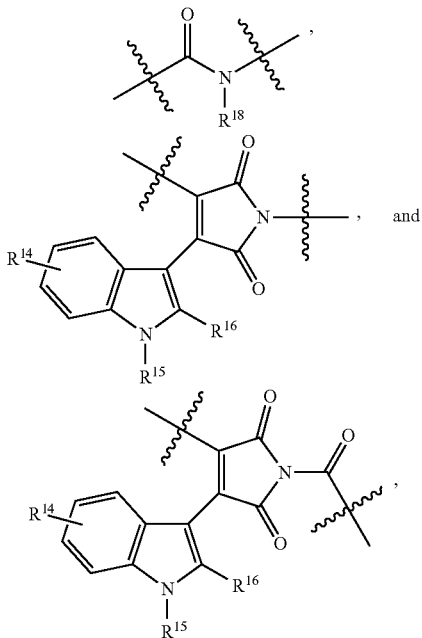

wherein $R^{18}$ may be selected from the group consisting of H and, optionally substituted, alkyl, alkenyl, cycloalkyl, aryl, heterocycle, and heteroaryl.

$R^{12}$ and $R^{15}$ may be independently selected from the group consisting of H and, optionally substituted, alkyl, sulfinyl, and sulfonyl.

$R^{17}$ may be selected from the group consisting of H and optionally substituted alkyl.

n may be an integer from 3 to 10; the dashed line may indicate the presence of a single bond or a double bond as allowed; with the proviso that, where X is amide, then $R^{13}$ is 2-alkyl or 3-alkyl, the dashed line indicating the presence of a double bond; and the pharmaceutically acceptable salts of the compound of Formula II. In certain embodiments, n may be an integer from 4 to 6. For example, n may be 5. In some embodiments, $R_{13}$ and/or $R_{16}$ may be methyl.

Additionally, the compound of Formula I or II may be a compound selected from the group consisting of:

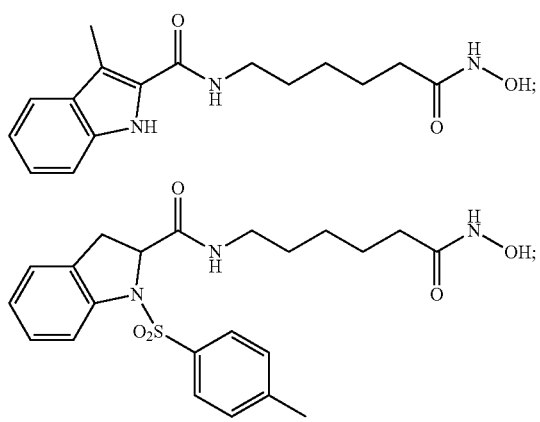

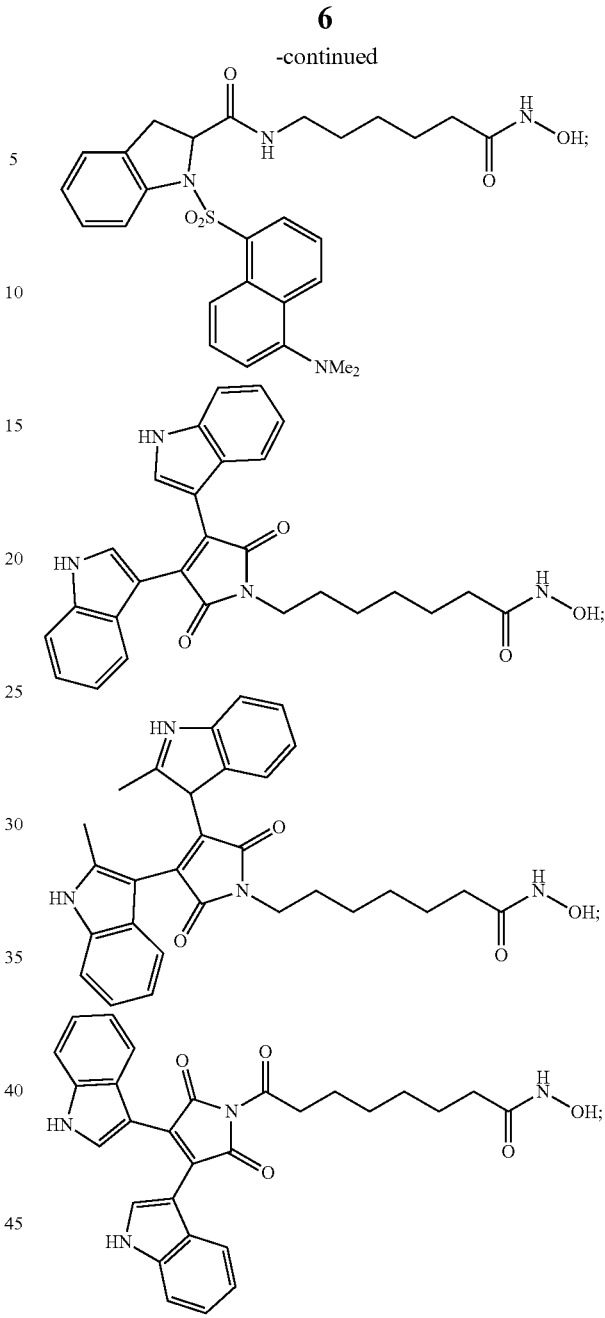

and the pharmaceutically acceptable salts thereof.

In another embodiment, the compound of Formula I may be a compound having the formula:

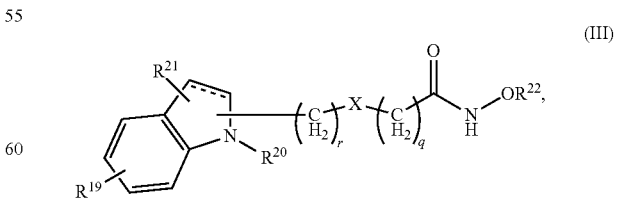

(III)

wherein $R^{19}$ and $R^{21}$ may be independently selected from the group consisting of H, hydroxyl, halogen and, optionally substituted alkyl, aryl, heterocycle, heteroaryl, sulfonyl, sulfinyl, alkoxy, and amino.

X may be selected from the group consisting of:

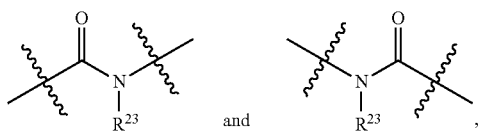

and wherein $R^{23}$ may be selected from the group consisting of H and, optionally substituted, alkyl, alkenyl, cycloalkyl, aryl, heterocycle, and heteroaryl.

$R^{20}$ may be selected from the group consisting of H and, optionally substituted, alkyl, sulfinyl, and sulfonyl.

$R^{22}$ may be selected from the group consisting of H and optionally substituted alkyl.

r may be an integer from 0 to 4; q may be an integer from 3 to 10; the dashed line may indicate the presence of a single bond or a double bond as allowed; with the proviso that, $R^{21}$ is 2-alkyl or 3-alkyl with dashed line indicating the presence of a double bond; and the pharmaceutically acceptable salts of the compound of Formula III. In certain embodiments, q may be an integer from 4 to 6. For example, q may be 5.

In another embodiment, the compound of Formula I or III may be a compound selected from the group consisting of:

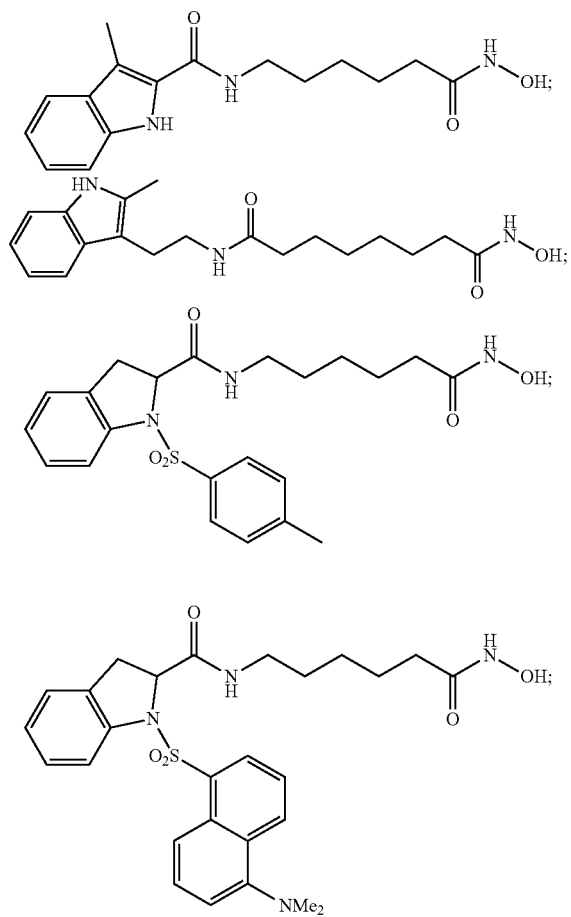

and the pharmaceutically acceptable salts thereof.

In another embodiment, the compound of Formula I may be a compound having the formula:

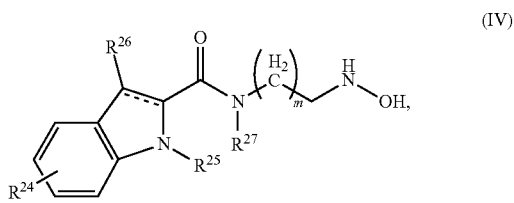

(IV)

wherein $R^{24}$ and $R^{26}$ may be independently selected from the group consisting of H, hydroxyl, halogen and, optionally substituted alkyl, aryl, heterocycle, heteroaryl, sulfonyl, sulfinyl, alkoxy, and amino.

$R^{25}$ may be selected from the group consisting of H and, optionally substituted, alkyl, sulfinyl, and sulfonyl.

$R^{27}$ may be selected from the group consisting of H and optionally substituted alkyl; m may be an integer from 3 to 10; the dashed line may indicate the presence of a single bond or a double bond as allowed; with the proviso that, $R^{26}$ is a substituent selected from the group consisting of hydroxyl, halogen and, optionally substituted alkyl, aryl, heterocycle, heteroaryl, sulfonyl, sulfinyl, alkoxy, and amino, with the dashed line indicating the presence of a double bond and the pharmaceutically acceptable salts of the compound of Formula IV. In certain embodiments, m may be an integer from 4 to 6. For example, m may be 5.

In another embodiment, the compound of Formula I or IV may be a compound selected from the group consisting of:

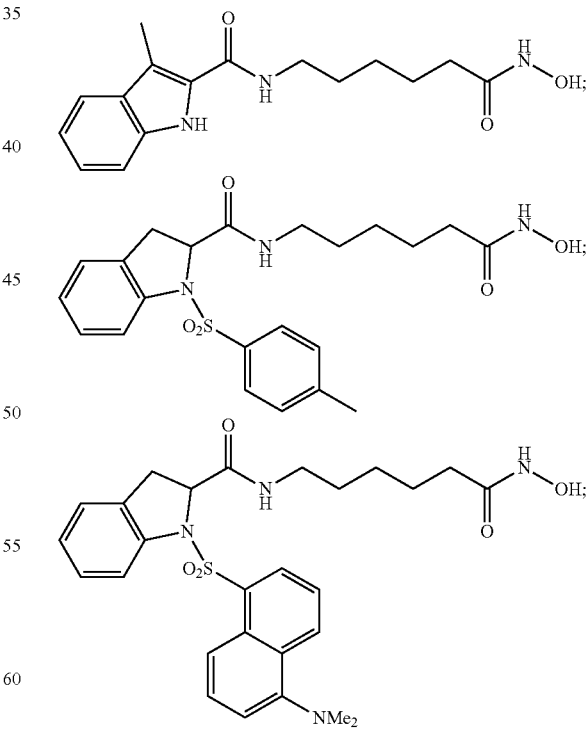

and the pharmaceutically acceptable salts thereof.

In another aspect, the invention includes a pharmaceutical formulation that may be in unit dosage form. The pharmaceutical formulation of the invention may include a compound of Formula I and may be provided in an amount effective to inhibit histone deacetylase (HDAC) and activate ataxia telangiectasia mutated (ATM) in a patient in need thereof and may include at least one physiologically compatible carrier medium.

The pharmaceutical formulation of the invention may include a compound of Formula II, Formula III, and/or Formula IV.

In an additional aspect, the invention includes a method of treating a disease in a patient in need thereof. The method may include administering a therapeutically effective amount of at least one compound configured to inhibit histone deacetylase (HDAC) and activate ataxia telangiectasia (ATM). The at least one compound may be a compound of Formula I.

In one embodiment, the method may include administering at least one compound selected from the group consisting of:

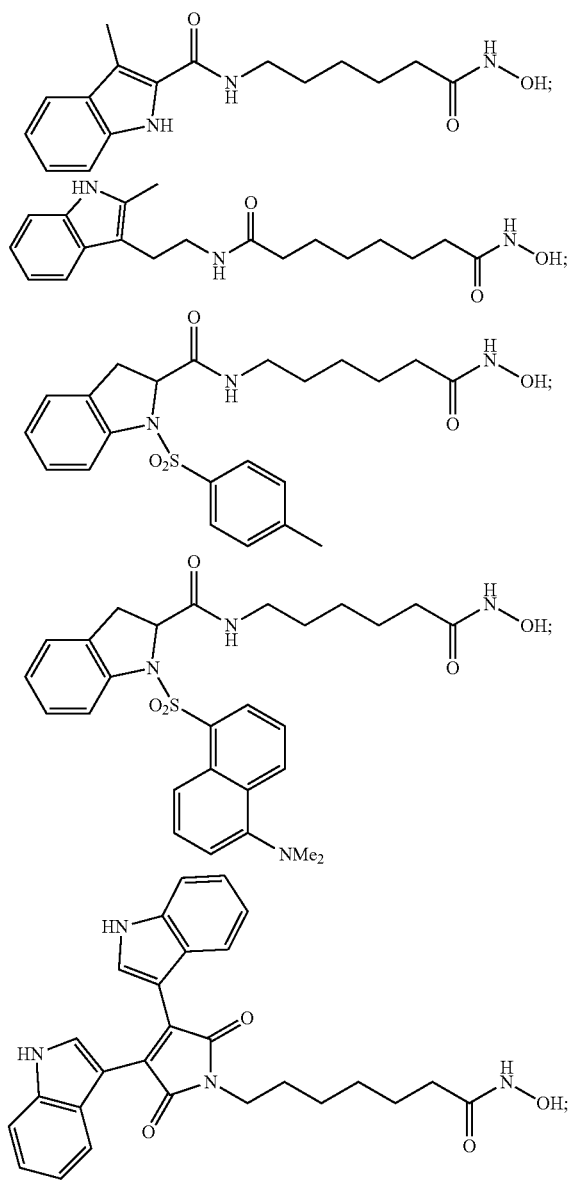
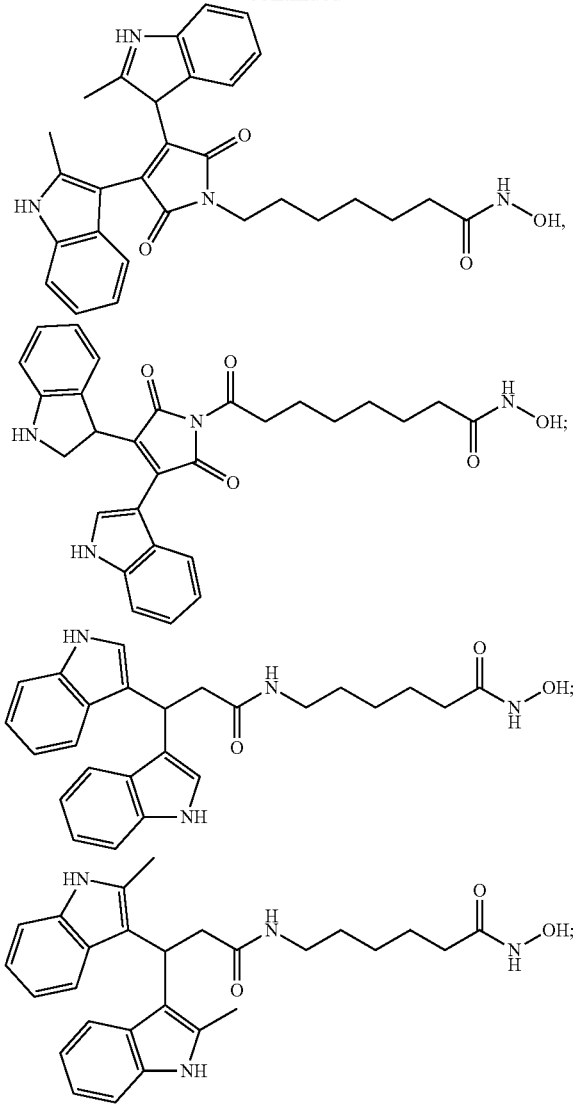

and the pharmaceutically acceptable salts thereof.

In other embodiments, the methods of the invention may include administering at least one compound of Formula II, Formula III, and/or Formula IV. The methods of the invention may include the administration of the at least one compound in dosage unit form that may further include a physiologically acceptable carrier medium.

In further embodiments, the diseases treated by the methods of the invention may include a disease selected from the group consisting of cancer, immunological disorders, and neurological disorders.

When the disease treated by the methods of the invention is cancer, the cancer may be selected from those cancers listed in Table 1. In certain aspects, the cancer may be selected from the group consisting of gastric cancer, prostate cancer, colon cancer, breast cancer, Non-Hodgkin's lymphoma, ovarian cancer, sarcoma, lung cancer, leukemia, myeloma, testicular cancer, cervical cancer, pancreatic cancer, head and neck cancer, rectal cancer, and brain cancer. The method may further include the step of administering to said patient an amount of radiotherapy configured to treat said cancer.

When the disease treated by the methods of the invention is an immunological disorder, the immunological disorder may be selected from the group consisting of systemic lupus erythematosus and rheumatoid arthritis.

When the disease treated by the methods of the invention is a neurological disorder, the neurological disorder may be selected from the group consisting of stroke, Huntington's disease, spinal muscular atrophy (SMA), Parkinson's disease, Alzheimer's, Multiple Sclerosis, and Amyotrophic Lateral Sclerosis (ALS). In some aspects, the neurological disorder treated by the methods of the invention may be Alzheimer's disease or multiple sclerosis.

In still further embodiments, the method of the invention may be a second or third line method of treatment for the patient and administration of the compound occurs after performance of a first or second therapy on the patient that failed to treat the disease.

In a further aspect, the invention includes a method of treatment that may include sensitizing cancerous cells to radiotherapy and protecting non-cancerous cells from radiotherapy in a patient in need thereof, wherein cancerous cells are sensitized to radiotherapy by inhibiting histone deacetylase (HDAC) and non-cancerous cells are protected from radiotherapy by activating ataxia telangiectasia mutated (ATM). The method may include administering a therapeutically effective amount of at least one compound of Formula I.

In other embodiments, the method may include administering at least one compound of Formula II, Formula III, and/or Formula IV.

In still further embodiments, the cancerous cells may be the result of a cancer selected from those cancers listed in Table 1. For example, the cancerous cells may be the result of a cancer selected from the group consisting of gastric cancer, prostate cancer, colon cancer, breast cancer, Non-Hodgkin's lymphoma, ovarian cancer, sarcoma, lung cancer, leukemia, myeloma, testicular cancer, cervical cancer, pancreatic cancer, head and neck cancer, rectal cancer, and brain cancer.

The method of the invention may further include the step of administering to the patient an amount of radiotherapy configured to treat the cancerous cells.

Accordingly, as briefly described herein, the present invention includes compounds, compositions, and methods of treatment that provide treatment solutions to answer the needs in the field.

BRIEF DESCRIPTION OF THE DRAWINGS

The foregoing summary and the following detailed description of the exemplary embodiments of the present invention may be further understood when read in conjunction with the appended drawings, in which:

FIG. 9 demonstrates, in tabular form, the cytotoxic effect of certain compounds of the invention on breast cancer cells (MCF7 cells) and healthy breast tissue cells (184A1 cells) in both an MTT Cytotoxicity assay and Clonogenic Cytotoxicity assay. Specifically, the following compounds were tested: N-(6-(hydroxyamino)-6-oxohexyl)-3-methyl-1H-indole-2-carboxamide (SP-1-161); $N^1$-hydroxy-$N^6$-(2-(2-methyl-1H-indol-3-yl)ethyl)octanediamide (SP-1-163); (S)—N-(6-(hydroxyamino)-6-oxohexyl)-1-tosylindoline-2-carboxamide (SP-1-169); and (S)-1-((5-(dimethylamino)naphthalene-1-yl)sulfonyl)-N-(6-(hydroxyamino)-6-oxoheyl)indoline-carboxamide (SP-1-171).

FIG. 10 demonstrates, in tabular form, the effects of N-(6-(hydroxyamino)-6-oxohexyl)-3-methyl-1H-indole-2-carboxamide (SP-1-161) on the radiation survival curves and parameters for normal breast epithelial cells (184A1 cells) and breast cancer cells (MCF7 cells).

FIG. 13 demonstrates, in tabular form, the cytotoxic activity of SP-1-161, SP-1-229, and SP-1-303 were tested against breast cancer (MCF7), prostate cancer (PC3), cervical cancer (CasKi), and head and neck cancer (SQ20B) cell lines. Suberoylanilide hydroxamic acid (SAHA or Vorinostat) was also included in the assay as a positive control. NBE=Normal breast epithelial; BC=Breast cancer; and NPE=Normal prostate epithelial.

DETAILED DESCRIPTION OF THE INVENTION

Figure 1:
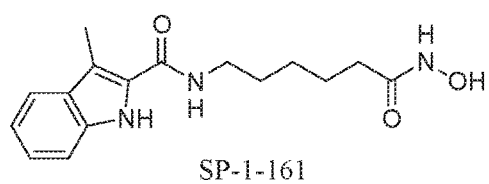
FIG. 1 schematically illustrates exemplary embodiments of Formula I.
Figure 1:
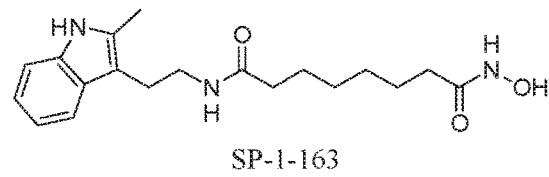
Figure 1:
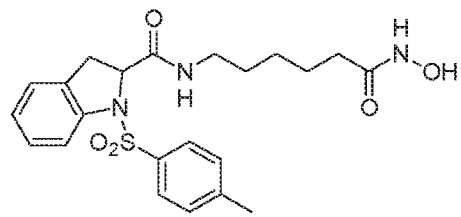
Figure 1:
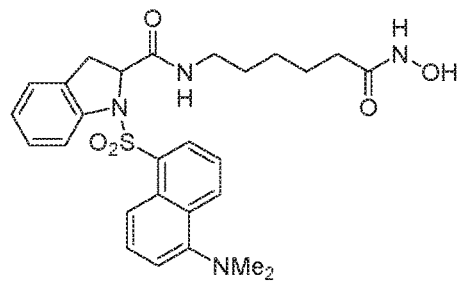
Figure 1:
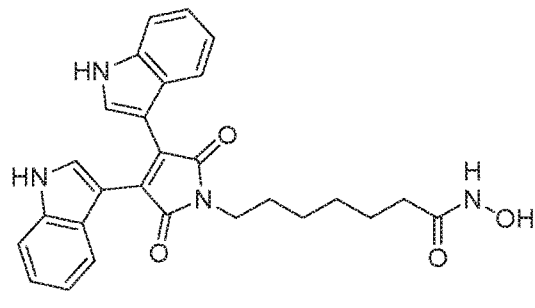
Figure 1:
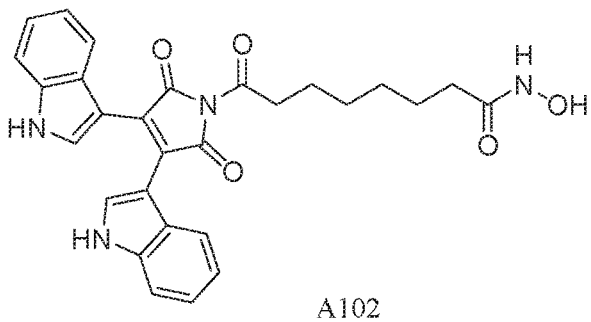
Figure 1:
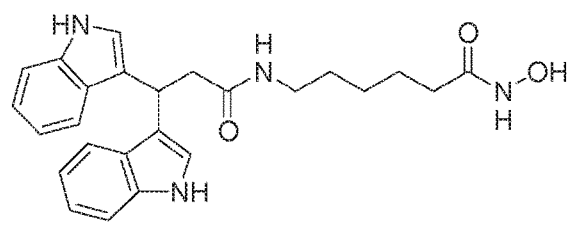
Figure 1:
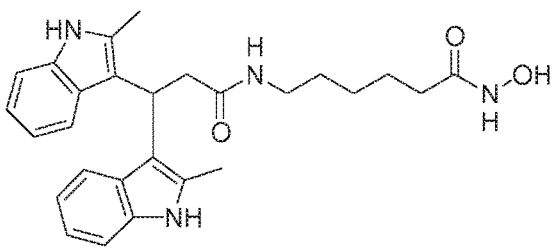
Figure 1:
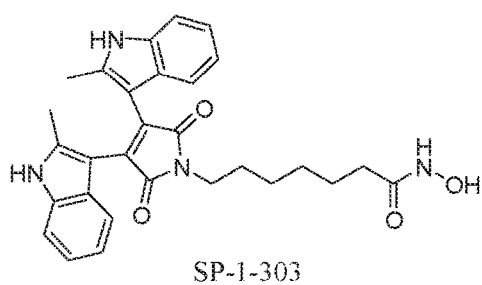

The present invention relates generally to compounds, and compositions that include such compounds, which may be HDAC inhibitors and ATM activators. More specifically, the compounds of the invention are dual function compounds as represented in Formulas I-IV, which may be used in treating diseases that implicate HDAC and/or ATM, such as certain cancers, immunological diseases, and neurological diseases.

Regarding the compounds of the invention, which are encompassed within Formulas I-IV, as used herein, the term "alkyl" denotes branched or unbranched hydrocarbon chains, having about 1 to 10 carbons, such as, methyl, ethyl, n-propyl, iso-propyl, n-butyl, sec-butyl, iso-butyl, tert-butyl, 2-methylpentyl pentyl, hexyl, isohexyl, heptyl, 4,4-dimethyl pentyl, octyl, 2,2,4-trimethylpentyl and the like. "Substituted alkyl" includes an alkyl group optionally substituted with one or more functional groups which are attached commonly to such chains, such as, hydroxy, halogen, mercapto or thio, cyano, alkylthio, carboxy, carbalkoxy, amino, nitro, alkoxy, or optionally substituted, alkenyl, alkynyl, heterocyclyl, aryl, heteroaryl, and the like to form alkyl groups such as trifluoro methyl, 3-hydroxyhexyl, 2-carboxypropyl, 2-fluoroethyl, carboxymethyl, cyanobutyl, phenethyl, benzyl and the like.

The term "halogen" or "halo" as used herein alone or as part of another group refers to chlorine, bromine, fluorine, and iodine.

The term "alkoxy" refers to alkyl-O—, in which alkyl is as defined above.

The term "alkylthio" refers to alkyl-S—, in which alkyl is as defined above.

The term "alkylamino" refers to alkyl-N—, in which alkyl is as defined above.

The term "carboxy" refers to the moiety —C(=O)OH.

The term "carbalkoxy" refers to the moiety —C(=O)O-alkyl, in which alkyl is as defined above.

The term "carboxamido" refers to the moiety —C(=O)—NR'R", in which R' and R", each may independently represent H, alkyl, or aryl, all as defined herein.

The term "alkylcarbonylamino" refers to the moiety —NR'C(=O)—R", in which R' and R", each may independently represent H, alkyl, or aryl, all as defined herein.

The term "alkylsulfonyl" refers to the moiety —S(=O)$_2$-alkyl, in which alkyl is as previously defined.

The term "alkylsulfonyloxy" refers to the moiety —OS(=O)$_2$-alkyl, wherein alkyl is as previously defined.

The term "amino(monoalkylamino-, dialkylamino-)sulfinyl" refers to the moiety —S(=O)NR'R" in which R' and R" each may independently represent H, alkyl, or aryl, all as defined herein.

The term "amino(monoalkylamino-, dialkylamino-)sulfonyl" refers to the moiety —S(=O)$_2$NR'R", in which R' and R" each may independently represent H, alkyl, or aryl, all as defined herein.

The term "alkylsulfonylamino" refers to the moiety —NHS(=O)$_2$-alkyl, in which alkyl is as previously defined.

The term "hydroxysulfonyloxy" refers to the moiety —OS(=O)$_2$OH.

The term "alkoyxsulfonyloxy" refers to the moiety —OS(=O)$_2$O-alkyl, in which alkyl is as previously defined.

The term "alkylsulfonyloxy" refers to the moiety —OS(=O)$_2$-alkyl, in which alkyl is as previously defined.

The term "hydroxysulfonyl" refers to the moiety —S(=O)$_2$OH.

The term "alkoxysulfonyl" refers to the moiety —S(=O)$_2$O-alkyl, wherein alkyl is as previously defined.

The term "alkylsulfonylalkyl" refers to the moiety -alkyl-S(=O)$_2$-alkyl, wherein each alkyl may be as previously defined.

The term "amino(monoalkylamino-, dialkylamino-)sulfonylalkyl" refers to the moieties -alkyl-S(=O)$_2$—NR'R", wherein alkyl is as previously defined, and R' and R" each may independently represent H, alkyl, or aryl, all as defined herein.

The term "amino(monoalkylamino-, dialkylamino-)sulfinylalkyl" refer to the moieties -alkyl-S(=O)—NR'R", wherein alkyl is as previously defined, and R" and R" each may independently represent H, alkyl, or aryl, all as defined herein.

Unless otherwise indicated, the term "cycloalkyl" as employed herein alone or as part of another group includes saturated or partially unsaturated (containing 1 or more double bonds) cyclic hydrocarbon groups containing 1 to 3 rings, including monocyclicalkyl, bicyclicalkyl and tricyclicalkyl, containing a total of 3 to 20 carbons forming the rings, or about 3 to 10 carbons, forming the ring and which may be fused to 1 or 2 aromatic rings as described for aryl, which include cyclopropyl, cyclobutyl, cyclopentyl, cyclohexyl, cycloheptyl, cyclooctyl, cyclodecyl, cyclododecyl, and cyclohexenyl.

"Substituted cycloalkyl" includes a cycloalkyl group optionally substituted with 1 or more substituents such as halogen, alkyl, substituted alkyl, alkoxy, hydroxy, aryl, substituted aryl, aryloxy, cycloalkyl, alkylamido, alkanoylamino, oxo, acyl, arylcarbonylamino, amino, nitro, cyano, thiol and/or alkylthio and/or any of the substituents included in the definition of "substituted alkyl."

Unless otherwise indicated, the term "alkenyl" as used herein by itself or as part of another group refers to straight or branched chain of 2 to 20 carbons, or about 2 to 12 carbons, or about 2 to 8 carbons in the normal chain, which include one or more double bonds in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 4,8,12-tetradecatrienyl, and the like. "Substituted alkenyl" includes an alkenyl group optionally substituted with one or more substituents, such as the substituents included above in the definition of "substituted alkyl" and "substituted cycloalkyl."

Unless otherwise indicated, the term "alkynyl" as used herein by itself or as part of another group refers to straight or branched chain of 2 to 20 carbons, or about 2 to 12 carbons, or about 2 to 8 carbons in the normal chain, which include one or more triple bonds in the normal chain, such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl, 3-undecynyl, 4-dodecynyl and the like. "Substituted alkynyl" includes an alkynyl group optionally substituted with one or more substituents, such as the substituents included above in the definition of "substituted alkyl" and "substituted cycloalkyl."

Unless otherwise indicated, the term "aryl" or "Ar" as employed herein alone or as part of another group refers to monocyclic, bicyclic, and/or polycyclic aromatic groups containing 6 to 10 carbons in the ring portion (such as phenyl or naphthyl including 1-naphthyl and 2-naphthyl) and may optionally include one to three additional rings fused to a carbocyclic ring or a heterocyclic ring, such as aryl, cycloalkyl, heteroaryl, or cycloheteroalkyl rings or substituted forms thereof.

"Substituted aryl" includes an aryl group optionally substituted with one or more functional groups, such as halo, alkyl, haloalkyl (e.g., trifluoromethyl), alkoxy, haloalkoxy (e.g., difluoromethoxy), alkenyl, alkynyl, cycloalkyl-alkyl, cycloheteroalkyl, cycloheteroalkylalkyl, aryl, heteroaryl, arylalkyl, aryloxy, aryloxyalkyl, arylalkoxy, alkoxycarbonyl, alkylcarbonyl, arylcarbonyl, arylalkenyl, aminocarbonylaryl, arylthio, arylsulfinyl, arylazo, heteroarylalkyl, heteroarylalkenyl, heteroarylheteroaryl, heteroaryloxy, hydroxy, nitro, cyano, amino, substituted amino wherein the amino includes 1 or 2 substituents (which are optionally substituted alkyl, aryl or any of the other substituents recited herein), thiol, alkylthio, arylthio, heteroarylthio, arylthioalkyl, alkoxy arylthio, alkylaminocarbonyl, arylaminocarbonyl, aminocarbonyl, alkylcarbonyloxy, arylcarbonyloxy, alkylcarbonylamino, arylcarbonylamino, arylsulfinyl, arylsulfinylalkyl, arylsulfonylamino, or arylsulfonaminocarbonyl and/or any of the alkyl substituents recited herein.

Unless otherwise indicated, the term "heteroaryl" as used herein alone or as part of another group refers to a 5- to 7-membered aromatic ring which includes 1, 2, 3 or 4 hetero atoms such as nitrogen, oxygen or sulfur and such rings fused to an aryl, cycloalkyl, heteroaryl or heterocycloalkyl ring (e.g. benzothiophenyl, indolyl), and includes possible N-oxides. "Substituted heteroaryl" includes a heteroaryl group optionally substituted with 1 to 4 substituents, such as the substituents included above in the definition of "substituted alkyl" and "substituted cycloalkyl." Substituted heteroaryl also includes fused heteroaryl groups which include, for example, quinoline, isoquinoline, indole, isoindole, carbazole, acridine, benzimidazole, benzofuran, isobenzofuran, benzothiophene, phenanthroline, purine, and the like.

Moreover, the terms "heterocyclo," "heterocycle," or "heterocyclic ring," as used herein, refer to an unsubstituted or substituted stable 5- to 7-membered monocyclic ring system which may be saturated or unsaturated, and which consists of carbon atoms and from one to four heteroatoms selected from N, O or S, and wherein the nitrogen and sulfur heteroatoms may optionally be oxidized, and the nitrogen heteroatom may optionally be quaternized. The heterocyclic ring may be attached at any heteroatom or carbon atom which results in the creation of a stable structure. Examples of such heterocyclic groups include, but are not limited to, piperidinyl, piperazinyl, oxopiperazinyl, oxopiperidinyl, oxopyrrolidinyl, oxoazepinyl, azepinyl, pyrrolyl, pyrrolidinyl, furanyl, thienyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isooxazolyl, isoxazolidinyl, morpholinyl, thiazolyl, thiazolidinyl, isothiazolyl, thiadiazolyl, tetrahydropyranyl, thiamorpholinyl, thiamorpholinylsulfoxide, thiamorpholinylsulfone, and oxadiazolyl.

As used herein, the term "optionally substituted" may indicate that a chemical moiety referred to, for example, alkyl, aryl, heteroaryl, may be unsubstituted or substituted with one or more groups including, without limitation, alkyl, alkenyl, alkynyl, cycloalkyl, arylalkyl, aryl, heterocycle, heteroaryl, hydroxyl, amino, alkoxy, halogen, carboxy, carbalkoxy, carboxamido, monoalkylaminosulfinyl, dialkylaminosulfinyl, mono alkylaminosulfonyl, dialkylaminosulfonyl, alkylsulfonylamino, hydroxysulfonyloxy, alkoxysulfonyloxy, alkylsulfonyloxy, hydroxysulfonyl, alkoxysulfonyl, alkylsulfonylalkyl, monoalkylaminosulfonylalkyl, dialkylaminosulfonylalkyl, monoalkylaminosulfinylalkyl, dialkylaminosulfinylalkyl and the like. The chemical moieties of Formulas I-IV, above, that may be optionally substituted include alkyl, alkenyl, alkynyl, cycloalkyl, arylalkyl, aryl, heterocycle, and heteroaryl. For example, optionally substituted alkyl may include both propyl and 2-chloro-propyl. Additionally, "optionally substituted" is also inclusive of embodiments where the named substituent or substituents have multiple substituents rather than simply a single substituent. For example, optionally substituted aryl may include both phenyl and 3-methyl-5-ethyl-6-chloro-phenyl.

The compounds of the invention may be administered as salts, which are also within the scope of this invention. Pharmaceutically acceptable (i.e., non-toxic, physiologically compatible) salts are preferred. If the compounds of the invention have, for example, at least one basic center, they can form acid addition salts. These are formed, for example, with strong inorganic acids, such as mineral acids, for example sulfuric acid, phosphoric acid or a hydrohalic acid, with strong organic carboxylic acids, such as alkane carboxylic acids of 1 to 4 carbon atoms which are unsubstituted or substituted, for example, by halogen, for example acetic acid, such as saturated or unsaturated dicarboxylic acids, for example oxalic, malonic, succinic, maleic, fumaric, phthalic or terephthalic acid, such as hydroxycarboxylic acids, for example ascorbic, glycolic, lactic, malic, tartaric or citric acid, such as amino acids, (for example aspartic or glutamic acid or lysine or arginine), or benzoic acid, or with organic sulfonic acids, such as ($C_1$-$C_4$) alkyl or arylsulfonic acids which are unsubstituted or substituted, for example by halogen, for example methyl- or para-toluene-sulfonic acid. Corresponding acid addition salts can also be formed having plural basic centers, if desired.

The compounds of the invention having at least one acid group (e.g., carboxylic acid or hydroxamic acid) can also form salts with suitable bases. Representative examples of such salts include metal salts, such as alkali metal or alkaline earth metal salts, for example sodium, potassium or magnesium salts, or salts with ammonia or an organic amine, such as morpholine, thiomorpholine, piperidine, pyrrolidine, a mono, di or tri-lower alkylamine, for example ethyl, tert-butyl, diethyl, diisopropyl, triethyl, tributyl or dimethylpropylamine, or a mono, di or trihydroxy lower alkylamine, for example mono, di or triethanolamine. Corresponding internal salts may also be formed.

For example, certain salts of the compounds described herein which contain a basic group include monohydrochloride, hydrogensulfate, methanesulfonate, phosphate or nitrate. Moreover, certain salts of the compounds described herein which contain an acid group include sodium, potassium and magnesium salts and pharmaceutically acceptable organic amines.

All stereoisomers of the compounds of the invention, either in a mixture or in pure or substantially pure form, are considered to be within the scope of this invention. The compounds of the invention may have asymmetric centers at any of the carbon atoms including any one of the substituents. Consequently, compounds of the invention may exist in enantiomeric or diastereomeric forms or in mixtures thereof. Furthermore, where a stereocenter existing in a compound of the invention is represented as a racemate, it is understood that the stereocenter may encompass the racemic mixture of R and S isomers, the S isomers, and the R isomers. The processes for preparation of such compounds can utilize racemates, enantiomers, or diastereomers as starting materials. When diastereomeric or enantiomeric products are prepared, they can be separated by conventional methods including, chromatographic, chiral HPLC, fractional crystallization, or distillation. Some compounds of the present invention have groups including alkenyls, iminyls, and the like, which may exist as entgegen (E) or zusammen (Z) conformations, in which case all geometric forms thereof, both E and Z, cis and trans, and mixtures thereof, are within the scope of the present invention. Accordingly, when such geometric isomeric products are prepared, they can be separated by conventional methods for example, chromatographic, HPLC, distillation or crystallization.

Specific compounds of the invention include those compounds set forth in FIG. 1. In certain aspects, the compounds of the invention include those compounds set forth in FIG. 2. Certain compounds of the invention include N-(6-(hydroxyamino)-6-oxohexyl)-3-methyl-1H-indole-2-carboxamide (i.e., SP-1-161) and $N^{1'}$-hydroxy-$N^6$-(2-(2-methyl-1H-indol-3-yl)octanediamide (i.e., SP-1-163). In some embodiments, the compounds of the invention may include SP-1-161, SP-1-163, SP-1-229, and SP-1-303.

The compounds of the invention may be used as part of a therapy or methodology in treating a variety of diseases or conditions that implicate HDAC inhibition and/or ATM activation. For example, such diseases may include cancer, immunological disorders, and neurological disorders.

Cancer is the second leading cause of death in the United States after heart disease. The American Cancer Society estimates that 1,665,540 new cancer cases are expected to have been diagnosed in 2014 with 585,720 cancer-related deaths.

The standard treatments of cancer include surgery, radiotherapy, and chemotherapy. Each treatment modality carries risks and benefits, and cancer recurrences underlie efforts to improve the outcomes of treatment. In particular, recent advances in surgical and radiation therapy technologies, employing computational and robotic methods, have plateaued efficacy of local-regional treatments. Moreover, targeted agents to personalize chemotherapy have altered the cancer treatment paradigm.

Radiation therapy (i.e., radiotherapy) involves the treatment of cancer and other diseases using ionizing radiation. Ionizing radiation deposits energy that injures or destroys cells in targeted tissues by damaging their genetic material and subsequently interfering with a cell's ability to grow and/or replicate. Radiation exposure damages cancer cells and normal cells, but the normal cells activate processes to better repair themselves and may continue to function properly. Radiotherapy may be used to treat solid tumors (e.g., cancers of the head and neck, breast, prostate, rectum, uterus, lung, brain, kidney, uterus, and cervix). Radiotherapy may also be used to treat cancers such as leukemias and lymphomas. Radiotherapies used for leukemias and lymphomas may include total body radiation therapy in protocols preparing patients for bone marrow transplants. Radiotherapy may be more effective when the targeted cancer tissues are more sensitive to the effects of radiation than surrounding normal tissues.

The radiation responses of different cancers or tumors may vary as a function of histology, cellular doubling time, oxygenation, nutrient availability, repair capacity, and other factors. Some cancers are readily cured using ionizing radiation doses within normal tissue tolerances, while other types of cancer may not be very responsive to radiation. Furthermore, radiation responses of tumors with the same histology may show considerable heterogeneity and reduce the therapeutic effects of the therapy. Thus, a primary challenge facing radiotherapy is the differentiation between the more radiosensitive tumors versus less radiosensitive tumors and the surrounding healthy tissues.

Investigations into the molecular bases underlying cellular radiation responses have provided dramatic mechanistic insight. Signal transduction pathways have been implicated to play important roles in cellular responses to ionizing radiation. Induction of gene expression by these cascades under various conditions has been shown to result in cell cycle arrest, activation of DNA repair processes, and activation of programmed cell death (apoptosis). Disruption of critical signaling pathways in cancer cells may result in enhanced cytotoxic effects following radiation exposure. Certain cells may be disrupted by interfering with the histone acetylation and deacetylation processes of the cells.

Histone acetylation and deacetylation play important roles in chromatin folding and maintenance. Acetylation appears to play a role in the epigenetic regulation of chromatin structure, and gene expression, through the balance of histone acetyltransferase (HAT) and histone deacetylase (HDAC) activities. Increased acetylation of histones leads to changes in chromatin structure and accessibility for key cellular proteins to specific target sites. HATs acetylate lysine groups at the amino terminal tails of nuclear histones to neutralize positive charges on the histones, yielding a more open, transcriptionally active chromatin structure. In contrast, the HDACs deacetylate and suppress transcription. In this model, inhibitors of HDACs bias the balance toward a more acetylated state. Such a shift in the relative activities of these enzymes may affect gene expression necessary for DNA repair, replication, cell cycle checkpoint activation and tumor suppression.

Human HDACs may be divided into four classes based on structure, sequence homology, and domain organization. Class I consists of HDACs 1, 2, 3, 8, and 11, albeit a recent report puts HDAC 11 into a new class, class IV, based on a phylogenetic analysis. Class I HDACs are nuclear and play roles in cell proliferation and apoptosis. Class II includes HDACs 4, 5, 6, 7, 9, and 10. These enzymes are characterized by a large $NH_2$-terminal domain or a second catalytic site and their expression is more restricted, suggesting roles in cellular differentiation and development. Class III enzymes, include the sirtuins (SIRTs), and are NAD-dependent deacetylases. These are not inhibited by Trichostatin A (TSA) or other hydroxamates.

HDACs are found in the nuclear and cytoplasmic compartments. Although they are involved in critical cellular functions, such as cell cycle regulation and apoptosis, a key function of HDACs is transcriptional regulation. HDACs function as components of large multi-protein complexes that bind to promoters and repress transcription. Class II compounds shuttle between the nucleus and the cytoplasm. However, certain classes of HDACs have conserved deacetylase core domains of approximately 400 amino acids and zinc binding sites. It is the core domain that presents the principal target for design of inhibitory small molecules.

In response to DNA damage, signal transduction pathways may be activated to regulate cell cycle arrest, repair, differentiation, apoptosis, and transcription. Such responses are a complex feature of the cellular radiation phenotype, and their effectiveness may determine cell survival or death. DNA damage checkpoints generate signals that arrest cell cycle progression until the damage is repaired. When damaged DNA is repaired, checkpoint signals are reversed to resume cell cycle progression. Such DNA-directed processes are accompanied by highly localized changes in chromatin structure. Various recent studies have implicated chromatin structure in DNA damage signaling and repair. Post-translational histone modifications regulate chromatin structure and access for proteins to damaged DNA sites as reported for repair and signaling proteins to the damaged regions of DNA.

Early HDAC inhibitors (e.g., benzamides) were investigated as differentiating agents, without full understanding of their molecular mechanisms. Some of these agents have advanced to clinical trials. The full recognition of the potential for HDAC inhibitors was advanced with the discovery and development of hydroxamic acid inhibitors. Hydroxamic acid based compounds (e.g., suberoylanilide hydroxamic acid (SAHA)) have been developed for clinical application, and have proven to be relatively non-toxic. SAHA has been approved by the FDA for the treatment of cutaneous T-cell lymphoma. Certain HDAC inhibitors have been described in U.S. Pat. Nos. 7,507,828; 7,842,835; 8,067,600; 8,222,451; and 8,748,463; the entirety of which are incorporated herein by reference.

Other chemical families of HDAC inhibitors, including depsipeptide and valproic acid, have been shown to inhibit cancer cell growth in vitro and in vivo. Modulation of p53, ErbB1, ErbB2 and Raf-1 expression have been observed following exposure of lung cancer cells to depsipeptide, a drug currently in clinical trials. For example, Valproic acid has been used clinically as an anti-epileptic agent, with excellent reasonable toxicity profile and has been shown to be involved in the proteolysis of HDAC 2.

Several lines of evidence support targeting HDACs to achieve radiation sensitization of cancer cells following exposures to HDAC inhibitors. The responses of cells to ionizing radiation may be viewed as a complex phenotype involving various signal transduction pathways associated with the activation of stress responses, cell cycle regulation, DNA repair and regulation of apoptosis.

Damage sensing and repair proteins, including ATM, MRE11, γ-H2AX and 53BP1, have been associated with changes in chromatin structure. Proteins that bind directly to ends of broken DNA include Ku, DNAPK and PARP. ATM kinase is considered a primary regulator of responses to DNA double strand breaks and activates a number of downstream effectors, including H2AX, MDC1/NFBD1, 53BP1, Brca1, and MRN (Mre11, Rad50 and Nbs1). These various molecules provide potential intermediate endpoints for studies of effects of HDAC inhibitors on radiation sensitivies of cancer cells.

Regarding ATM in particular, ATM may mediate the cell repair response after DNA damage (e.g., double strand breaks (DSBs)) or during periods of oxidative stress. ATM may be activated by its phosphorylation at serine 1981 (Ser1981) triggered by ionizing radiation induced DNA damage, leading to phosphorylation of critical factors involved in DNA repair, apoptosis, and cell cycle checkpoint regulation. ATM recruitment to and activation by DSBs requires the MRN complex which functions both upstream and downstream of ATM. MRN senses DSBs and activates ATM, but it is also phosphorylated and activated by ATM. MRN participates more directly in DNA repair by binding and tethering broken DNA ends close to one another and by processing DNA ends via the nuclease activity of Mre11. ATM may also be indirectly activated by Trichostatin A (TSA), an HDAC inhibitor, by a process that involves chromatin changes in the absence of DNA breaks.

As used herein, the term "ATM activation" refers to the phosphorylation of ATM, which provides phospho-ATM. ATM may be directly or indirectly activated. For direct ATM activation, a ligand or compound may activate ATM by a process that is not the downstream result of HDAC inhibition. In certain instances, HDAC inhibition may result in some measurable ATM activation due to the resulting downstream effects of HDAC inhibition, which may include cell damage. However, without being limited to any one theory, 3,3'-diindolylmethane (DIM) is a direct activator of ATM and protects against γ radiation by stimulation of an ATM-driven DDR-like response, without causing DNA damage. This response may involve signalling through an MRN/ATM/BRCA1 pathway. By contrast, indirect ATM activation arises where a ligand or compound activates ATM as a byproduct of the inhibition of HDAC protein.

Certain compounds of the invention (e.g., dual function compounds) are direct ATM activators. Indeed, certain compounds of the invention may provide direct ATM activation activity, in addition to indirect ATM activation activity which may result from HDAC inhibition. These activities may be measured by examining the phosphorylation of ATM upon treatment with a compound of the invention. As will be discussed herein (see Example 13, FIG. 12), the compounds of the invention may include both a hydroxamic acid moiety and an indole moiety where at least the indole moiety is demonstrated to enhance direct ATM activation. Therefore, certain compounds of the invention are dual function compounds in that they are HDAC inhibitors and ATM activators, which may directly activate ATM.

Certain chemical classes of HDAC inhibitors are radiation sensitizers. As used herein, the term "radiosensitizing agent" which may be read also as a "radiosensitizer" denotes an agent having an effect of enhancing the sensitivity of cancerous and/or neoplastic cells to radiation. As a generalization, chemosensitization and radiosensitization are important properties of HDAC inhibitors and may offer expanded clinical opportunities for these agents. General properties that may be expected to have an effect on radiation sensitivities of cancer cells include differentiation, growth inhibition, changes in gene expression and apoptosis. Key reported acetylation mechanisms have involved histones and tubulin and a variety of other non-histone proteins.

Generally, chemotherapeutic compounds, such as HDAC inhibitors, may have varied bioactivities. For example, chemotherapeutic compounds may have cytotoxic activity against cancerous cells and/or non-cancerous cells. Additionally, chemotherapeutic compounds may also exhibit additional properties such as the ability to sensitize cells, such as cancerous cells, to radiation. Alternatively, chemotherapeutic compounds may be radiation protectants that protect cells, such as non-cancerous cells, from the effects of radiation. Indeed, certain HDAC inhibitors may induce radiation sensitization in target tumor cells while normal cells may be more resistant and are relatively spared or protected from the effects of radiation.

Therapeutic ratios may be determined by measuring the effects of drugs on cancers and on normal tissues. Radiation toxicities to organs at risk may affect normal tissues adjacent to the treated volume (such as rectum or bladder in the treatment of a pelvic tumor), or in sites receiving transit dose (such as the pelvic bone marrow). Others have shown radiation protection of normal cells by HDAC inhibitors.

As described above, certain HDAC inhibitors may indirectly activate ATM and may be used as therapeutic agents to relax chromatin and hence sensitize cells to DNA-damaging drugs and/or radiation. Timely activation and inactivation of ATM are required for efficient repair, and any ATM perturbation may inhibit the ability of cells to resist DNA damage.

Regarding ATM more specifically, ATM is a protein kinase mutated in the human disease ataxia telangiectasia (A-T). ATM has been a focus of investigation because of the unusual radiosensitive phenotype of cells from A-T patients. Because investigating ATM signalling has yielded valuable insights into the DNA damage response, redox signalling, and cancer, ATM has an important role in the repair of radiation-induced DSBs of DNA and potentially of radiation protection of normal tissues. Indeed, ATM activation by DIM mitigates radiation injury in cells and animals.

Accordingly, dual function compounds that inhibit HDAC and activate ATM are beneficial in that they may, for example, sensitize cancerous cells to radiation while simultaneously aiding in the protection of healthy cells and tissues about the cancerous tissues from such radiation. These properties may be in addition to the dual function compound's cytotoxic activity, which may be measured against both cancerous cells and non-cancerous cells.

Regarding immunological diseases, the compounds of the invention may be used in methods of treating diseases that are the result of over-active immunity.

Regarding neurological diseases, millions of people worldwide endure such debilitating diseases that implicate HDAC proteins and may be treated by the compounds of the invention. Neurological diseases affect a vast number of humans of all ages. In the United States, over 500,000 people each year experience a stroke, making it the third leading cause of death and the primary cause of disability. One in twenty people is afflicted with Alzheimer's disease by the age of 65, and almost 40 percent of the population have the disease by age 80. More than 600,000 people suffer from Parkinson's disease and over 200,000 from multiple sclerosis. Every year, greater than 10,000 people die from amyotrophic lateral sclerosis (ALS). The impact of neurological disease is not only devastating for the patients, but also for their families.

Although considerable effort has been invested in the design of effective therapies, neurological diseases continue to threaten the worldwide population and lessen their quality of life. The compounds of the invention may be used in compositions or methods for treating such neurological disorders that implicate HDAC proteins. Specifically, the compounds of the invention may be used in treating stroke, Huntington's disease, spinal muscular atrophy (SMA), Parkinson's disease, Alzheimer's, Multiple Sclerosis, and Amyotrophic Lateral Sclerosis (ALS). In certain aspects, the compounds of the invention may be used in treating Alzheimer's disease and multiple sclerosis.

The present invention provides solutions for treating diseases by providing compounds, compositions, and methods of treatment. When such diseases may include, but are not limited to, cancers and neurological diseases.

As used herein, the terms "treat," "treatment," and/or "treating" may refer to the management of a disease, disorder, or pathological condition (e.g., cancer, neoplastic disorder, immunological disorder, or neurological disorder) with the intent to cure, ameliorate, stabilize, prevent, or control the disease, disorder, pathological condition, or symptoms thereof. Regarding control of the disease, disorder, or pathological condition more specifically, "control" may include the absence of disease progression, as assessed by the response to the methods recited herein, where such response may be complete (e.g., placing the disease in remission) or partial (e.g., slowing the spread of cancerous cells and tissues and/or preventing, slowing, or halting metastasis). The terms "treat," "treatment," and/or "treating" may further encompass, with respect to the treatment of cancer, the sensitization of cancerous cells and tissues (e.g., neoplastic cells and tissues) to radiation and/or the protection of non-cancerous cells from the effects of radiation.

For example, a patient responding to the methods of treatment disclosed in the present invention may exhibit the absence of disease progression (e.g., halting the growth and/or spread of neoplastic cells and tissues) over another patient that does not receive the methods of treatment described herein.

Certain cancers that may be treated by the methods of the invention, with or without additional irradiation, are set forth in Table 1.

TABLE 1

Selected cancers that may be treated by the methods of the invention.

Exemplary Solid Tumors:

acoustic neuroma
adenocarcinoma
angiosarcoma
astrocytoma
basal cell carcinoma
bile duct carcinoma
bladder carcinoma
breast cancer
bronchogenic carcinoma
cervical cancer
chordoma
choriocarcinoma
colon cancer
colorectal cancer
craniopharygioma
cystadenocarcinoma
embryonal carcinoma
endotheliosarcoma
ependymoma
epithelial carcinoma
esophagaelcancer
Ewing's tumor
fibrosarcoma
glioblastomamultiforme
glioma
hemangioblastoma
hepatoma
kidney cancer
leiomyosarcoma
liposarcoma
lung cancer
lymphangioendotheliosarcoma

TABLE 1-continued

Selected cancers that may be treated by the methods of the invention.

lymphangiosarcoma
medullary carcinoma
medulloblastoma
melanoma
meningioma
mesothelioma
myxosarcoma
nasal cancer
neuroblastoma
oligodendroglioma
oral cancer
osteogenic sarcoma
ovarian cancer
pancreatic cancer
papillary adenocarcinomas
papillary carcinoma
pinealoma
prostate cancer
rabdomyosarcoma
renal cell carcinoma
retinoblastoma
sebaceous gland carcinoma
seminoma
skin cancer
squamous cell carcinoma
stomach cancer
sweat gland carcinoma
synovioma
testicular cancer small cell lung carcinoma
throat cancer
uterine cancer
Wilms' tumor

Exemplary Blood Cancers:

acute erythroleukemic leukemia
acute lymphoblastic B-cell leukemia
acute lymphoblastic T-cell leukemia
acute lypmhoblastic leukemia
acute megakaryoblastic leukemia
acute monoblastic leukemia
acute myeloblastic leukemia
acute myelomonocytic leukemia
acute nonlymphocytic leukemia
acute promyelocytic leukemia
acute undifferentiated leukemia
chronic lymphocytic leukemia
chronic myelocytic leukemia
hairy cell leukemia
multiple myeloma

Exemplary Lymphomas:

heavy chain disease
Hodgkin's disease
multiple myeloma
non-Hodgkin's lymphoma
polycythemia vera
Waldenstrom's macroglobulinemia Certain specific cancers that may be treated by methods of the invention include of gastric cancer, prostate cancer, colon cancer, breast cancer, Non-Hodgkin's lymphoma, ovarian cancer, sarcoma, lung cancer, leukemia, myeloma, testicular cancer, cervical cancer, pancreatic cancer, head and neck cancer, rectal cancer, and brain cancer. In certain aspects of the invention, cancer treatment methods may include the application of radiation as described herein.

The immunological disorders that may be treated by the methods of the invention include systemic lupus erythematosus and rheumatoid arthritis.

The neurological disorders that may be treated by methods of the invention include stroke, Huntington's disease, spinal muscular atrophy (SMA), Parkinson's disease, Alzheimer's, Multiple Sclerosis, and Amyotrophic Lateral Sclerosis (ALS).

In determining the biological activity of the compounds of the invention against HDAC and/or ATM or diseases that may be mediated by HDAC and/or ATM (e.g., cancer) as they may be used in methods of the invention, the structure of certain compounds may be compared to an HDAC and/or ATM pharmacophore. As used herein, the term "pharmacophore" refers to the ensemble of steric and electronic features that are necessary to ensure the optimal supramolecular interactions with a specific biological target structure (e.g., HDAC and/or ATM) and to trigger, activate, block, inhibit or modulate the biological target's biological activity, as the case may be. See, IUPAC, *Pure and Applied Chemistry* (1998) 70: 1129-1143.

In comparing the biological activity of the compounds of the invention against HDAC and/or ATM, biological activity may be correlated to the specific structures of the compounds of the invention in the development of a pharmacophore model. As used herein, the term "pharmacophore model" refers to a representation of points in a defined coordinate system wherein a point corresponds to a position or other characteristic of an atom or chemical moiety in a bound conformation of a ligand and/or an interacting polypeptide, protein, or ordered water. An ordered water is an observable water in a model derived from structural determination of a polypeptide or protein. A pharmacophore model can include, for example, atoms of a bound conformation of a ligand, or portion thereof. A pharmacophore model can include both the bound conformations of a ligand, or portion thereof, and one or more atoms that interact with the ligand and are from a bound polypeptide or protein. Thus, in addition to geometric characteristics of a bound conformation of a ligand, a pharmacophore model can indicate other characteristics including, for example, charge or hydrophobicity of an atom or chemical moiety. A pharmacophore model can incorporate internal interactions within the bound conformation of a ligand or interactions between a bound conformation of a ligand and a polypeptide, protein, or other receptor including, for example, van der Waals interactions, hydrogen bonds, ionic bonds, and hydrophobic interactions. A pharmacophore model can be derived from 2 or more bound conformations of a ligand.

The compounds of the invention may be administered as described herein, or in a form from which the active agent can be derived, such as a prodrug. A "prodrug" is a derivative of a compound described herein, the pharmacologic action of which results from the conversion by chemical or metabolic processes in vivo to the active compound. Prodrugs include compounds wherein an amino acid residue, or a polypeptide chain of two or more (e.g., two, three or four) amino acid residues is covalently joined through an amide or ester bond to a free amino, hydroxyl or carboxylic acid group of Formulas I-IV. The amino acid residues include but are not limited to the 20 naturally occurring amino acids commonly designated by one or three letter symbols but also include, for example, 4-hydroxyproline, hydroxylysine, desmosine, isodesmosine, 3-methylhistidine, beta-alanine, gamma-aminobutyric acid, citrulline, homocysteine, homoserine, ornithine and methionine sulfone. Additional types of prodrugs are also encompassed. For instance, free carboxyl groups can be derivatized as amides or alkyl esters. Prodrug esters as employed herein includes esters and carbonates formed by reacting one or more hydroxyls of compounds of the method of the invention with alkyl, alkoxy, or aryl substituted acylating agents employing procedures known to those skilled in the art to generate acetates, pivalates, methylcarbonates, benzoates and the like. As further examples, free hydroxyl groups may be derivatized using groups including but not limited to hemisuccinates, phosphate esters, dimethylaminoacetates, and phosphoryloxymethyloxycarbonyls, as outlined in Advanced Drug Delivery Reviews, 1996, 19, 115. Carbamate prodrugs of hydroxyl and amino groups are also included, as are carbonate prodrugs, sulfonate prodrugs, sulfonate esters and sulfate esters of hydroxyl groups. Free amines can also be derivatized to amides, sulfonamides or phosphonamides. All of the stated prodrug moieties may incorporate groups including but not limited to ether, amine and carboxylic acid functionalities. Moreover, any compound that can be converted in vivo to provide the bioactive agent (e.g., a compound of formula I) is a prodrug within the scope of the invention. Various forms of prodrugs are well known in the art. A comprehensive description of prodrugs and prodrug derivatives are described in: (a) The Practice of Medicinal Chemistry, Camille G. Wermuth et al., Ch 31, (Academic Press, 1996); (b) Design of Prodrugs, edited by H. Bundgaard, (Elsevier, 1985); (c) A Textbook of Drug Design and Development, P. Krogsgaard-Larson and H. Bundgaard, eds., Ch. 5, pgs, 113-191 (Harwood Academic Publishers, 1991).

In general, prodrugs may be designed to improve the penetration of a drug across biological membranes in order to obtain improved drug absorption, to prolong duration of action of a drug (slow release of the parent drug from a prodrug, decreased first-pass metabolism of the drug), to target the drug action (e.g. organ or tumor-targeting, lymphocyte targeting), to modify or improve aqueous solubility of a drug (e.g., i.v. preparations and eyedrops), to improve topical drug delivery (e.g. dermal and ocular drug delivery), to improve the chemical/enzymatic stability of a drug, or to decrease off-target drug effects, and more generally in order to improve the therapeutic efficacy of the compounds utilized in the invention.

A compound used in practicing any method of the invention may be administered in an amount sufficient to induce the desired therapeutic effect in the recipient thereof. Thus the term "therapeutically effective amount" as used herein refers to an amount of a compound of the invention that is sufficient to treat a disease in accordance with the invention by administration of one or more of the compounds of formulas I-IV or a prodrug thereof. In some embodiments, the therapeutically effective amount refers to the amount appropriate to inhibit HDAC and activate ATM in a patient. For example, the term therapeutically effective amount may include the amount of a compound of the invention necessary to detectably sensitize cancerous cells to radiotherapy and detectably protect non-cancerous cells from radiotherapy. In addition, the term therapeutically effective amount may include the amount of a compound necessary, for example, to bring about a detectable therapeutic, preventative, or ameliorative effect in a patient having a disease as set forth herein. The effect may include, for example, the reduction, prevention, amelioration, or stabilization of symptoms or conditions associated with a disease as described herein.

For example, the therapeutically effective amount of a compound of the invention that may sensitize cancerous or neoplastic cells to radiation may be that amount that enhances the inhibitory or damaging effect of radiation on cancer cells by at least 10%, at times by at least 20%, 30%, 40%, 50%, 60%, 70% 80%, 90% and even at times by 99-100% of the inhibitory or damaging effect of the radiation on the cancer cells as compared to the effect of radiation of the same cancerous and/or neoplastic cells, without sensitization.

The compounds and/or compositions of the invention that may sensitize cancerous or neoplastic cells to radiation may be administered in one or more doses, at least a portion thereof being given to the patient prior to the patient's exposure to a radiation. When a treatment schedule involves administration of several doses of the compound and/or composition, the doses may be the same or different, e.g. escalating or de-escalating amounts per administration. In addition, when referring to a radiosensitizing compound it should be understood as also encompassing a combination of such compounds.

The compounds and/or compositions of the invention are applicable for treating disease in any mammal. Exemplary mammals include laboratory animals, including rodents such as mice, rats and guinea pigs; farm animals such as cows, sheep, pigs and goats; pet animals such as dogs and cats; and primates such as monkeys, apes and humans. In one embodiment, the compounds used in the methods of the invention are used in the treatment of humans.

The methods of the invention may include irradiating a selected tissue of the patient before, during, and/or after a compound of the invention (or pharmaceutical composition containing such compound) that may sensitize cancerous or neoplastic cells to radiation and protect healthy, non-cancerous cells and tissues from radiation has been administered to the patient. Regarding the application of radiation ("radiation therapy" or "radiotherapy") to the patient or subject more generally, such therapy may encompass any ionizing radiation known to those having ordinary skill in the art. Generally, radiation therapy, and in particular ionizing radiation includes applying to a selected tissue, such as a selected tissue comprising cancerous and/or neoplastic cells, a dose of ionizing radiation or two or more fractions of ionizing radiation. The ionization radiation is defined as an irradiation dose which is determined according to the disease's characteristics at the selected tissue and therapeutic decision of a physician. The term "fractionated dose(s)" may include, for example, conventional fractionation, hyperfractionation, hypofractionation, and accelerated fractionation). The amount of radiation and doses thereof should be sufficient to damage the highly proliferating cells' genetic material, making it impossible for the irradiated cells to continue growing and dividing.

In certain aspects, fractionated irradiation may vary from daily doses (e.g. one or more times per day) given for a period of weeks, or to once weekly doses given for a period of weeks or months. Indeed, radiation may be applied in dosages of about 0.1 Gy to about 100 Gy. For example, the dosage may be about 5 to 15 Gy.

In certain fractionated irradiation methods, irradiation dosing may include the application of about 0.1 to about 20 Gy or from about 1 Gy to about 10 Gy or from about 1 Gy to about 3 Gy in a single session, which may be repeated several times over the course of about 1 to 10 weeks, or about 2 to 5 weeks. In certain embodiments of the invention, the radiation dose may be about 30 to 60 Gy at 1 to 5 Gy fractions over a period of about 2 to 5 weeks.

In other exemplary aspects, three different fractionation schemes may be used in accordance with the invention.

In one embodiment, radiation doses from 1 Gy to 3 Gy in daily fractions for several weeks (e.g., about 2 to 8 weeks) to achieve cumulative doses of about 20 Gy to 80 Gy.

In another embodiment, large fraction radiation therapy may include doses of 4 Gy to 25 Gy. This fractionated irradiation scheme may include the delivery of about 1 fraction to 5 fractions delivered over about 1-2 weeks. This type of radiation may be referred to as stereotactic radiosurgery or stereotactic body radiation therapy.

In a further embodiment, brachytherapy may be used, which is delivered using low dose and rate techniques or high-dose rate techniques, typically delivering doses of about 4 Gy to 10 Gy per day with technique and fractionation specific to the clinical situation as would be understood by a person having ordinary skill in the art.

As set forth above, the compounds and/or compositions of the invention may be administered before, after, or together with the radiation. One cycle of radiation therapy as well as several cycles of radiation is possible, dependent on the reduction of tumor size or extent of proliferation. Such sequences of radiosensitization treatments and ionizing irradiation are repeated as needed to abate and, optimally, reduce or eliminate the spread of the cancer or neoplastic cells in the tissue or region of tissue that is selected for treatment. Accordingly, the total dose and the radiation regimen will depend, inter glia, on the cancer type, type of compound that results in radiosensitization, irradiated area, physical condition of the patient and many other considerations appreciated by those having ordinary skill in the art.

In addition to the administration of a compound of the invention and the irradiation of the patient, the methods of the invention may include the administration of a therapeutically effective amount of an additional chemotherapeutic agent to the patient. The chemotherapeutic agent may be provided before, during, or after at least one of the steps of administering the radiosensitizing agent and irradiating a selected tissue of the patient. Therefore, the chemotherapeutic agent may be provided at various points during the methods of the invention for the treatment of disease. In certain aspects, the chemotherapeutic agent may be administered concurrently with or after the step of irradiating the selected tissue of the patient.

The compound(s) described herein may also be administered at a dose in range from about 0.01 mg/kg to about 200 mg/kg of body weight per day. A dose of from 0.1 to 100 mg/kg, and from 1 to 30 mg/kg per day in one or more applications per day should be effective to produce the desired result. By way of example, a suitable dose for oral administration would be in the range of 1-30 mg/kg of body weight per day, whereas a typical dose for intravenous administration would be in the range of 1-10 mg/kg of body weight per day. In an exemplary embodiment, the compounds of the invention may be administered at a dose of about 200 mg to 600 mg per day. For example, the compounds of the invention may be administered at a dose of about 400 mg per day.

Of course, as those skilled in the art will appreciate, the dosage actually administered will depend upon the condition being treated, the age, health and weight of the recipient, the type of concurrent treatment, if any, and the frequency of treatment. Moreover, the effective dosage amount may be determined by one skilled in the art on the basis of routine empirical activity testing to measure the bioactivity of the compound(s) in a bioassay, and thus establish the appropriate dosage to be administered.

The compounds used in certain methods of the invention may typically be administered from 1-4 times a day, so as to deliver the above-mentioned daily dosage. However, the exact regimen for administration of the compounds described herein will necessarily be dependent on the needs of the individual subject being treated, the type of treatment administered and the judgment of the attending medical specialist. As used herein, the term "subject" or "patient" includes both humans and animals.

In general, the compounds used in the methods of the invention can be administered to provide radiosensitization as set forth above using any acceptable route known in the art, either alone or in combination with one or more other therapeutic agents. Thus, the compound(s) of the invention can be administered orally, parenterally, such as by intravenous or intraarterial infusion, intramuscular, intraperitoneal, intrathecal or subcutaneous injection, by liposome-mediated delivery, rectally, vaginally, by inhalation or insufflation, transdermally or by otic delivery.

The orally administered dosage unit may be in the form of tablets, caplets, dragees, pills, semisolids, soft or hard gelatin capsules, aqueous or oily solutions, emulsions, suspensions or syrups. Suitable dosage forms for parenteral administration include injectable solutions or suspensions, suppositories, powder formulations, such as microcrystals or aerosol spray. The active agents of the invention may also be incorporated into a conventional transdermal delivery system.

As used herein, the expression "physiologically compatible carrier medium" includes any and all solvents, diluents, or other liquid vehicle, dispersion or suspension aids, surface agent agents, isotonic agents, thickening or emulsifying agents, preservatives, solid binders, lubricants, fillers and the like as suited for the particular dosage form desired. Remington: The Science and Practice of Pharmacy, 20$^{th}$ edition, A. R. Genaro et al., Part 5, Pharmaceutical Manufacturing, pp. 669-1015 (Lippincott Williams & Wilkins, Baltimore, Md./Philadelphia, Pa.) (2000) discloses various carriers used in formulating pharmaceutical compositions and known techniques for the preparation thereof. Except insofar as any conventional pharmaceutical carrier medium is incompatible with either the radiosensitizing or chemotherapeutic compounds used in the present invention, such as by producing an undesirable biological effect or otherwise interacting in an deleterious manner with any other component(s) of a formulation comprising such compounds or agents, its use is contemplated to be within the scope of this invention.

For the production of solid dosage forms, including hard and soft capsules, the agents of the invention may be mixed with pharmaceutically inert, inorganic or organic excipients, such as lactose, sucrose, glucose, gelatine, malt, silica gel, starch or derivatives thereof, talc, stearic acid or its salts, dried skim milk, vegetable, petroleum, animal or synthetic oils, wax, fat, polyols, and the like. For the production of liquid solutions, emulsions or suspensions or syrups one may use excipients such as water, alcohols, aqueous saline, aqueous dextrose, polyols, glycerine, lipids, phospholipids, cyclodextrins, vegetable, petroleum, animal or synthetic oils. For suppositories one may use excipients, such as vegetable, petroleum, animal or synthetic oils, wax, fat and polyols. For aerosol formulations, one may use compressed gases suitable for this purpose, such as oxygen, nitrogen and carbon dioxide. Pharmaceutical compositions or formulations may also contain one or more additives including, without limitation, preservatives, stabilizers, e.g., UV stabilizers, emulsifiers, sweeteners, salts to adjust the osmotic pressure, buffers, coating materials and antioxidants.

The present invention further includes controlled-release, sustained-release, or extended-release therapeutic dosage forms for administration of the compounds of the invention, which involves incorporation of the compounds into a suitable delivery system in the formation of certain compositions. This dosage form controls release of the compound(s) in such a manner that an effective concentration of the compound(s) in the bloodstream may be maintained over an extended period of time, with the concentration in the blood remaining relatively constant, to improve therapeutic results and/or minimize side effects. Additionally, a controlled-release system would provide minimum peak to trough fluctuations in blood plasma levels of the compound.

In pharmaceutical compositions used in practicing the method of the invention, the specified compound(s) may be present in an amount of at least 0.5 and generally not more than 95% by weight, based on the total weight of the composition, including carrier medium and/or supplemental active agent(s), if any. In some embodiments, the proportion of compound(s) varies between 30-90% by weight of the composition.

The methods of the present invention will normally include medical follow-up to determine the therapeutic or prophylactic effect brought about in the subject undergoing treatment with the compound(s) and/or composition(s) described herein.

Specific compounds used in the compositions and methods of the invention include those compounds set forth in FIG. 1. In certain aspects, the compounds of the invention include those compounds set forth in FIG. 2. Certain compounds of the invention include N-(6-(hydroxyamino)-6-oxohexyl)-3-methyl-1H-indole-2-carboxamide (i.e., SP-1-161) and $N^1$-hydroxy-$N^6$-(2-(2-methyl-1H-indol-3-yl) octanediamide (i.e., SP-1-163). In some embodiments, the compounds of the invention include SP-1-161, SP-1-163, SP-1-229, and SP-1-303.

In additional aspects of the methods of the invention, such methods may be used as second or third line methods of treatment for patients where such patients were provided with standard therapies that failed. For example, cisplatin is a first line treatment for head and neck cancers. However, in certain instances, the patient may not respond to cisplatin or simply relapse after a certain period of time. In such instances where the patient relapses, the cancer or neoplastic disorder can be more difficult to treat. The present method can thus provide a second, third, fourth, or even a more subsequent line method of treatment after certain initial methodologies fail or are inadequate.

Furthermore, in certain aspects of the methods of the invention, the compounds of the invention (e.g., Formulas I-IV) may be utilized in combination with one or more other additional therapeutic agents, as necessary. For example, such additional therapeutic agents may include bortezomib and/or dexamethasone.

Where the compounds of the invention are administered in combination with one or more additional therapeutic agents, the additional therapeutic agents may be delivered intravenously (e.g., at a dose from about 0.1 to 10 mg/m$^2$) and/or orally (e.g., at a dose from about 1 to 100 mg). For example, in a specific method of the invention for the treatment of cancer, a compound selected from Formula I could be provided to a patient in need of such treatment. After providing the compound of the invention, the method may further include the administration of bortezomib to the patient in combination with dexamethasone. The administration of these three compounds could be applied in cycles over the course of days or weeks as understood by a person having ordinary skill in the art in order to maximize their combined effect against the cancer being treated. During the cycling of the compound of the invention and the additional therapeutic agents, the method may further include the step of irradiating the patient according to a regimen set forth herein.

For a specific example, a method for treating cancer, such as multiple myeloma, in patient in need thereof may include, in a first phase of the method: providing a compound selected from Formula I to the patient once daily 2 to 4 times per week for about 2 weeks during a first 3 week cycle, then providing bortezomib at a dose of about 1.3 mg/m$^2$ intravenously to the patient twice weekly for about 2 weeks during the 3 week cycle; and then providing dexamethasone to the patient at a dose of about 20 mg orally per day of bortezomib and the day after each dose of bortezomib.

Where the patient demonstrates or achieves a measurable clinical benefit due to the method of the invention, the method of the invention may further include a second phase that comprises: providing the compound selected from Formula I to the patient once daily 2 to 4 times per week for about 2 weeks during a second 3 week cycle; then providing bortezomib at a dose of about 1.3 mg/m$^2$ intravenously to the patient once weekly for 2 weeks during the three week cycle; and then providing dexamethasone to the patient at a dose of about 20 mg orally per day of bortezomib and the day after each dose of bortezomib. In one embodiment, the first phase of the method may include 8 or fewer 3 week cycles. Additionally, the second phase of the method may include 8 or fewer 3 week cycles. Moreover, the method of the invention may include the irradiation of the patient before, after, or during the administration of the compound of the invention as set forth in the first phase of the method or the second phase of the method. Such radiation may be applied as described herein.

The following examples describe the invention in further detail. These examples are provided for illustrative purposes only, and should in no way be considered as limiting the invention.

EXAMPLES

Example 1

Figure 2:
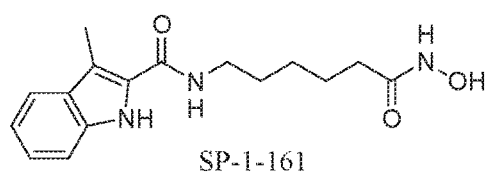
FIG. 2 schematically illustrates certain selected embodiments of Formula I.
Figure 2:
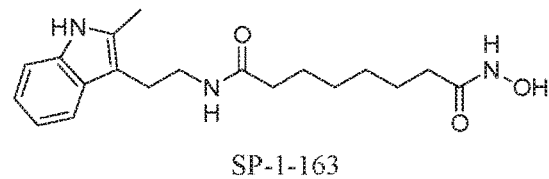
Figure 2:
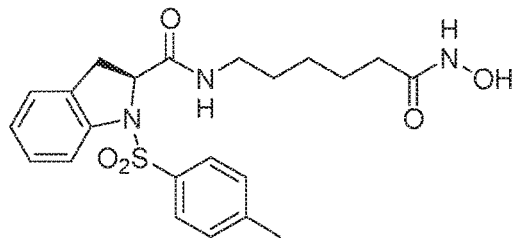
Figure 2:
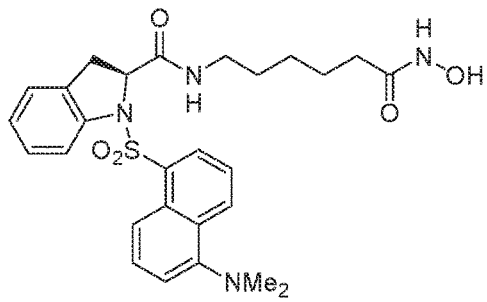
Figure 2:
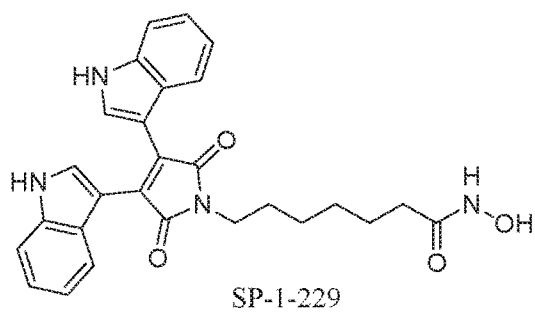
Figure 2:
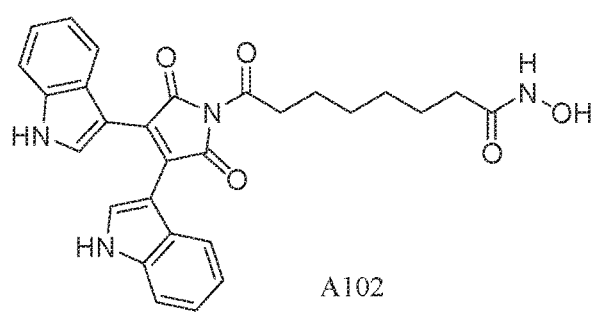
Figure 2:
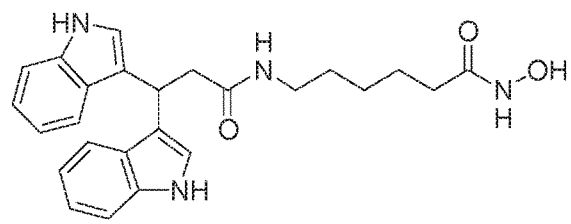
Figure 2:
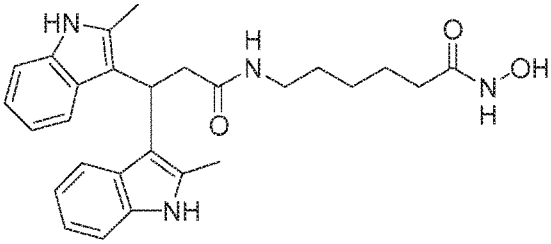
Figure 2:
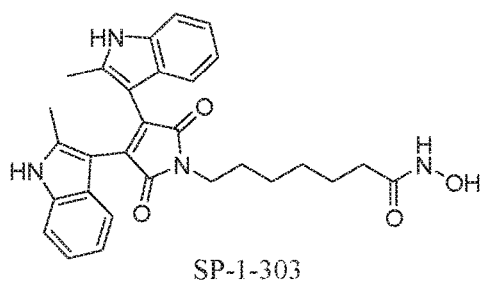

Synthesis of N-(6-(hydroxyamino)-6-oxohexyl)-3-methyl-1H-indole-2-carboxamide (see FIGS. 1 and 2)

In a first step, we prepared the intermediate methyl 6-(3-methyl-1H-indole-2-carboxamido)hexanoate. Triethylamine (1.73 g, 17.1 mmol) was added to a solution of 3-methyl-1H-indole-2-carboxylic acid (300 mg, 1.71 mmol) in dimethyl formamide (DMF) and the solution was cooled to 0° C. using an ice bath. PyBop (1.337 g, 2.57 mmol) was added and the solution was allowed to stir for 15 minutes after which methyl-6-amino hexanoate HCl (311 mg, 1.71 mmol) was added. The solution was allowed to stir overnight while warming to room temperature. DMF was then removed under reduced pressure and the remaining residue was taken up in ethyl acetate (EtOAc), and the organic solution was successively washed with brine and a saturated LiCl solution. The organic portion was then evaporated and the residue was purified via column chromatography using Hexanes:EtOAc to yield 413.4 mg of a tan solid (80% yield).

Characterization of methyl 6-(3-methyl-1H-indole-2-carboxamido)hexanoate: $^1$HNMR, Cl$_3$CD, 400 MHz δ: 9.19 (1H, s-br), 7.61 (1H, d), 7.37 (1H, d), 7.27 (1H, t), 7.13 (1H, t), 3.66 (3H, s), 3.53 (2H, m), 2.57 (3H, s), 1.69 (4H, m), 1.45 (2H, m), 1.27 (2H, m). $^{13}$CNMR, Cl$_3$CD, 60 MHz, δ: 174.16, 155.07, 148.22, 128.71, 124.67, 120.00, 119.83, 111.69, 51.51, 33.80, 31.55, 29.37, 26.35, 24.40, 14.07.

We then prepared the N-(6-(hydroxyamino)-6-oxohexyl)-3-methyl-1H-indole-2-carboxamide product from the hexanoate intermediate. 4.5 ml of hydroxylamine (50% solution in H$_2$O) was added to a solution of methyl 6-(3-methyl-1H-indole-2-carboxamido)hexanoate (413 mg, 1.37 mmol) in methanol and the solution was heated to 60° C. overnight. The reaction was quenched with the addition of acetone and the solvent and acetone oxime were removed under reduced pressure. The remaining residue was purified via column using EtOAc:MeOH to yield a tan solid (257 mg, 62%).

Characterization of N-(6-(hydroxyamino)-6-oxohexyl)-3-methyl-1H-indole-2-carboxamide: $^1$HNMR, DMSO-d$_6$, 400 MHz δ: 11.32 (1H, s), 10.37 (1H, s), 8.67 (1H, s-br), 7.99 (1H, s), 7.54 (1H, d), 7.34 (1H, d), 7.16 (1H, t), 7.00 (1H, t), 3.25 (2H, m), 2.47 (3H, s), 1.95 (2H, m), 1.52 (4H, m), 1.30 (2H, m). $^{13}$CNMR, DMSO-d$_6$, 60 MHz, δ: 169.59, 162.33, 135.71, 128.45, 128.18, 124.02, 120.01, 119.34, 113.94, 112.21, 39.14, 32.68, 29.34, 26.57, 25.35, 10.12.

Example 2

Synthesis of N$^1$-hydroxy-N$^6$-(2-(2-methyl-1H-indol-3-yl)ethyl)octanediamide (see FIG. 1)

In a first step, we prepared the methyl 8-((2-(2-methyl-1H-indol-3-yl)ethyl)amino)-8-oxooctanoate intermediate. A solution of 2-(2-methyl-1H-indol-3-yl)ethylamine (252 mg, 1.45 mmol) in dichloromethane (DCM) was added dropwise to a solution of methyl 8-chloro-8-oxooctanoate (300 mg, 1.45 mmol) and solid K$_2$CO$_3$ in DCM and the mixture was allowed to stir for 2 hours. Once the reaction was completed as determined by thin layer chromatography (TLC), the reaction was quenched with the addition of 1M sulfuric acid until the pH became slightly acidic. The solution was the extracted once with water followed by brine after which the organic layers were dried over sodium sulfate. The solvent was then removed via vacuum and the residue was purified over a column using 0-50% EtOAc in Hexanes to yield 338.7 mg (68%).

Characterization of methyl 8-((2-(2-methyl-1H-indol-3-yl)ethyl)amino)-8-oxooctanoate: $^1$HNMR, Cl$_3$CD, 400 MHz δ: 8.22 (1H, s-br), 7.47 (1H, d), 7.26 (1H, d), 7.08 (2H, m), 5.63 (1H, s-br), 3.66 (3H, s), 3.50 (2H, q), 2.90 (2H, t), 2.36 (3H, s), 2.27 (2H, t), 2.06 (2H, t), 1.56 (4H, m), 1.26 (4H, m). $^{13}$CNMR, Cl$_3$CD, 60 MHz, δ: 174.28, 173.08, 135.35, 132.03, 128.61, 121.06, 119.28, 117.70, 110.39, 108.31, 51.46, 39.91, 36.60, 33.94, 28.80, 28.75, 25.41, 24.68, 24.12, 11.58.

We then prepared the N$^1$-hydroxy-N$^6$-(2-(2-methyl-1H-indol-3-yl)ethyl)octanediamide product from the octanoate intermediate. 3 ml of hydroxylamine (50% solution in H$_2$O) was added to a solution of methyl 8-((2-(2-methyl-1H-indol-3-yl)ethyl)amino)-8-oxooctanoate (338.7 mg, 0.98 mmol) in methanol and the solution was heated to 60° C. overnight. The reaction was quenched with the addition of acetone and the solvent and acetone oxime were removed under reduced pressure. The remaining residue was purified via column using EtOAc:MeOH to yield a white solid (182 mg, 54%).

Characterization of N$^1$-hydroxy-N$^6$-(2-(2-methyl-1H-indol-3-yl)ethyl)octanediamide: $^1$HNMR, DMSO-d$_6$, 400 MHz δ: 10.68 (1H, s), 10.35 (1H, s), 8.66 (1H, s-br), 7.83 (1H, s), 7.41 (1H, d), 7.22 (1H, d), 6.94 (2H, m), 3.19 (2H, q), 2.74 (2H, t), 2.30 (3H, s), 2.03 (2H, t), 1.94 (2H, t), 1.47 (4H, m), 1.22 (4H, m).

$^{13}$CNMR, DMSO-d$_6$, 60 MHz, δ: 172.41, 166.64, 135.65, 132.46, 128.79, 120.30, 118.48, 117.73, 110.78, 108.12, 40.06, 35.91, 32.71, 28.91, 28.86, 25.59, 25.48, 24.72, 11.63.

Example 3

Synthesis of (S)—N-(6-(hydroxyamino)-6-oxohexyl)-1-tosylindoline-2-carboxamide (see FIG. 2)

In a first step, we prepared the intermediate (S)-1-tosylindoline-2-carboxylic acid. p-Toluene sulfonyl chloride (1.17 g, 6.13 mmol) was added to a stirred solution of (s)-(–)-indoline-2-carboxylic acid (1 g, 6.13 mmol) with K$_2$CO$_3$ in DCM. The mixture was allowed to stir overnight and was quenched with the addition of 1M sulfuric acid. The solution was then extracted with 1M sulfuric acid and the organic layers were dried over sodium sulfate. After filtration, the solvent was evaporated and the residue was purified over a column using 0-10% MeOH in DCM yielding 852 mg of a sticky oil (44%).

Characterization of (S)-1-tosylindoline-2-carboxylic acid: $^1$HNMR, DMSO-d$_6$, 400 MHz δ: 7.64 (2H, d), 7.43 (1H, d), 7.31 (2H, d), 7.18 (1H, t), 7.07 (1H, d), 6.97 (1H, t), 4.70 (1H, dd), 3.03 (1H, dd), 2.87 (1H, dd), 2.30 (3H, s).

We then prepared a(S)-methyl 6-(1-tosylindoline-2-carboxamido)hexanoate intermediate from the carboxylic acid. Triethylamine (1.73 g, 17.1 mmol) was added to a solution of (S)-1-tosylindoline-2-carboxylic acid (524.8 mg, 1.65 mmol) in DMF and the solution was cooled to 0° C. using an ice bath. PyBop (1.29 g, 2.48 mmol) was added to the solution and allowed to stir for 15 minutes after which methyl-6-amino hexanoate HCl (300 mg, 1.65 mmol) was added. The solution was allowed to stir overnight while warming to room temperature. DMF was then removed under reduced pressure and the remaining residue was taken up in EtOAc, and the organic portion was washed successively with brine and a saturated LiCl solution. The organic layer was then evaporated and the residue was purified via column chromatography using Hexanes:EtOAc to yield 498.8 mg of an oil (68% yield).

Characterization of (S)-methyl 6-(1-tosylindoline-2-carboxamido)hexanoate: $^1$HNMR, Cl$_3$CD, 400 MHz δ: 9.19 (1H, s), 7.64 (2H, d), 7.43 (1H, d), 7.31 (2H, d), 7.18 (1H, t), 7.07 (1H, d), 6.97 (1H, t), 4.70 (1H, dd), 3.66 (3H, s), 3.09 (2H, m), 3.03 (1H, dd), 2.87 (1H, dd), 2.30 (3H, s), 1.92 (2H, t), 1.47 (2H, m), 1.40 (2H, m), 1.23 (2H, m).

We then prepared the(S)—N-(6-(hydroxyamino)-6-oxohexyl)-1-tosylindoline-2-carboxamide product from hexanoate intermediate. 4.5 ml of hydroxylamine (50% solution in H$_2$O) was added to a solution of (S)-methyl 6-(1-tosylindoline-2-carboxamido)hexanoate (498 mg, 1.12 mmol) in methanol and the solution was heated to 60° C. overnight. The reaction was quenched with the addition of acetone and the solvent and acetone oxime were removed under reduced pressure. The remaining residue was purified via column using EtOAc:MeOH to yield a clear oil (219.5 mg, 44%).

Characterization of (S)—N-(6-(hydroxyamino)-6-oxohexyl)-1-tosylindoline-2-carboxamide: $^1$HNMR, DMSO-d$_6$, 400 MHz δ: 10.33 (1H, s), 8.64 (1H, s-br), 8.07 (1H, t), 7.64 (2H, d), 7.43 (1H, d), 7.31 (2H, d), 7.18 (1H, t), 7.07 (1H, d), 6.97 (1H, t), 4.70 (1H, dd), 3.09 (2H, m), 3.03 (1H, dd), 2.87 (1H, dd), 2.30 (3H, s), 1.92 (2H, t), 1.47 (2H, m), 1.40 (2H, m), 1.23 (2H, m). $^{13}$CNMR, DMSO-d$_6$, 60 MHz, δ: 170.56, 169.55, 144.40, 141.17, 133.85, 130.92, 129.82, 127.56, 127.19, 125.11, 124.34, 115.35, 62.80, 38.60, 36.43, 33.06, 26.57, 25.35, 20.94, 14.05.

Example 4

Synthesis of (S)-1-((5-(dimethylamino)naphthalene-1-yl)sulfonyl)-N-(6-(hydroxyamino)-6-oxoheyl)indoline-carboxamide (see FIG. 2)

In a first step, we prepared (S)-1-((5-(dimethylamino)naphthalene-1-yl)sulfonyl)indoline-2-carboxylic acid. Dansyl chloride (1.65 g, 6.13 mmol) was added to a stirred solution of (s)-(-)-indoline-2-carboxylic acid (1 g, 6.13 mmol) with $K_2CO_3$ in DCM. The mixture was allowed to stir overnight and was quenched with the addition of 1M sulfuric acid. The solution was then extracted with 1M sulfuric acid and the organic layers were dried over sodium sulfate. After filtration, the solvent was evaporated and the residue was purified over a column using 0-10% MeOH in DCM yielding 1.28 g of a yellow solid (53%).

Characterization of prepared (S)-1-((5-(dimethylamino)naphthalene-1-yl)sulfonyl)indoline-2-carboxylic acid: $^1$HNMR, DMSO-$d_6$, 400 MHz δ: 13.23 (1H, s-br), 8.44 (1H, d), 8.19 (1H, d), 8.16 (1H, d), 7.56 (2H, m), 7.21 (1H, d), 7.13 (3H, m), 6.92 (1H, t), 5.06 (1H, dd), 3.36 (1H, dd), 3.07 (1H, dd), 2.77 (6H, s).

We then prepared the(S)-methyl 6-(1-((5-(dimethylamino)naphthalene-1-yl)sulfonyl)indoline-2-carboxamido)hexanoate intermediate from the carboxylic acid. Triethylamine (1.27 g, 12.6 mmol) was added to a solution of (S)-1-((5-(dimethylamino)naphthalene-1-yl)sulfonyl)indoline-2-carboxylic acid (500 mg, 1.26 mmol) in DMF and the solution was cooled to 0° C. using an ice bath. PyBop (984.4 mg, 1.85 mmol) was added to the solution and allowed to stir for 15 minutes after which methyl-6-amino hexanoate HCl (228.9 mg, 1.26 mmol) was added. The solution was allowed to stir overnight while warming to room temperature. DMF was then removed under reduced pressure and the remaining residue was taken up in EtOAc, the organic portion was washed successively with brine and a saturated LiCl solution. The organic layer was then evaporated and the residue was purified via column chromatography using Hexanes:EtOAc to yield 475 mg of a yellow oil (72% yield).

Characterization of (S)-methyl 6-(1-((5-(dimethylamino)naphthalene-1-yl)sulfonyl)indoline-2-carboxamido)hexanoate: $^1$HNMR, Cl$_3$CD, 400 MHz δ: 9.19 (1H, s) 8.44 (1H, d), 8.19 (1H, d), 8.16 (1H, d), 7.56 (2H, m), 7.21 (1H, d), 7.13 (3H, m), 6.92 (1H, t), 5.06 (1H, dd), 3.66 (3H, s), 3.36 (1H, dd), 3.09 (2H, m), 3.07 (1H, dd), 2.77 (6H, s), 1.92 (2H, t), 1.47 (2H, m), 1.40 (2H, m), 1.23 (2H, m).

We then prepared the (S)-1-((5-(dimethylamino)naphthalene-1-yl)sulfonyl)-N-(6-(hydroxyamino)-6-oxoheyl)indoline-carboxamide product from the hexanoate. 4.5 ml of hydroxylamine (50% solution in $H_2O$) was added to a solution of (S)-methyl 6-(1-((5-(dimethylamino)naphthalene-1-yl)sulfonyl)indoline-2-carboxamido)hexanoate (475 mg, 0.905 mmol) in methanol and the solution was heated to 60° C. overnight. The reaction was quenched with the addition of acetone and the solvent and acetone oxime were removed under reduced pressure. The remaining residue was purified via column using EtOAc:MeOH to yield a yellow oil (270 mg, 52%).

Characterization of (S)-1-((5-(dimethylamino)naphthalene-1-yl)sulfonyl)-N-(6-(hydroxyamino)-6-oxoheyl)indoline-carboxamide: $^1$HNMR, DMSO-$d_6$, 400 MHz δ: 10.29 (1H, s), 8.64 (1H, s-br), 8.45 (1H, d), 8.18 (1H, d), 8.12 (1H, d), 8.00 (1H, s), 7.59 (1H, t), 7.47 (1H, t), 7.27 (1H, t), 7.20 (1H, d), 7.14 (1H, t), 7.08 (1H, t), 6.96 (1H, t), 4.88 (1H, dd), 3.09 (2H, m), 3.03 (1H, dd), 2.87 (1H, dd), 2.77 (6H, s), 1.92 (2H, t), 1.47 (2H, m), 1.40 (2H, m), 1.23 (2H, m). $^{13}$CNMR, DMSO-$d_6$, 60 MHz, δ: 174.44, 170.11, 151.34, 144.40, 143.37, 133.02, 129.82, 128.34, 127.96, 127.19, 126.35, 125.11, 124.91, 124.34, 123.77, 119.93, 117.61, 115.35, 62.80, 46.23, 38.60, 36.43, 33.06, 26.57, 25.35, 14.05.

Example 5

Figures 3A, 3B:
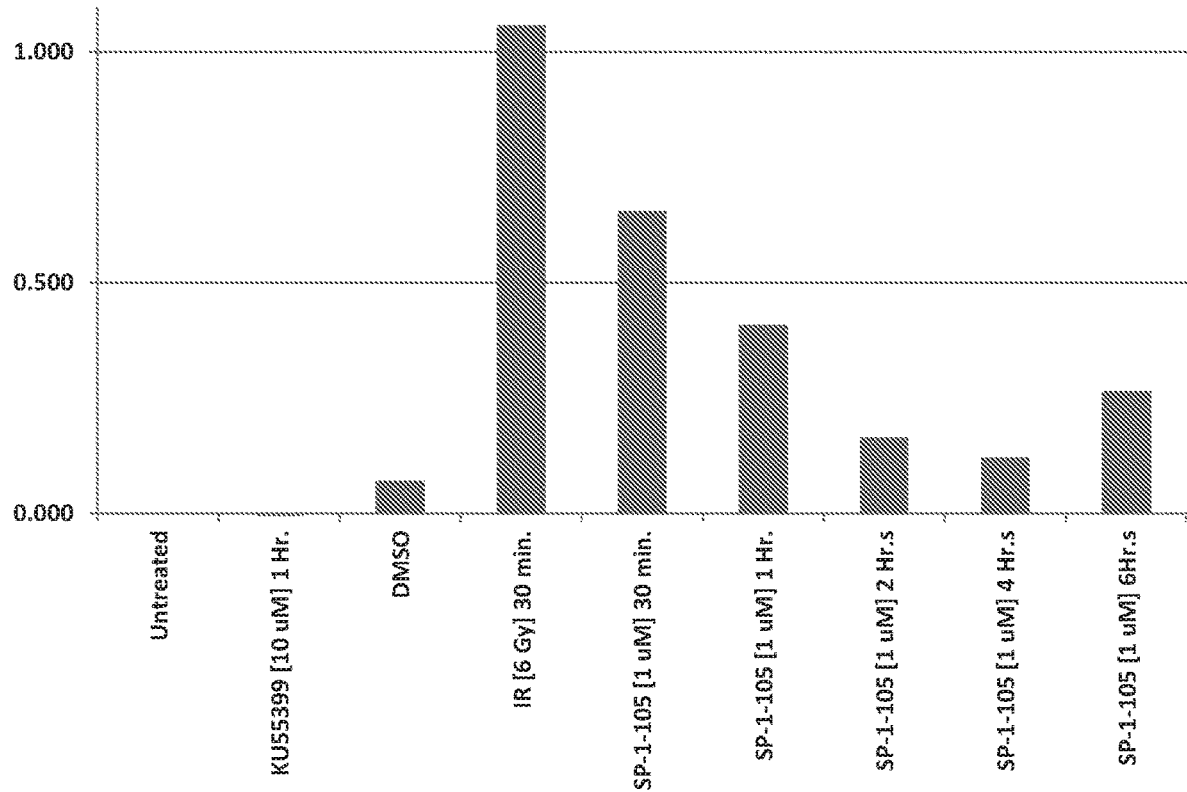
FIGS. 3A and 3B demonstrate the activity of N-(6-(carboxy)-6-oxohexyl)-1H-indole-2-carboxamide (SP-1-105) as an activator of ATM. The activity data is demonstrated in tabular form (FIG. 3A) and graphical form (FIG. 3B). The ATM activity was determined by examining the fold change in phospho-ATM in MCF7 cells.

Activity of N-(6-(carboxy)-6-oxohexyl)-1H-indole-2-carboxamide (SP-1-105) as an Activator of ATM (see FIGS. 3A and 3B)

Several assays were utilized to determine the ability of the compounds of the invention to activate ATM over a period of time. ATM activation may be demonstrated by phosphorylation of ATM (i.e., phosphor-ATM) in the MCF-7 cell line. The fold change in phospho-ATM was measured over a period of time. Accordingly, the increase in phospho-ATM indicates activation of ATM by the compounds of the invention.

In certain examples, the activity of the compounds of the invention was compared to additional modulators of ATM, such as KU55399 (a specific ATM inhibitor); dimethylsulfoxide (DMSO) (a solvent); 3,3'-diindolylmethane (DIM) (an ATM activator); and irradiation (irradiation may result in the generation of phospho-ATM due to DNA damage). DIM was not used as a comparative compound in Example 5.

Materials: MCF7 Cells; Complete RPMI media: RPMI, 10% Fetal Bovine Serum (FBS), 5% L-glutamine, 5% Pen/Strep; R&D Systems Human P-ATM (S1981) DuoSet IC ELISA Assay Kit; Plate sealers; Normal mouse serum (heat inactivated 56 C for 30 min); 96-well ELISA microtiter plate; 450 nm Plate Reader; 60 mm dishes; Disposable pipettes; Pipet-aid; Pipette tips; Micro-pipetter; Cell scraper; Distilled water; Pierce NE-PER Nuclear and Cytoplasmic Extraction Reagent; Pierce Protease and Phosphatase Inhibitor Mini Tablets; KU-55933; DIM (not used in Example 5); Dimethyl sulfoxide (DMSO); Phosphate buffered saline (PBS); and Sterile micro-tubes and conical tubes; Hemocytometer; Microscope; Micro-centrifuge.

MCF7 Cells were grown in Complete RPMI media and $10^6$ cells were seeded into 60 mm dishes. Dishes were then divided into duplicate treatments the following day. Control samples were treated with 3 ml RPMI media for 1 hr. Vehicle samples were treated with 3 ml RPMI media plus 0.1% DMSO for 1 hr. Negative control samples were treated with 10 μM KU-55933 in 3 ml RPMI media plus 0.1% DMSO for 1 Hr. Positive control samples were treated with 0.5 μM DIM in 3 ml RPMI media plus 0.1% DMSO for 30 min. Test Samples were treated with 1 μM of the test compounds (e.g. N-(6-(hydroxyamino)-6-oxohexyl)-1H-indole-2-carboxamide in Example 5) in 3 ml RPMI media plus 0.1% DMSO for 30 min; 1 hr; 2 hrs; 4 hrs; and 6 hrs. At their designated time, samples were harvested on ice using a cell scraper and two washes of 1 ml PBS and kept as a cell pellet on dry ice until all were collected. After all samples were collected they were thawed on ice and separated into cytosolic and nuclear fractions using the Pierce NE-PER Nuclear and Cytoplasmic Extraction Reagent kit with added Pierce protease and phosphotase inhibitor tablet.

After recovery of the separate fractions, the process further included washing cells by suspending the cell pellet with PBS. 1-10×106 cells were transferred to a 1.5 mL microcentrifuge tube and a pellet was formed by centrifugation at 500×g for 2-3 minutes. 100 μL of ice-cold CER I was added to the cell pellet. The tube was vortexed vigorously on the highest setting for 15 seconds to fully suspend the cell pellet and incubate the tube on ice for 10 minutes.

5.5 μL of ice-cold CER II was added to the tube. The tube was vortexed for 5 seconds on the highest setting and the tube was incubated on ice for 1 minute. The tube was vortexed for 5 seconds on the highest setting and centrifuged for 5 minutes at maximum speed in a microcentrifuge (16,000×g). The supernatants were used as the cytoplasmic fraction and were discarded. The insoluble (pellet) fraction, which contains nuclei, was then suspended in 50 μL of ice-cold NER. The fraction was vortexed on the highest setting for 15 seconds and the samples were placed on ice and vortexing continued for 15 seconds every 10 minutes, for a total of 40 minutes. The tubes were centrifuged at maximum speed (16,000×g) for 10 minutes. The nuclear fraction supernatants were placed on ice until used in the R&D Systems Human Phospho-ATM (S1981) DuoSet IC ELISA Assay Kit.

Turning to the ELISA kit, the following steps were used in accordance with the instructions.

Plate Preparation. The Capture Antibody was diluted to a working concentration 10.0 μg/ml in PBS without carrier protein. Immediately coat a 96-well microplate with 100 μL per well of the diluted Capture Antibody. The plate was sealed and incubated overnight at room temperature. Each well was aspirated and washed with Wash Buffer, with the process repeated two times for a total of 3 washes. The wells were washed by filling each well with Wash Buffer (400 μL). After the last wash, any remaining Wash Buffer was removed by aspirating. The plates were blocked by adding 300 μL of Block Buffer to each well. The plates were then incubated at room temperature for 2 hours. The aspiration/wash cycle was repeated. The plates were then ready for sample addition.

Proceeding with sample addition, a Phospho-ATM Standard was prepared by reconstituting with 500 μL of IC Diluent #4. A seven point curve was developed using 2-fold serial dilutions in IC Diluent #4 and a high standard of 200 ng/mL was used to make the standard curve. 100 μL of standard was added per well of plate. 50 μL of sample mixed with 50 μL of IC diluents #4 was added per well of the plate. The IC Diluent #4 was used as the blank. A plate sealer was used to cover the plate and the plate was then incubated for 2 hours at room temperature. The aspiration/wash cycle was repeated as described above for Plate Preparation. Immediately before use, the Detection Antibody was diluted to 200 ng/ml in IC Diluent #1 that contained 2% heat-inactivated normal mouse serum. Only as much Detection Antibody was prepared as required to run each assay. The diluted Detection Antibody was allowed to sit 2 hours before use. 100 μL of the diluted Detection Antibody was added to each well. The plate was covered with a new plate sealer and incubated 2 hours at room temperature. The aspiration/wash cycle was repeated as described above for Plate Preparation. Immediately before use, Streptavidin-HRP was diluted to the working concentration specified on the vial label using IC Diluent #1. 100 μL of the diluted Streptavidin-HRP was added to each well. The plates were incubated for 20 minutes at room temperature. Placing the plate in direct light was avoided. The aspiration/wash step was repeated as described above. 100 μL of Substrate Solution was added to each well. The plates were incubated for 20 minutes at room temperature. Placing the plate in direct light was avoided. 50 μL of Stop Solution was then added to each well. The plate was gently tapped to ensure thorough mixing. The optical density of each well was determined immediately, using a microplate reader set to 450 nm. Where wavelength correction was available, it was set to 540 nm or 570 nm. Experimental samples were compared to controls and the standard curve.

The results of these ATM activation studies are set forth in FIGS. 3A and 3B where a concentration of 1 μM N-(6-(hydroxyamino)-6-oxohexyl)-1H-indole-2-carboxamide was used over a time course of 6 hours. The compound N-(6-(hydroxyamino)-6-oxohexyl)-1H-indole-2-carboxamide was compared to KU55399, DMSO, and radiation (irradiation of the MCF7 cells at 6 Gy).

Example 6

Figures 4A, 4B:
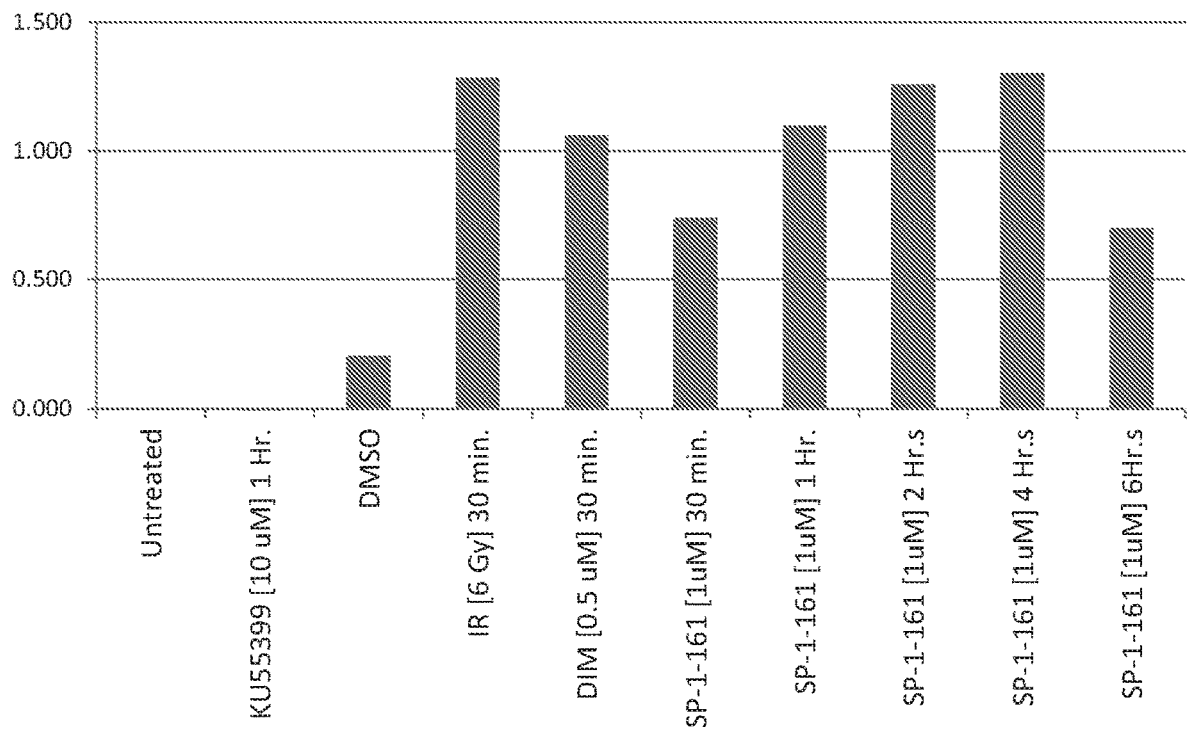
FIGS. 4A and 4B demonstrate the activity of N-(6-(hydroxyamino)-6-oxohexyl)-3-methyl-1H-indole-2-carboxamide (SP-1-161) as an activator of ATM. The activity data is demonstrated in tabular form (FIG. 4A) and graphical form (FIG. 4B). The ATM activity was determined by examining the fold change in phospho-ATM in MCF7 cells.

Activity of N-(6-(hydroxyamino)-6-oxohexyl)-3-methyl-1H-indole-2-carboxamide (SP-1-161) as an Activator of ATM (see FIGS. 4A and 4B)

The activity of N-(6-(hydroxyamino)-6-oxohexyl)-3-methyl-1H-indole-2-carboxamide as an activator of ATM in MCF7 cells was determined as set forth in Example 5. Moreover, the activity of N-(6-(hydroxyamino)-6-oxohexyl)-3-methyl-1H-indole-2-carboxamide was compared to DIM.

The results of these studies are set forth in FIGS. 4A and 4B where a concentration of 1 μM N-(6-(hydroxyamino)-6-oxohexyl)-3-methyl-1H-indole-2-carboxamide was used over a time course of 6 hours. The compound N-(6-(hydroxyamino)-6-oxohexyl)-3-methyl-1H-indole-2-carboxamide was compared to KU55399, DMSO, DIM, and radiation (irradiation of the MCF7 cells at 6 Gy).

Example 7

Figures 5A, 5B:
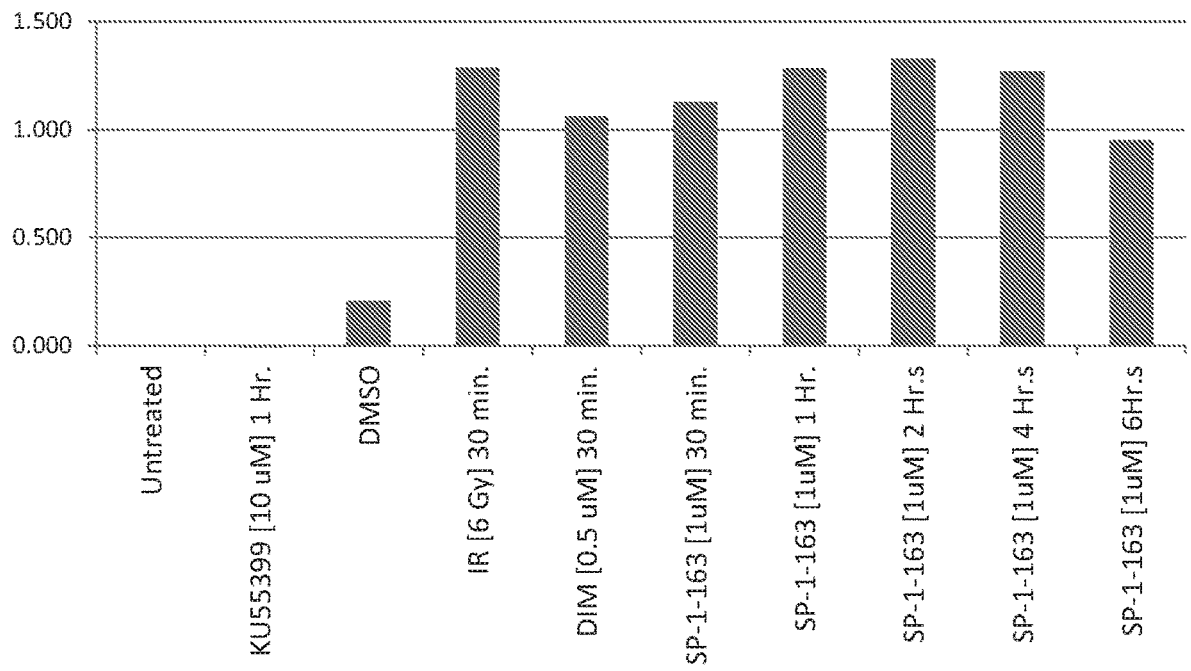
FIGS. 5A and 5B demonstrate the activity of $N^1$-hydroxy-$N^6$-(2-(2-methyl-1H-indol-3-yl)ethyl)octanediamide (SP-1-163) as an activator of ATM. The activity data is demonstrated in tabular form (FIG. 5A) and graphical form (FIG. 5B). The ATM activity was determined by examining the fold change in phospho-ATM in MCF7 cells.

Activity of $N^1$-hydroxy-$N^6$-(2-(2-methyl-1H-indol-3-yl)ethyl)octanediamide (SP-1-163) as an Activator of ATM (FIGS. 5A and 5B)

The activity of $N^1$-hydroxy-$N^6$-(2-(2-methyl-1H-indol-3-yl)ethyl)octanediamide as an activator of ATM in MCF7 cells was determined as set forth in Example 5. Moreover, the activity of $N^1$-hydroxy-$N^6$-(2-(2-methyl-1H-indol-3-yl)ethyl)octanediamide was compared to DIM.

The results of these studies are set forth in FIGS. 5A and 5B where a concentration of 1 μM$N^1$-hydroxy-$N^6$-(2-(2-methyl-1H-indol-3-yl)ethyl)octanediamide was used over a time course of 6 hours. The compound $N^1$-hydroxy-$N^6$-(2-(2-methyl-1H-indol-3-yl)ethyl)octanediamide was compared to KU55399, DMSO, DIM, and radiation (irradiation of the MCF7 cells at 6 Gy).

Example 8

Figures 6A, 6B:
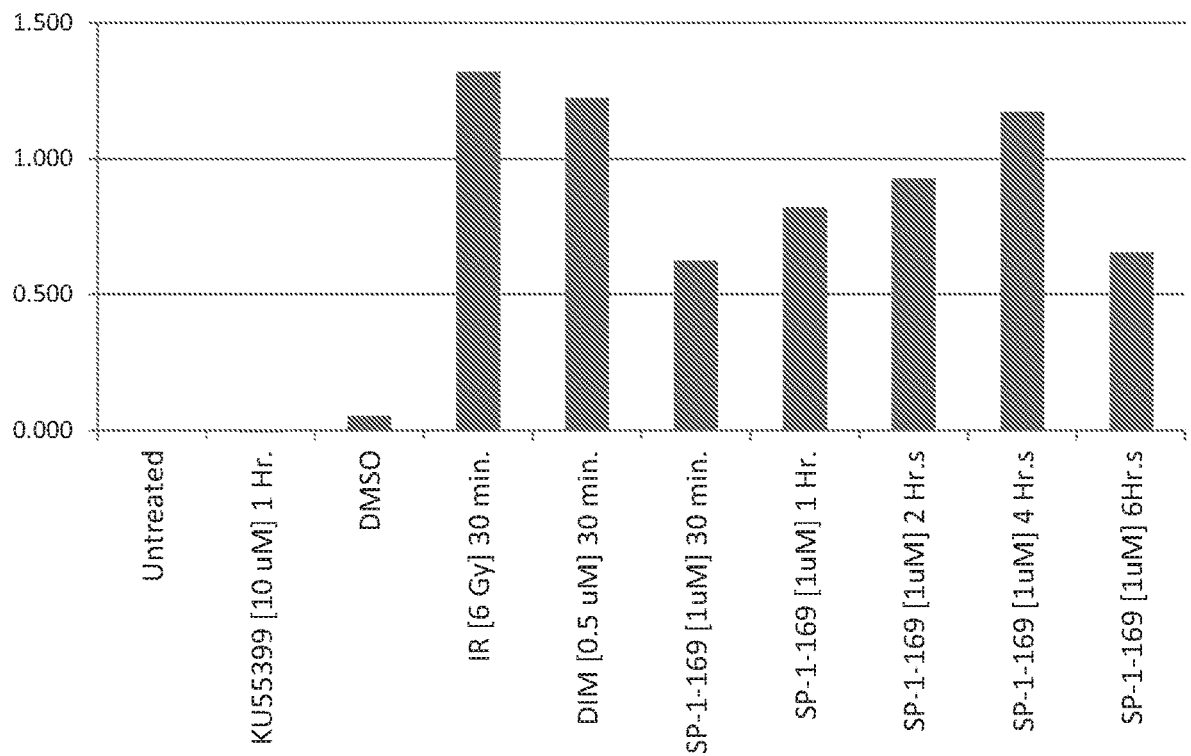
FIGS. 6A and 6B demonstrate the activity of (S)—N-(6-(hydroxyamino)-6-oxohexyl)-1-tosylindoline-2-carboxamide (SP-1-169) as an activator of ATM. The activity data is demonstrated in tabular form (FIG. 6A) and graphical form (FIG. 6B). The ATM activity was determined by examining the fold change in phospho-ATM in MCF7 cells.

Activity of (S)—N-(6-(hydroxyamino)-6-oxohexyl)-1-tosylindoline-2-carboxamide (SP-1-169) as an Activator of ATM (FIGS. 6A and 6B)

The activity of (S)—N-(6-(hydroxyamino)-6-oxohexyl)-1-tosylindoline-2-carboxamide as an activator of ATM in MCF7 cells was determined as set forth in Example 5. Moreover, the activity of (S)—N-(6-(hydroxyamino)-6-oxohexyl)-1-tosylindoline-2-carboxamide was compared to DIM.

The results of these studies are set forth in FIGS. 6A and 6B where a concentration of 1 μM (S)—N-(6-(hydroxyamino)-6-oxohexyl)-1-tosylindoline-2-carboxamide was used over a time course of 6 hours. The compound (S)—N-(6-(hydroxyamino)-6-oxohexyl)-1-tosylindoline-2-carboxamide was compared to KU55399, DMSO, DIM, and radiation (irradiation of the MCF7 cells at 6 Gy).

Example 9

Figures 7A, 7B:
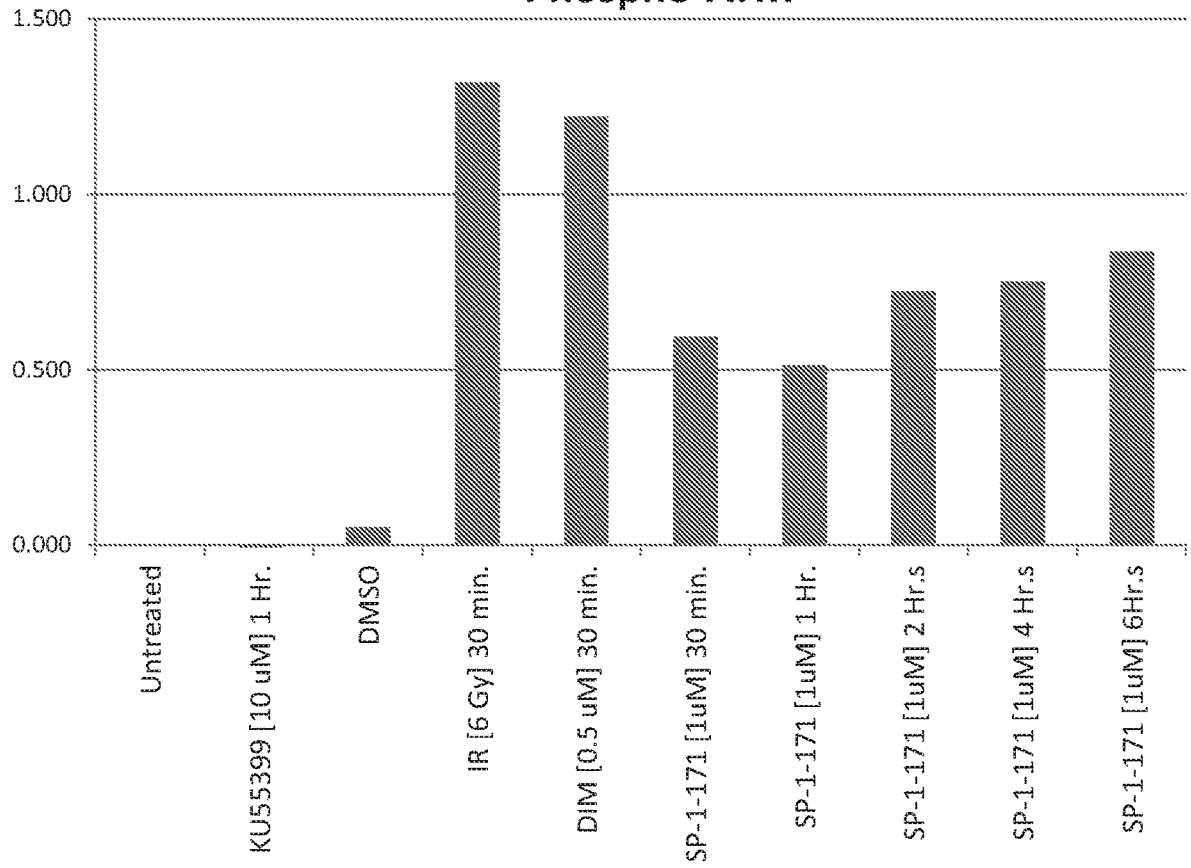
FIGS. 7A and 7B demonstrate the activity of (S)-1-((5-(dimethylamino)naphthalene-1-yl)sulfonyl)-N-(6-(hydroxyamino)-6-oxoheyl)indoline-carboxamide (SP-1-171) as an activator of ATM. The activity data is demonstrated in tabular form (FIG. 7A) and graphical form (FIG. 7B). The ATM activity was determined by examining the fold change in phospho-ATM in MCF7 cells.

Activity of (S)-1-((5-(dimethylamino)naphthalene-1-yl)sulfonyl)-N-(6-(hydroxyamino)-6-oxoheyl)indoline-carboxamide (SP-1-171) as an Activator of ATM (FIGS. 7A and 7B)

The activity of (S)-1-((5-(dimethylamino)naphthalene-1-yl)sulfonyl)-N-(6-(hydroxyamino)-6-oxoheyl)indoline-carboxamide as an activator of ATM in MCF7 cells was determined as set forth in Example 5. Moreover, the activity of (S)-1-((5-(dimethylamino)naphthalene-1-yl)sulfonyl)-N-(6-(hydroxy amino)-6-oxoheyl)indoline-carboxamide was compared to DIM.

The results of these studies are set forth in FIGS. 7A and 7B where a concentration of 1 µM(S)-1-((5-(dimethylamino)naphthalene-1-yl)sulfonyl)-N-(6-(hydroxyamino)-6-oxoheyl)indoline-carboxamide was used over a time course of 6 hours. The compound (S)-1-((5-(dimethylamino)naphthalene-1-yl)sulfonyl)-N-(6-(hydroxyamino)-6-oxoheyl)indoline-carboxamide was compared to KU55399, DMSO, DIM, and radiation (irradiation of the MCF7 cells at 6 Gy).

Example 10

Figure 8A:
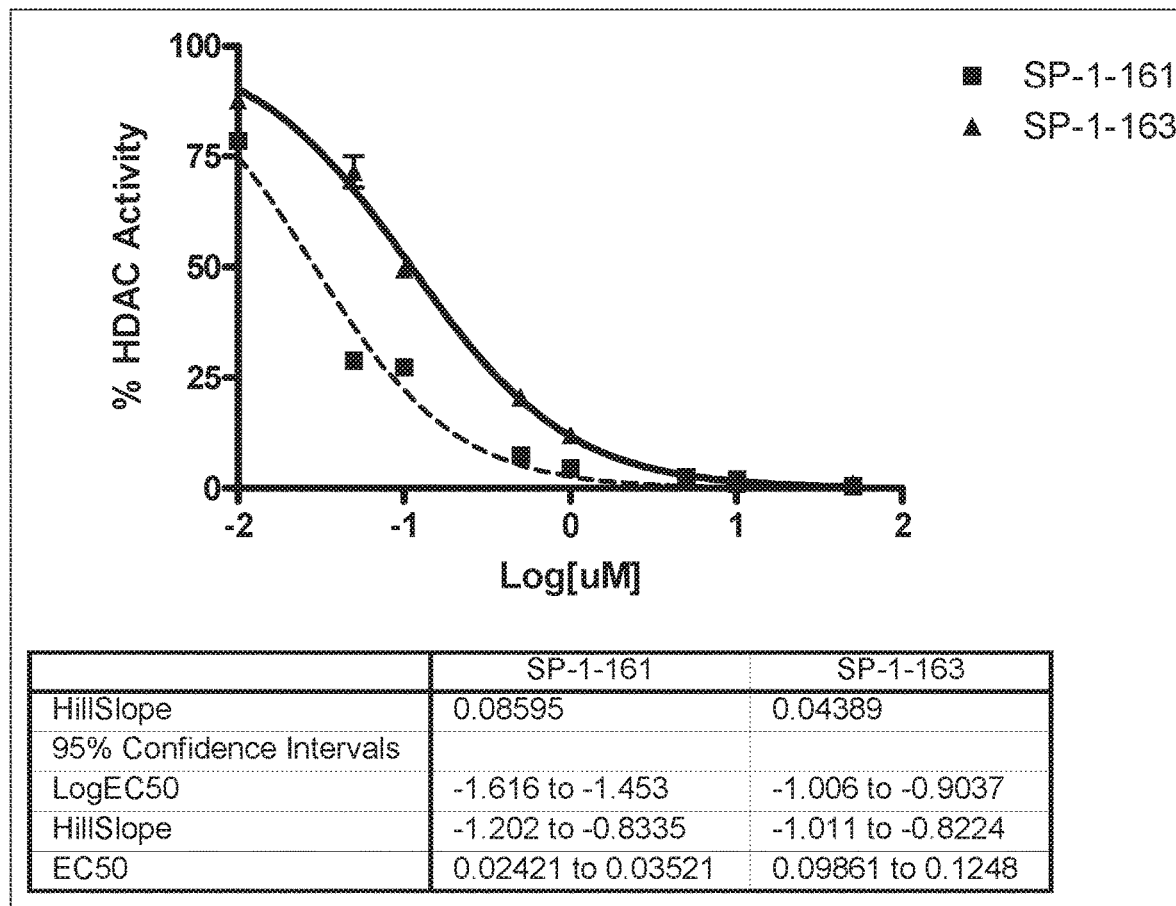
FIGS. 8A and 8B graphically illustrate the activity of certain exemplary compounds of the invention as HDAC inhibitors. Specifically, the compounds tested included: N-(6-(hydroxyamino)-6-oxohexyl)-3-methyl-1H-indole-2-carboxamide (SP-1-161) (FIG. 8A); $N^1$-hydroxy-$N^6$-(2-(2-methyl-1H-indol-3-yl)ethyl)octanediamide (SP-1-163) (FIG. 8A); (S)—N-(6-(hydroxyamino)-6-oxohexyl)-1-tosylindoline-2-carboxamide (SP-1-169) (FIG. 8B); and (S)-1-((5-(dimethylamino)naphthalene-1-yl)sulfonyl)-N-(6-(hydroxyamino)-6-oxoheyl)indoline-carboxamide (SP-1-171) (FIG. 8B).
Figure 8B:
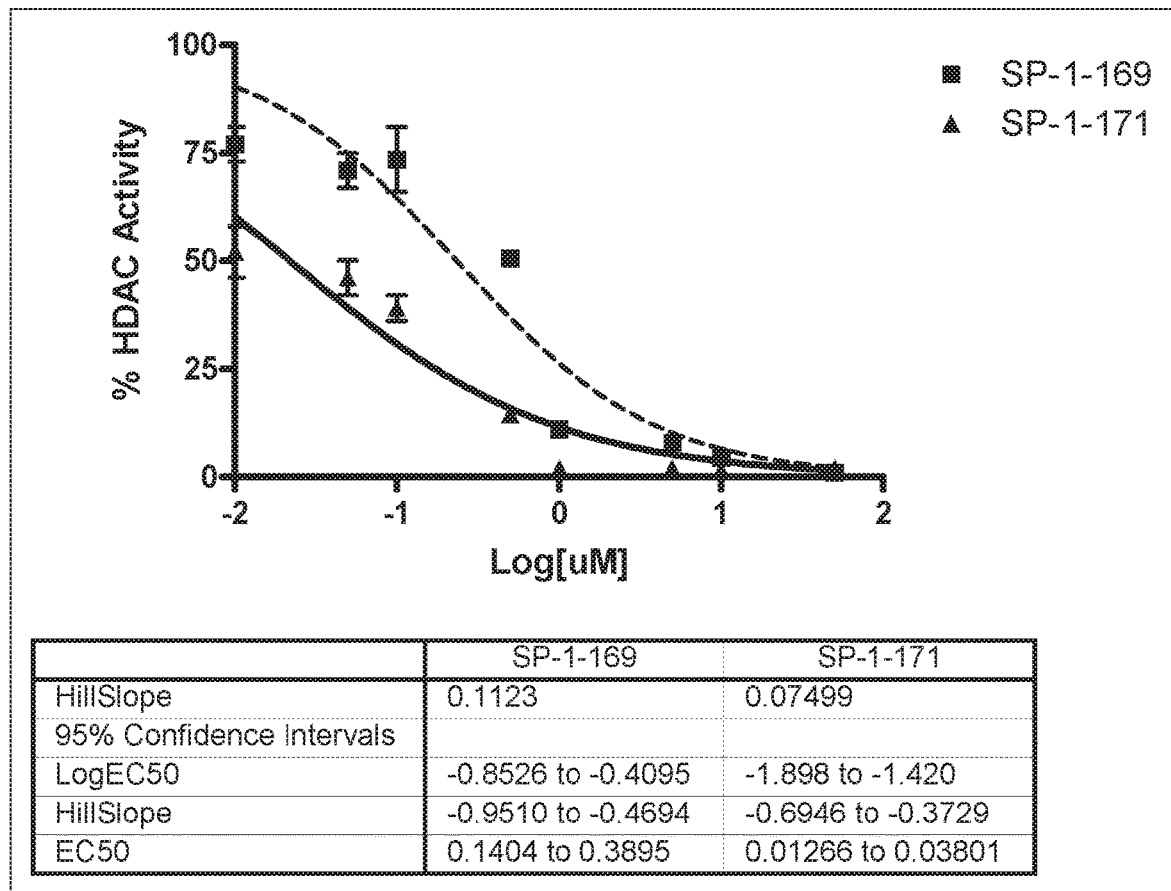

Activity of the Compounds of the Invention as HDAC Inhibitors (see FIGS. 8A and 8B)

Certain compounds of the invention were tested in a pan-HDAC assay to determine the ability of such compounds to inhibit HDAC protein. Specifically, the compounds tested included: N-(6-(hydroxyamino)-6-oxohexyl)-3-methyl-1H-indole-2-carboxamide (SP-1-161) (FIG. 8A); $N^1$-hydroxy-$N^6$-(2-(2-methyl-1H-indol-3-yl)ethyl)octanediamide (SP-1-163) (FIG. 8A); (S)—N-(6-(hydroxyamino)-6-oxohexyl)-1-tosylindoline-2-carboxamide (SP-1-169) (FIG. 8B); and (S)-1-((5-(dimethylamino)naphthalene-1-yl)sulfonyl)-N-(6-(hydroxyamino)-6-oxoheyl)indoline-carboxamide (SP-1-171) (FIG. 8B).

The Pan HDAC assay was performed as follows:

Materials: Enzo Fluor-de-Lys HDAC fluorometric activity assay kit; 360 nm excitation 460 nm emission Plate Reader; Disposable pipettes; Pipet-aid; Pipette tips; Micropipetter; DMSO; Sterile micro-tubes and conical tubes; and Micro-centrifuge.

Test compounds and control preparation: All test compounds' stock solutions were made in 100% DMSO. Test compound dilutions were made in HDAC Assay buffer with a final concentration of DMSO less than or equal to 1%. Vehicle control was HDAC Assay buffer with 1% DMSO.

The reagents for the assay were prepared as follows:

1. All kit components were defrosted and these, and all dilutions described below, were kept on ice until use. All undiluted kit components are stable for several hours on ice.

2. A sufficient amount of HeLa Nuclear Extract (BML-KI140) or other HDAC source diluted in Assay Buffer (BML-KI143) was prepared to provide for the assays that were performed (# of wells×15 µl). A 30-fold dilution of the HeLa Extract means that 15 µl contains 0.5 µl of the undiluted Extract, an appropriate amount to use per well.

3. Dilution(s) of Trichostatin A and/or Test Inhibitors were prepared in Assay Buffer (BML-KI143). Since 10 µl were used per well, and since the final volume of the HDAC reaction was 50 µl, these inhibitor dilutions were 5× their final concentration.

4. Dilution(s) of the Fluor de Lys® Substrate (BML-KI104; 50 mM) were prepared in Assay Buffer (BML-KI143) that were 2× the desired final concentration(s). For inhibitor screening, substrate concentrations at or below the Km are recommended. Twenty-five µL were used per well. Initial dilutions of 25-fold or greater in Assay Buffer (2.0 mM or less) yielded stable solutions (see NOTE on freezing and thawing below). Rapid mixing and dilution into room temperature buffer helped to prevent precipitation at high substrate concentration. NOTE: Freezing/thawing of Fluor de Lys® Substrate solutions in Assay Buffer may cause precipitation of the Substrate. Dilute only amount necessary for one day's experiment.

5. Shortly before use (<30 min.), sufficient Fluor de Lys® Developer was prepared for the assays to be performed (50 µl per well). First, the Fluor de Lys® Developer Concentrate was diluted 20-fold (e.g. 50 µl plus 950 µl Assay Buffer) in cold Assay Buffer (BML-KI143). Second, the 0.2 mM Trichostatin A (BML-GR309-9090) was diluted 100-fold in the 1× Developer just prepared (e.g. 10 µl in 1 ml; final Trichostatin A concentration in the 1× Developer=2 µM; final concentration after addition to HDAC/Substrate reaction=1 µM). The addition of Trichostatin A to the Developer insures that HDAC activity stops when the Developer is added. The Developer was kept on ice until use.

Assay Procedure:

1. Assay buffer, diluted trichostatin A or test inhibitor was added to appropriate wells of the microtiter plate.

2. Diluted HeLa extract or other HDAC sample was added to all wells except those that are to be "No Enzyme Controls."

3. Diluted Fluor de Lys® Substrate and the samples in the microtiter plate were allowed to equilibrate to assay temperature (e.g. 25 or 37° C.).

4. HDAC reactions were initiated by adding diluted substrate (25 µl) to each well and mixing thoroughly.

5. HDAC reactions were allowed to proceed for desired length of time and then stop them by addition of Fluor de Lys® Developer (50 µl). The plates were incubated at room temperature (25° C.) for 10-15 min. Signal is stable for at least 30 min. beyond this time.

6. Samples were read in a microtiter-plate reading fluorimeter capable of excitation at a wavelength in the range 350-380 nm and detection of emitted light in the range 440-460 nm.

A shown in FIGS. 8A and 8B, the tested compounds demonstrated inhibitor activity in the Pan-HDAC assay. For example, as shown in FIG. 8A, N-(6-(hydroxyamino)-6-oxohexyl)-3-methyl-1H-indole-2-carboxamide and $N^1$-hydroxy-$N^6$-(2-(2-methyl-1H-indol-3-yl)ethyl)octanediamide (SP-1-163) demonstrated an average $EC_{50}$ of 0.02971 µM and 0.1117 µM, respectively. Moreover, as shown in FIG. 8B, (S)—N-(6-(hydroxyamino)-6-oxohexyl)-1-tosylindoline-2-carboxamide (SP-1-169) and (S)-1-((5-(dimethylamino)naphthalene-1-yl)sulfonyl)-N-(6-(hydroxyamino)-6-oxoheyl)indoline-carboxamide (SP-1-171) demonstrated an average $EC_{50}$ of 0.2649 µM and 0.02533 µM, respectively.

Example 11

Cytotoxicity Testing of the Compounds of the Invention in Breast Cancer Cells (MCF7 Cells) and Normal Breast Cells (184A1 Cells) (See FIG. 9)

Certain compounds of the invention were tested in both an MTT cytotoxicity assay and clonogenic cytotoxicity assay against breast cancer cells (MCF7 cells) and normal breast tissue cells (184A1 cells) to determine the cytotoxic effect of such cells as a function of concentration.

Specifically, the compounds tested included: N-(6-(hydroxyamino)-6-oxohexyl)-3-methyl-1H-indole-2-carboxamide (SP-1-161); -hydroxy-N⁶-(2-(2-methyl-1H-indol-3-yl)ethyl)octanediamide (SP-1-163); (S)—N-(6-(hydroxyamino)-6-oxohexyl)-1-tosylindoline-2-carboxamide (SP-1-169); and (S)-1-((5-(dimethylamino)naphthalene-1-yl)sulfonyl)-N-(6-(hydroxyamino)-6-oxoheyl)indoline-carboxamide (SP-1-171).

As demonstrated in FIG. 9, SP-1-161 was the most cytotoxic having IC$_{50}$s of 0.416 and 0.276 μM in the MTT assay and clonogenic assay, respectively.

Example 12

Figure 11A:
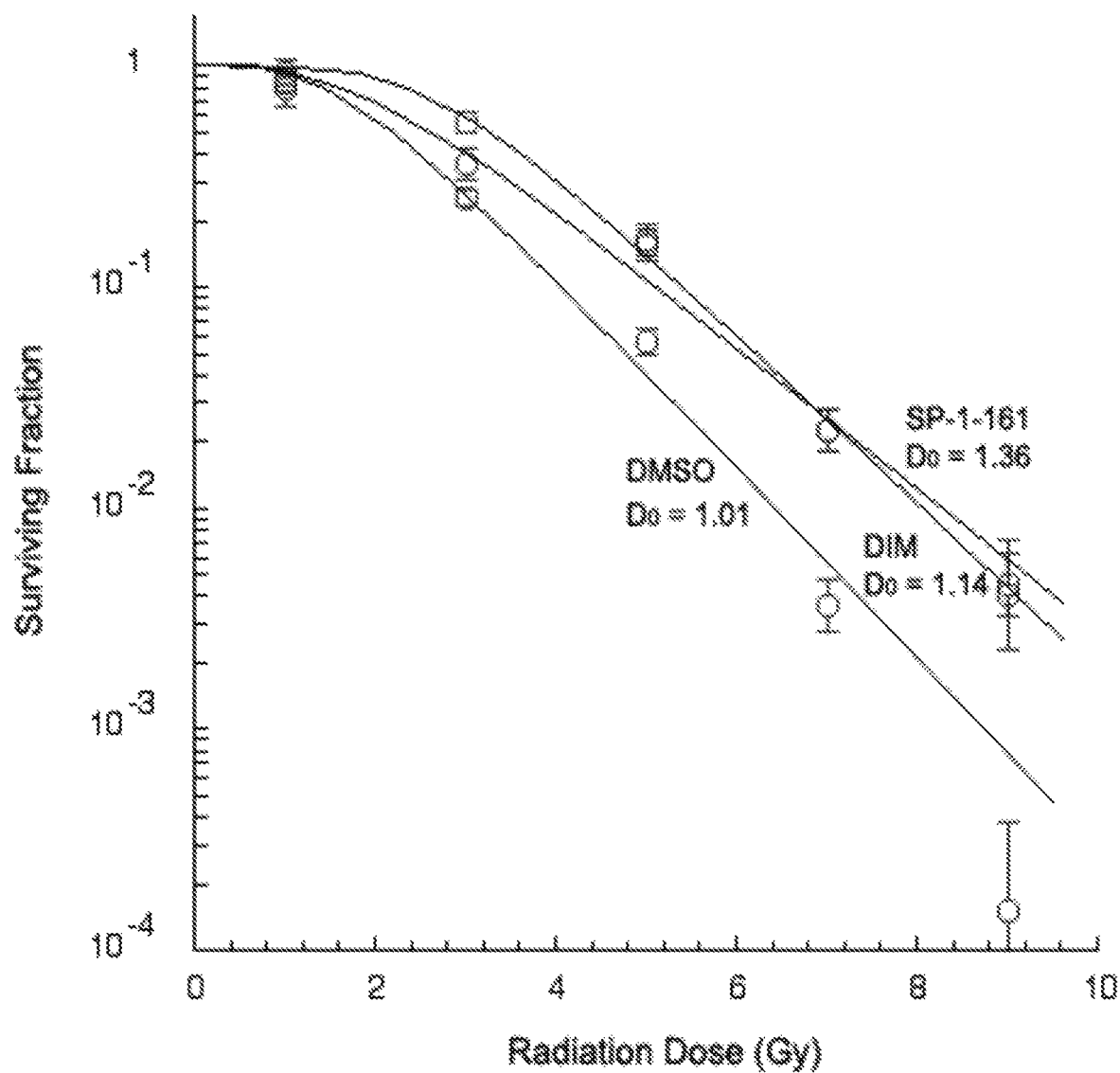
FIGS. 11A and 11B graphically illustrate the effect of N-(6-(hydroxyamino)-6-oxohexyl)-3-methyl-1H-indole-2-carboxamide (SP-1-161), DIM, and DMSO on radiation clonogenic survivals in normal breast epithelial cells (184A1 cells) (FIG. 11A) and breast cancer cells (MCF7 cells) (FIG. 11B).
Figure 11B:
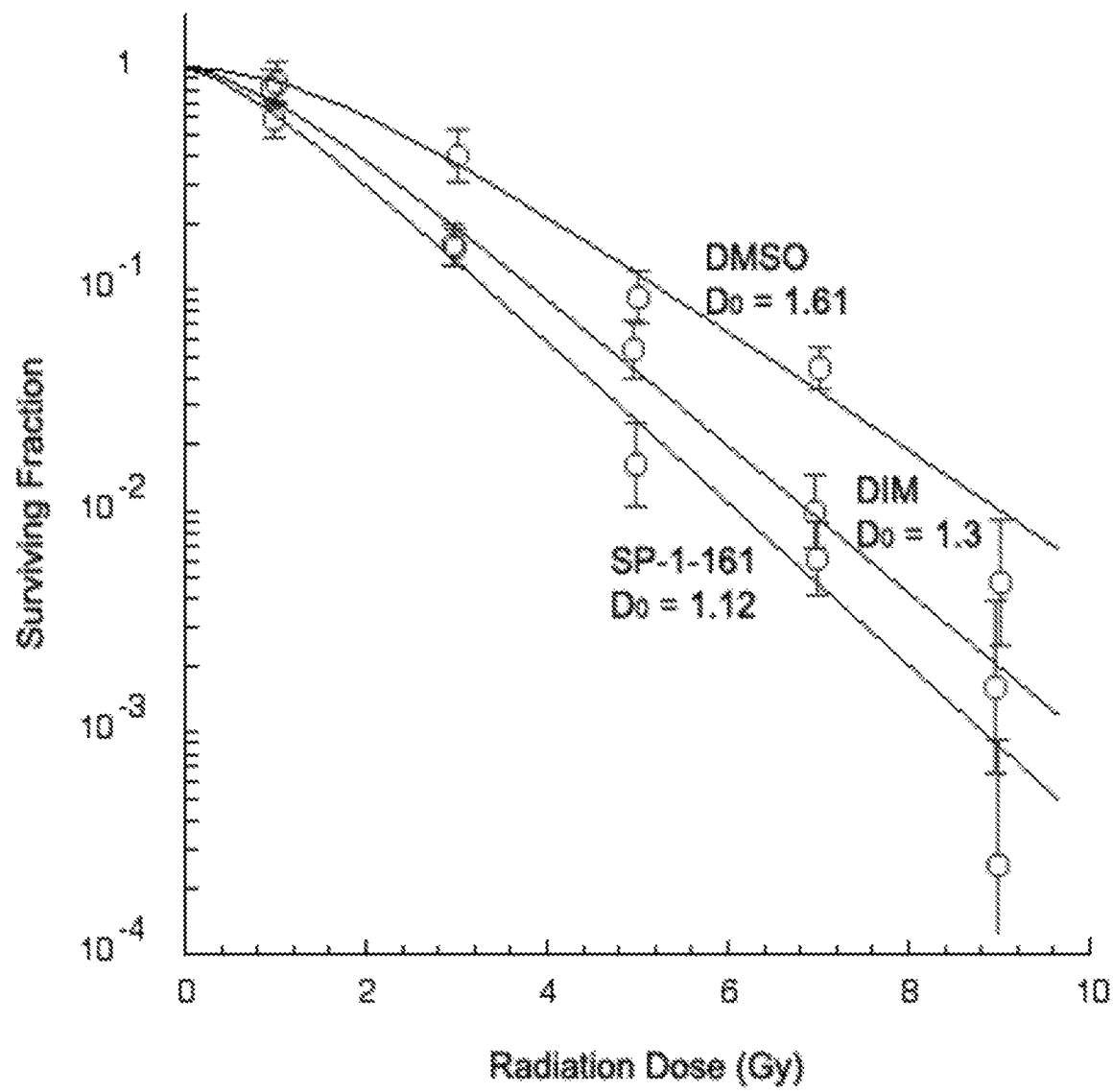

Comparison of the Effect of N-(6-(hydroxyamino)-6-oxohexyl)-3-methyl-1H-indole-2-carboxamide (SP-1-161) and DIM on Radiation Clonogenic Survivals in Normal and Cancerous Cells (FIGS. 10, 11A, and 11B)

A comparison of the effect of SP-1-161 with DMSO (control vehicle) and DIM on radiation clonogenic survivals and parameters is shown in FIG. 10.

N-(6-(hydroxyamino)-6-oxohexyl)-3-methyl-1H-indole-2-carboxamide (SP-1-161) was tested against DIM in a radiation clonogenic survival study with healthy breast epithelial cells (184A1 cells) (FIG. 11A) and breast cancer cells (MCF7 cells) (FIG. 11B). After treatment with the compounds of the invention for 24 hours, the cells were exposed to graded doses of gamma radiation.

Logarithmically growing cells were seeded into T-25 flasks at various densities to yield approximately 50-100 colonies/flask. After incubation for 24 h at 37° C., cells were treated or not with the compound at the IC$_{50}$ concentration for 24 h followed by sham or irradiation at room temperature using a Mark-30 irradiator with a 137-Cs source at a fixed dose rate of 2.27 Gy/min. After 10-14 days, cells were fixed and stained with crystal violet, and colonies of more than 50 cells were counted. The surviving fractions of the treated cells were normalized to the plating efficiencies of untreated controls. Radiation survival curves were fitted by computer to the single-hit, multitarget and the linear-quadratic models.

The radiation sensitivity of cells is defined by the terminal slope of the radiation survival curve, which is referred to as D$_0$. The steeper the slope, the smaller is the value of D$_0$, and thus the more radiation sensitive the respective cells. Alternatively, a less steep slope results in a larger D$_0$ and a more resistant radiation response.

As demonstrated in FIG. 11B, SP-1-161 demonstrated radiation sensitizing activity and further outperformed DIM in treating breast cancer cells (MCF7) when combined with radiation. Moreover, FIG. 11A demonstrates that SP-1-161 protected normal cells from radiation-mediated killing by a means of increasing the D$_0$ value. Indeed, the surviving population of healthy cells treated with SP-1-161 was comparable to that of DIM, indicating that that SP-1-161 provided protective activity comparable to DIM.

Example 13

Figure 12:
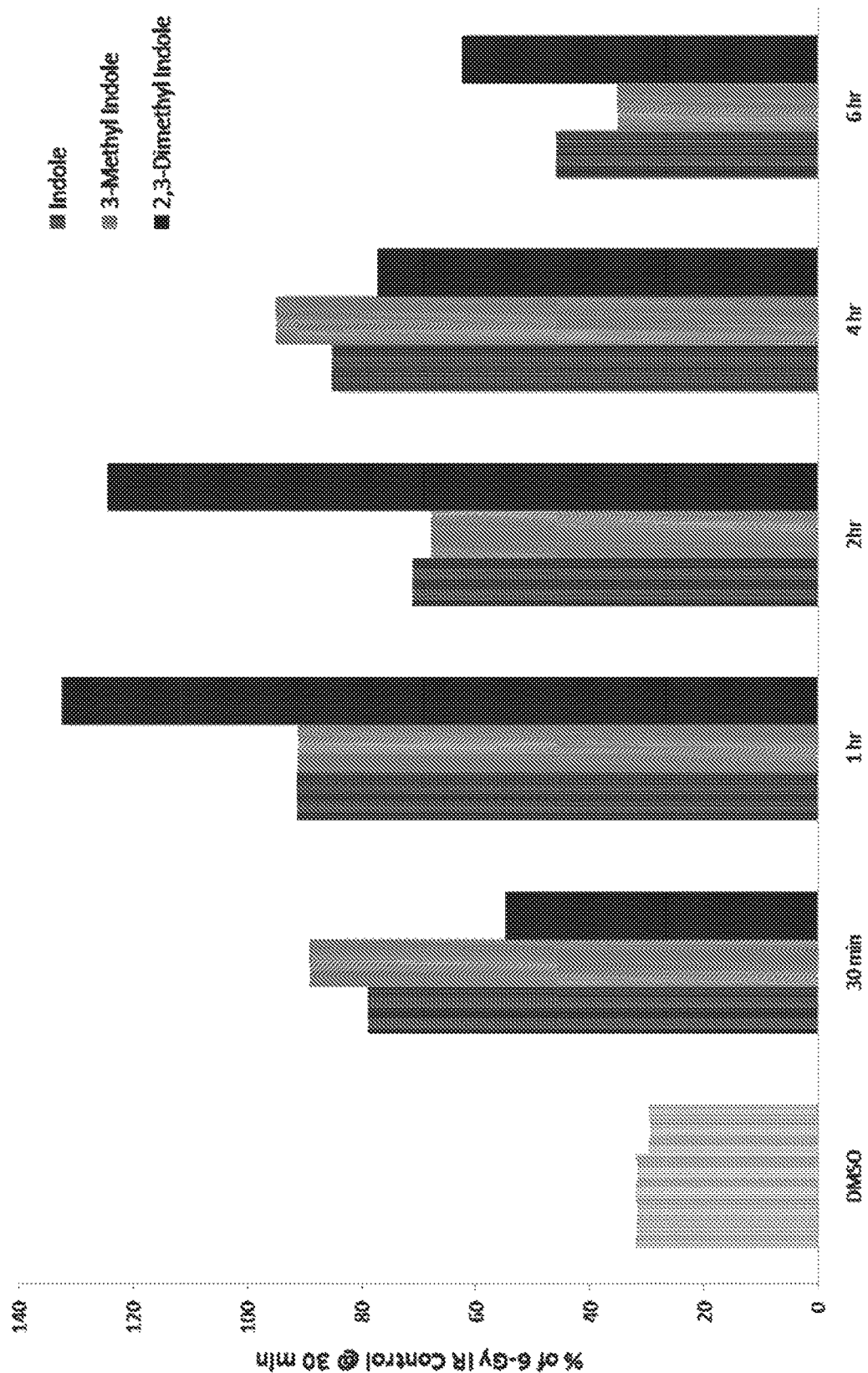
FIG. 12 graphically illustrates the level of ATM phosphorylation induced after exposure to various indole compounds at 1 µM as a percentage of the ATM phosphorylation level of cells treated with ionizing radiation at 6 Gy. The phospho-ATM levels were measured at 30 minutes, 1 hr, 2 hr, 4 hr, and 6 hr post exposure to radiation. Specifically, indole, 3-methyl indole, and 2,3-dimethyl indole were compared. 2,3-dimethyl indole demonstrated a significant increase in ATM phosphorylation when compared to indole and 3-methyl indole. MCF7 cells were treated and the nuclear fraction was extruded and analyzed via Elisa assay for P-ATM (S1982).

Comparison of the Effect of Indole Methylation on ATM Activation (FIG. 12)

Several compounds of the invention include alkylated indole moieties. In an effort to better understand the compounds of the invention, and their biological activity, we developed a study to measure the ATM activating properties of substituted and unsubstituted indoles.

Without being restricted to any one theory of the invention, it is believed that the compounds of the invention derive ATM activation activity from one or more indole moieties as described in Formulas I-IV. See, for example, SP-1-161 and SP-1-163. To test this understanding, certain indole species were tested for their effects on ATM phosphorylation (i.e., an indicator of ATM activation) in the absence of a hydroxamic acid moiety. Specifically, this study examined a homologous series of indoles that included the unsubstituted indole, methylindole, and dimethylindole.

The activity of indole, 3-methyl-indole, and 2,3-dimethyl indole was determined as set forth in Example 5 (FIG. 12).

The results of these studies are set forth in FIG. 12 where a concentration of 1 μM indole, 3-methyl-indole, and 2,3-dimethyl indole was used over a time course of 6 hours. The methylated indoles were compared to DMSO (irradiation of the MCF7 cells at 6 Gy).

As shown in FIG. 12, ATM-activation, as determined by the fold change in phospho-ATM, occurred with all indole species as compared to DMSO. Surprisingly, there was marked difference between indole and the tested methylated indoles. Specifically, as methylation increased, there was a marked increase in the level of ATM phosphorylation. Indeed, 2,3-dimethylindole showed a significant increase in ATM activation between 1 and 2 hours pos-radiation exposure as compared to indole and 3-methyl indole.

This study indicates that indole species may provide for direct ATM activation where such tested indole species increased the level of ATM phosphorylation as compared to a control. Moreover, the level of methylation about the indole ring correlated to an increased level of ATM activation, as compared to unsubstituted indole.

Extrapolating this data to the compounds of the invention, we may better understand the exceptional activities of N-(6-(hydroxyamino)-6-oxohexyl)-3-methyl-1H-indole-2-carboxamide (i.e., SP-1-161) and N$^1$-hydroxy-N$^6$-(2-(2-methyl-1H-indol-3-yl)octanediamide (i.e., SP-1-163). Indeed, both SP-1-161 and SP-1-163 both include disubstituted indoles and display exemplary ATM activation activity as dual function agents of the invention.

Example 14

Cytotoxicity Testing of the Compounds of the Invention in Breast, Prostate, Cervix, and Head and Neck Cancer Cell Lines (see FIG. 13)

Certain compounds of the invention were tested in an MTT cytotoxicity assay against a breast cancer cell line (MCF7), prostate cancer cell line (PC3), cervical cancer cell line (CasKi), and head and neck cancer cell line (SQ20B). In the breast and prostate cancer MTT assays, certain compounds of the invention were also tested against normal breast (MCF10A) and prostate (RWPE1) epithelial tissues.

Specifically, the compounds tested included SP-1-161, SP-1-229, and SP-1-303. Suberoylanilide hydroxamic acid (SAHA), a known HDAC inhibitor, was also tested in the assay as control.

As shown in FIG. 13, the compounds of the invention demonstrated the cytotoxic activity of SP-1-161, SP-1-229, and SP-1-303 in various cancer cell lines, including breast cancer (MCF7), prostate cancer (PC3), cervical cancer (CasKi), and head and neck cancer (SQ20B) cell lines. Suberoylanilide hydroxamic acid (SAHA) was also included in the assay for comparison. The data showed that SP-1-229 and SP-1-303 were 7.5-fold and 35-fold less toxic, respectively, in normal breast epithelial cells than those in cancer cells (MCF-7). Similar results were also obtained in normal prostate epithelial (RWPE1) cells and prostate cancer (PC3) cells; 15-fold of SP-1-161, 77-fold of SP-1-299, and 39-fold of SP-1-303. The data support the use of SP-1-229 and SP-1-303 in treatment of hormone-driven cancers, such as breast cancer, prostate cancer, and ovarian cancer.

Example 15

Figure 14:
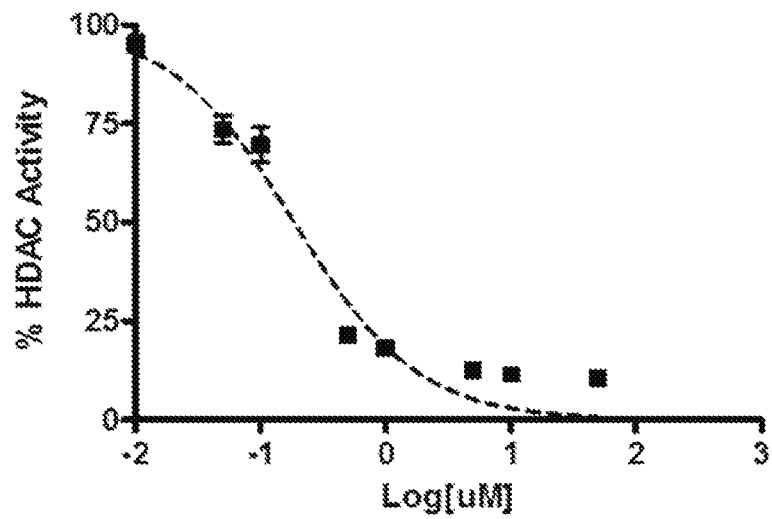
FIG. 14 graphically illustrates the activity of SP-1-229 as an HDAC inhibitor ($EC_{50}$=0.186 μM).
Figure 15:
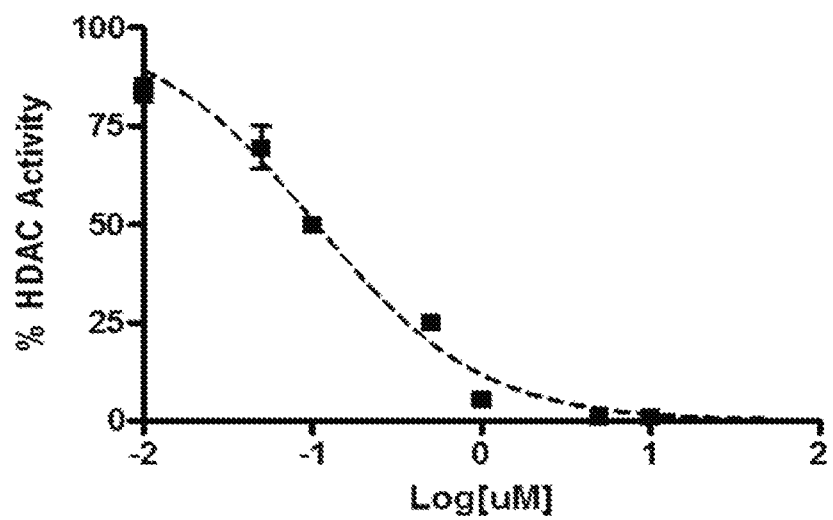
FIG. 15 graphically illustrates the activity of SP-1-303 as an HDAC inhibitor ($EC_{50}$=0.106 μM).

Activity of SP-1-229 and SP-1-303 as HDAC Inhibitors (see FIGS. 14 and 15)

The activity of SP-1-161, SP-1-229, and SP-1-303 as HDAC inhibitors was determined as set forth in Example 10. SP-1-229 was determined to have an $EC_{50}$ of 0.186 µM against pan-HDACs (FIG. 14). SP-1-303 was determined to have an $EC_{50}$ of 0.106 µM against pan-HDACs (FIG. 15).

Example 16

Figure 16:
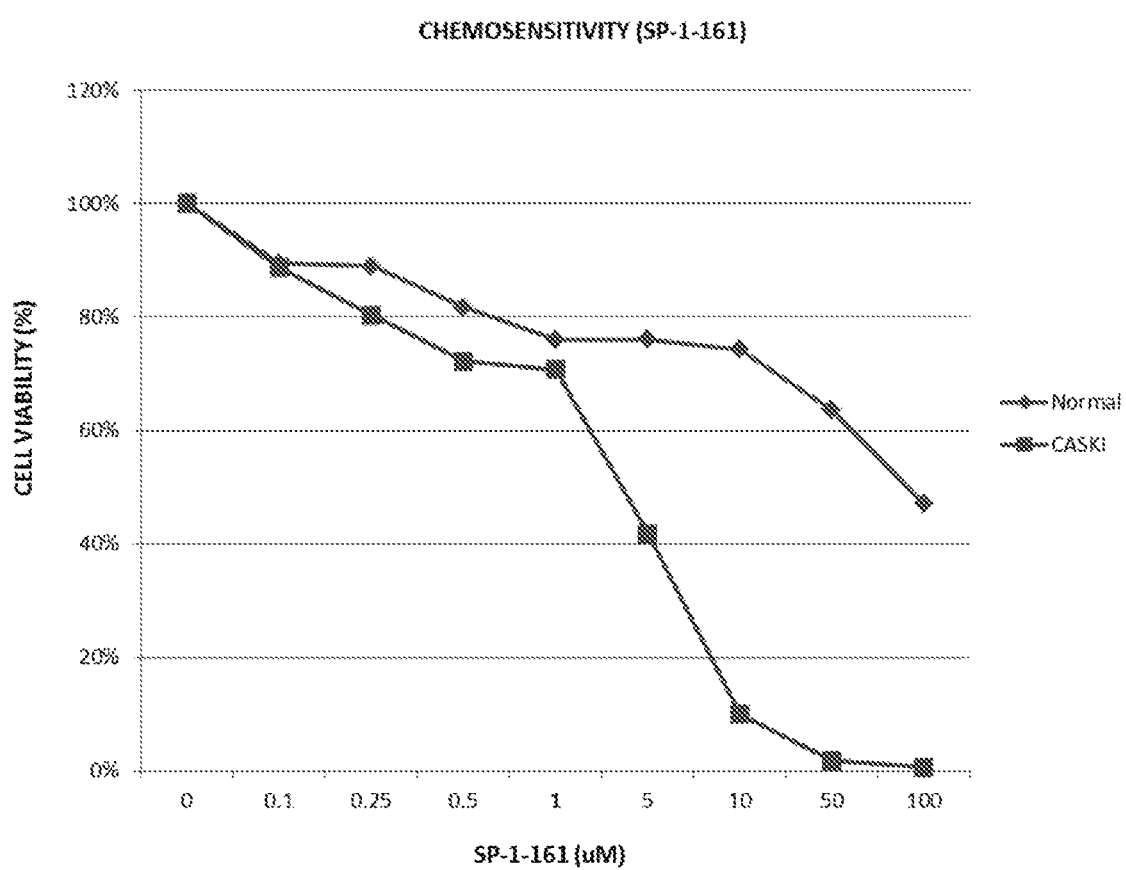
FIG. 16 graphically demonstrates the chemosensitivity of normal epithelial cells (RWPE1 cells) and HPV+ cervical cancer cells (CasKi cells) to SP-1-161. The $IC_{50}$ for HPV+ CasKi cells is 29 times lower than that for normal epithelial cells. This supports a role for compounds of the invention (e.g., SP-1-161) as treatments for HPV+ cancers.

Chemosensitivity of Normal and Cancerous Cervical Cells to SP-1-161 (FIG. 16)

SP-1-161 was tested in a MTT cytotoxicity assay against normal epithelial cells and human papilloma virus positive (HPV+) cancerous (CasKi) cervical cells. As shown in FIG. 16, normal cervical cells were less sensitive to SP-1-161 as compared to cancerous cervical cells (CasKi). In fact, the $IC_{50}$ for SP-1-161 against HPV+ CasKi cells was 29 times lower than that for normal epithelial cells (RWPE1 cells). This supports the role for the compounds of the invention (e.g., SP-1-161) as treatments of HPV+ cancers and tumors.

Example 17

Figure 17:
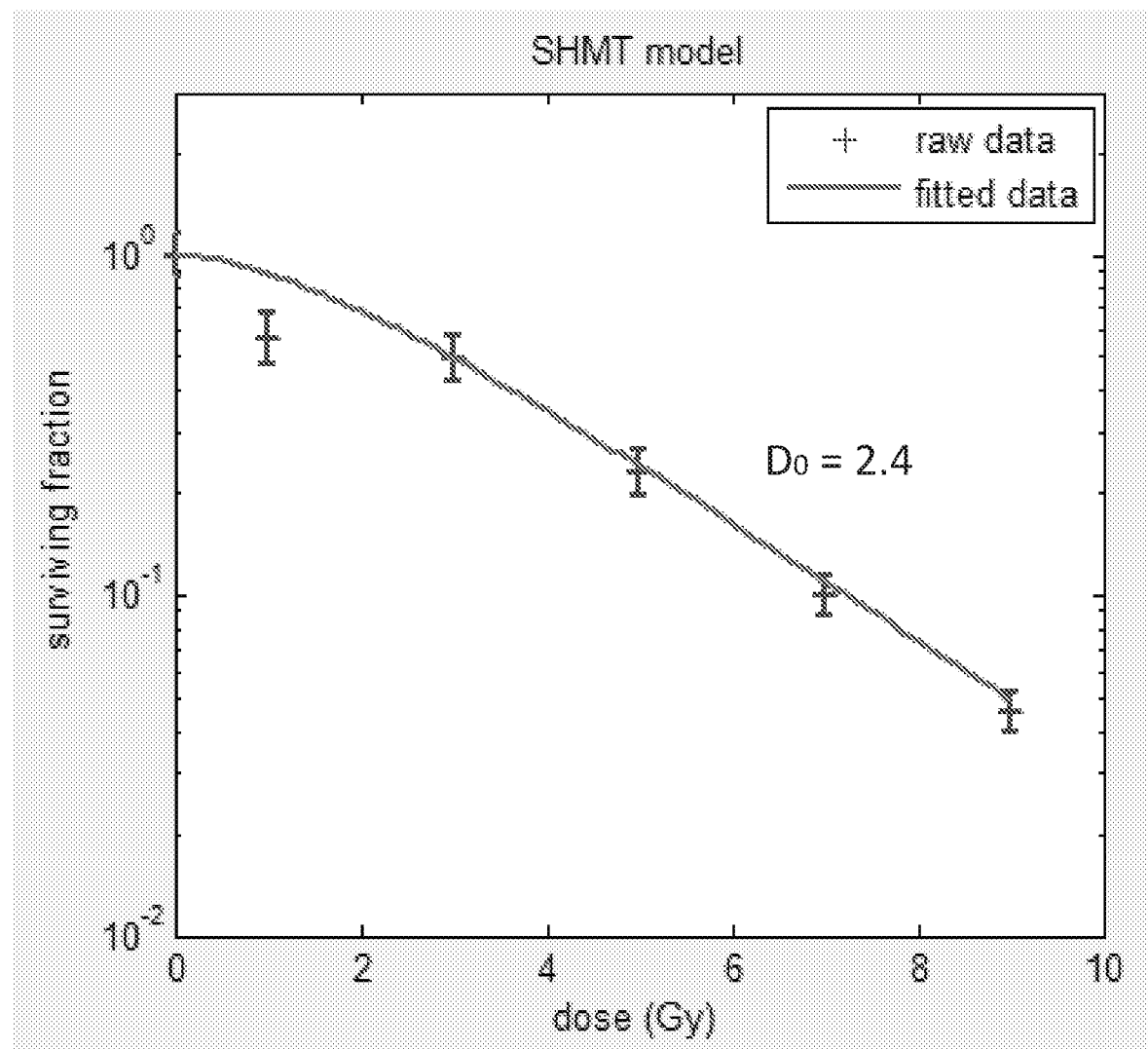
FIG. 17 graphically illustrates the effect of DMSO (control) on HPV+ CasKi cells, in combination with radiation ($D_0$=2.4).
Figure 18:
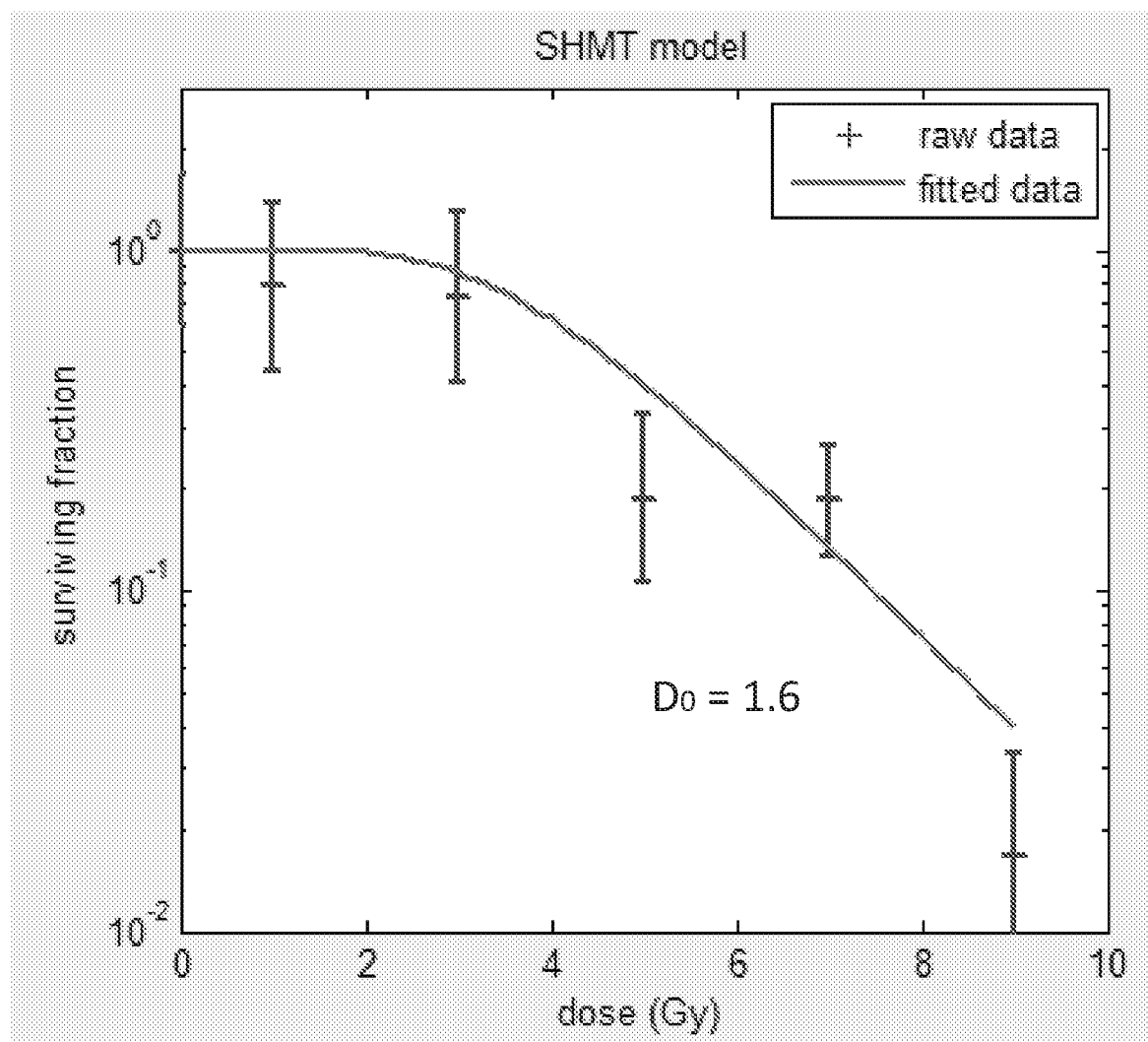
FIG. 18 graphically illustrates the effect of SP-1-161 on HPV+ CasKi cells, in combination with radiation ($D_0$=1.6).
Figure 19:
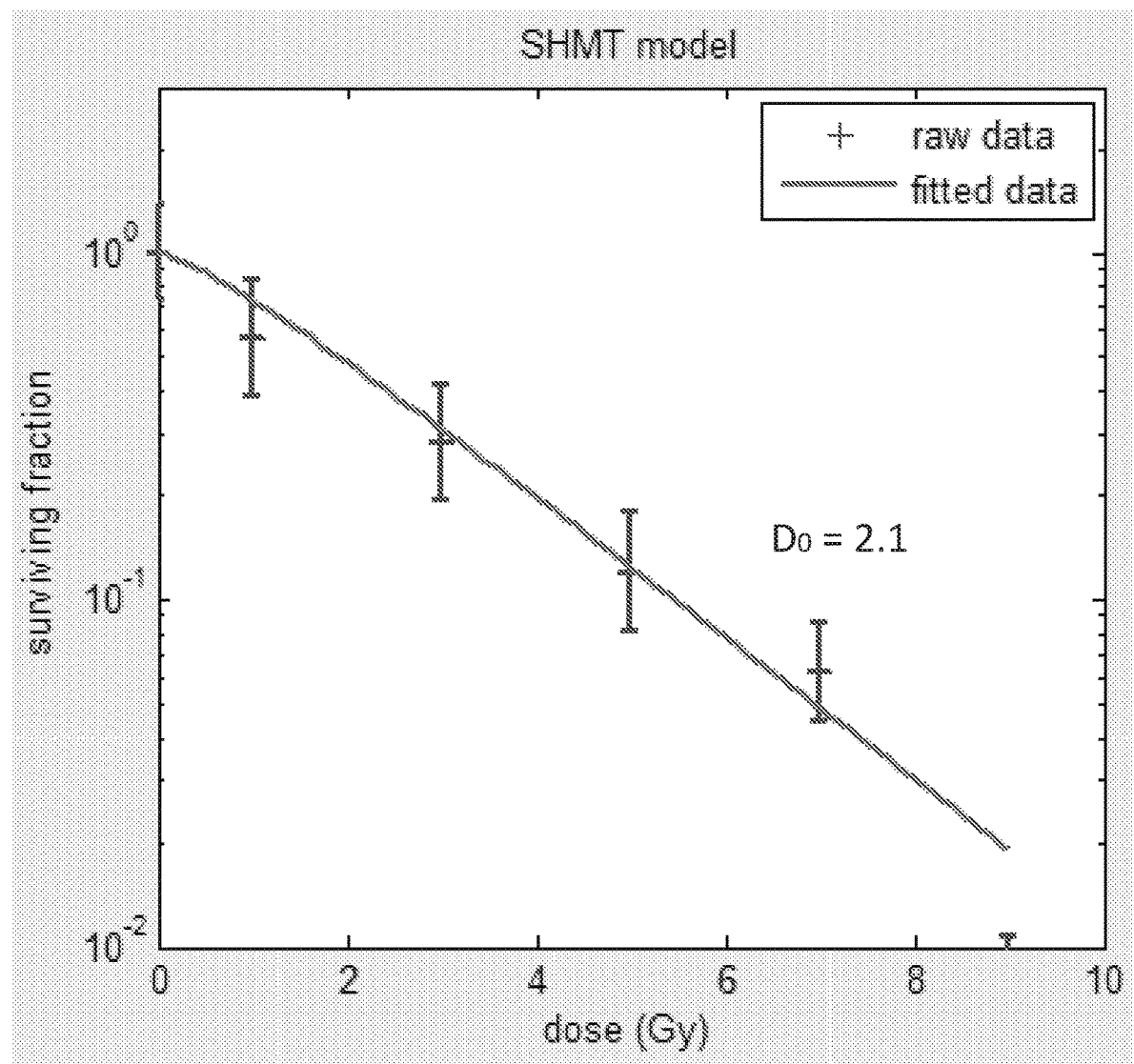
FIG. 19 graphically illustrates the effect of SP-1-303 on HPV+ CasKi cells, in combination with radiation ($D_0$=2.1).

Clonogenic Survival Study of Cervical Cancer Cells Treated with SP-1-161 or SP-1-303 in Combination with Radiation (FIGS. 17-19)

FIGS. 17-19 illustrate the effects of drugs on radiation cologenetic survivals. Cells were pretreated with drug 24 hours prior to exposure to graded doses of gamma radiation. Compounds SP-1-161 and SP-1-303 were tested in a clonogenic survival study with cervical cancer cells (CasKi) with a protocol similar to that described in Example 12. The radiation sensitivity of cells is defined by the terminal slope of the radiation survival curve, which is referred to as $D_0$. The steeper the slope, the smaller the value of $D_0$ and thus the more radiation sensitive the respective cells. Alternatively, a less steep slope results in a larger $D_0$ and a more resistant radiation response. The results of this assay are presented in FIG. 17 (DMSO control at $D_0$=2.4), FIG. 18 (SP-1-161 at $D_0$=1.6), and FIG. 19 (SP-1-303 at $D_0$=2.1). SP-1-161 and SP-1-303 compounds of the invention sensitized CasKi cells as shown by decreasing the $D_0$ value with respect to the control in FIG. 17.

A number of patent and non-patent publications are cited herein in order to describe the state of the art to which this invention pertains. The entire disclosure of each of these publications is incorporated by reference herein.

While certain embodiments of the present invention have been described and/or exemplified above, various other embodiments will be apparent to those skilled in the art from the foregoing disclosure. The present invention is, therefore, not limited to the particular embodiments described and/or exemplified, but is capable of considerable variation and modification without departure from the scope of the appended claims.

Moreover, as used herein, the term "about" means that dimensions, sizes, formulations, parameters, shapes and other quantities and characteristics are not and need not be exact, but may be approximate and/or larger or smaller, as desired, reflecting tolerances, conversion factors, rounding off, measurement error and the like, and other factors known to those of skill in the art. In general, a dimension, size, formulation, parameter, shape or other quantity or characteristic is "about" or "approximate" whether or not expressly stated to be such. It is noted that embodiments of very different sizes, shapes and dimensions may employ the described arrangements.

Furthermore, the transitional terms "comprising", "consisting essentially of" and "consisting of", when used in the appended claims, in original and amended form, define the claim scope with respect to what unrecited additional claim elements or steps, if any, are excluded from the scope of the claim(s). The term "comprising" is intended to be inclusive or open-ended and does not exclude any additional, unrecited element, method, step or material. The term "consisting of" excludes any element, step or material other than those specified in the claim and, in the latter instance, impurities ordinary associated with the specified material(s). The term "consisting essentially of" limits the scope of a claim to the specified elements, steps or material(s) and those that do not materially affect the basic and novel characteristic(s) of the claimed invention. All compounds, compositions, and methods described herein that embody the present invention can, in alternate embodiments, be more specifically defined by any of the transitional terms "comprising," "consisting essentially of," and "consisting of"

REFERENCES

1. Kouzarides T. Histone acetylases and deacetylases in cell proliferation. Curr Opinion Genet Dev 9:40-48, 1999.
2. De Ruijter A J, Van Gennip A H, Caron H N, Kemp S, and Van Kuilenburg A B. Histone deacetylases (HDACs): characterization of the classical HDAC family. Biochem J 370: 737-749, 2003.
3. Struhl K and Moqtaderi Z. The TAFs in the HAT. Cell. 94:1-4, 1998.
4. Grunstein M. Histone acetylation in chromatin structure and transcription. Nature 389: 349-352, 1997.
5. Wolffe A P and Guschin D. Review: chromatin structural features and targets that regulate transcription. J. Structural Sci. 129:102-122, 2000.
6. Struhl K. Histone acetylation and transcriptional regulatory mechanisms. Genes Dev 12:599-606, 1998.
7. Kurdistani S K, and Grunstein M. Histone acetylation and deacetylation in yeast. Nat Rev Mol Cell Biol 4: 276-284, 2003.
8. Gregoretti I V, Lee Y M, Goodson H V. Molecular evolution of the histone deacetylase family: functional implications of phylogenetic analysis. JMC 338: 17-31, 2004.
9. Nome R V, Bratland A, Harman G, Fodstad O, Andersson Y, Ree A H. Mol. Cell cycle checkpoint signaling involved in histone deacetylase inhibition and radiation-induced cell death. Cancer Ther 4:1231-1238, 2005.
10. Arundel C M, Leith J T. Effects of nucleoside analogs and sodium butyrate on recovery from potentially lethal X ray damage in human colon tumor cells. Int J Radiat Oncol Biol Phys. 13:593-601, 1987.

11. Zhang Y, Carr T, Dimtchev A, Zaer N, Dritschilo A, Jung M. Attenuated DNA damage repair by trichostatin A through BRCA1 suppression. Radiat Res 168:115-124, 2007.
12. Gleave M E, Sato N, Sadar M, Yago V, Bruchovsky N, Sullivan L. Butyrate analogue, isobutyramide, inhibits tumor growth and time to androgen-independent progression in the human prostate LNCaP tumor model. J Cell Biochem 69:271-81, 1998.
13. Melchior S W, Brown L G, Figg W D, Quinn J E, Santucci R A, Brunner J, Thüroff J W, Lange P H, Vessella R L. Effects of phenylbutyrate on proliferation and apoptosis in human prostate cancer cells in vitro and in vivo. Int J Oncol 14:501-508, 1999.
14. Marks P A, Richon V M, Rifkind R A. Histone deacetylase inhibitors: inducers of differentiation or apoptosis of transformed cells. J Natl Cancer Inst; 92:1210-1216, Review, 2000.
15. Zhou B B, Elledge S J. The DNA damage response: putting checkpoints in perspective. Nature 408:433-439. Review, 2000.
16. Peterson C L, Cote J. Cellular machineries for chromosomal DNA repair. Genes Dev 18:602-616. Review, 2004.
17. Ito A, Kawaguchi Y, Lai C H, Kovacs J J, Higashimoto Y, Annetta E, Yao T P. MDM2-HDAC1-mediated deacetylation of p53 is required for its degradation. EMBO J 21:6236-6245, 2002.
18. Marks P, Rifkind R A, Richon V M, Breslow R, Miller T, Kelly W K. Histonedeacetylases and cancer: causes and therapies. Nat Rev Cancer 1:194-202. Review, 2001.
19. Johnstone R W. Histone-deacetylase inhibitors: novel drugs for the treatment of cancer. Nat Rev Drug Discov 1: 287-299, 2002.
20. Arundel C M, Glicksman A S, Leith J T. Enhancement of radiation injury in human colon tumor cells by the maturational agent sodium butyrate (NaB). Radiat Res 104:443-448, 1985.
21. Patnaik A, Rowinsky E K, Villalona M A, Hammond L A, Britten C D, Siu L L, Goetz A, Felton S A, Burton S, Valone F H, Eckhardt S G. A phase I study of pivaloyloxymethyl butyrate, a prodrug of the differentiating agent butyric acid, in patients with advanced solid malignancies. Clin Cancer Res 8:2142-2148. Review, 2002.
22. Ryan Q C, Headlee D, Acharya M, Sparreboom A, Trepel J B, Ye J, Figg W D, Hwang K, Chung E J, Murgo A, Melillo G, Elsayed Y, Monga M, Kalnitskiy M, Zwiebel J, Sausville E A. Phase I and pharmacokinetic study of MS-275, a histone deacetylase inhibitor, in patients with advanced and refractory solid tumors or lymphoma. J Clin Oncol 23:3912-3922, 2005.
23. Pauer L R, Olivares J, Cunningham C, Williams A, Grove W, Kraker A, Olson S, Nemunaitis J. Phase I study of oral CI-994 in combination with carboplatin and paclitaxel in the treatment of patients with advanced solid tumors. Cancer Invest 22:886-896, 2004.
24. Perrine S P, Ginder G D, Faller D V, Dover G H, Ikuta T, Witkowska H E, Cai S P, Vichinsky E P, Olivieri N F. A short-term trial of butyrate to stimulate fetal-globin-gene expression in the beta-globin disorders N Engl J Med 328:81-86, 1993.
25. Richon V M, Emiliani S, Verdin E, Webb Y, Breslow R, Rifkind R A, and Marks P A. A class of hybrid polar inducers of transformed cell differentiation inhibits histone deacetylases. Proc Natl Acad Sci USA 95:3003-3007, 1998.
26. Kelly W K, Richon V M, O'Connor O, Curley T, MacGregor-Curtelli B, Tong W, Klang M, Schwartz L, Richardson S, Rosa E, Drobnjak M, Cordon-Cordo C, Chiao J H, Rifkind R, Marks P A, Scher H. Phase I clinical trial of histone deacetylase inhibitor: suberoylanilide hydroxamic acid administered intravenously. Clin Cancer Res 9:3578-3588, 2003.
27. Furumai R, Matsuyama A, Kobashi N, Lee K H, Nishiyama M, Nakajima H, Tanaka A, Komatsu Y, Nishino N, Yoshida M, Horinouchi S. FK228 (depsipeptide) as a natural prodrug that inhibits class I histone deacetylases. Cancer Res 62:4916-4921, 2002.
28. Gottlicher M, Minucci S, Zhu P, Kramer O H, Schimpf A, Giavara S, Sleeman J P, Lo Coco F, Nervi C, Pelicci P G, Heinzel T. Valproic acid defines a novel class of HDAC inhibitors inducing differentiation of transformed cells. EMBO J 20:6969-6878, 2001.
29. Gottlicher M, Minucci S, Zhu P, Kramer O H, Schimpf A, Giavara S, Sleeman J P, Lo Coco F, Nervi C, Pelicci P G, Heinzel T. Valproic acid defines a novel class of HDAC inhibitors inducing differentiation of transformed cells. EMBO J 24:6969-6878, 2001.
30. Camphausen K, Cerna D, Scott T, Sproull M, Burgan W E, Cerra M A, Fine H, Tofilon P J. Enhancement of in vitro and in vivo tumor cell radiosensitivity by valproic acid. Int J Cancer 114:380-386, 2005.
31. Zhou B B, Elledge S J. The DNA damage response: putting checkpoints in perspective. Nature 408:433-439. Review, 2000.
32. Peterson C L, Cote J. Cellular machineries for chromosomal DNA repair. Genes Dev 18:602-616. Review, 2004.
33. Vrana J A, Decker R H, Johnson C R, Wang Z, Jarvis W D, Richon V M, Ehinger M, Fisher P B, Grant S. Induction of apoptosis in U937 human leukemia cells by suberoylanilide hydroxamic acid (SAHA) proceeds through pathways that are regulated by Bcl-2/Bcl-XL, c-Jun, and p21CIP1, but independent of p53. Oncogene 18:7016-7025, 1999.
34. Adimoolam S, Sirisawad M, Chen J, Thiemann P, Ford J M, Buggy J J. HDAC inhibitor PCI-24781 decreases RAD51 expression and inhibits homologous recombination. Proc Natl Acad Sci USA 104:19482-19487, 2007.
35. Nome R V, Bratland A, Harman G, Fodstad O, Andersson Y, Ree A H. Cell cycle checkpoint signaling involved in histone deacetylase inhibition and radiation-induced cell death. Mol Cancer Ther 4:1231-1238, 2005
36. Kim G D, Choi Y H, Dimtchev A, Jeong S J, Dritschilo A, Jung M. Sensing of ionizing radiation-induced DNA damage by ATM through interaction with histone deacetylase. J Biol Chem 274:31127-31130, 1999.
37. Lagger G, O'Carroll D, Rembold M et al. Essential function of histone deacetylase 1 in proliferation control and CDK inhibitor repression. EMBO J 21:2672-2681, 2002.
38. Ju R, Muller M T. Histone deacetylase inhibitors activate p21 (WAF1) expression via ATM. Cancer Res 63: 2891-2897, 2003.
39. Geng L, Cuneo K C, Fu A, Tu T, Atadja P W, Hallahan D E. Histone deacetylase (HDAC) inhibitor LBH589 increases duration of gamma-H2AX foci and confines HDAC4 to the cytoplasm in irradiated non-small cell lung cancer. Cancer Res 66: 11298-304, 2006.
40. Stoilov L, Darroudi F, Meschini R, van der Schans G, Mullenders L H, Natarajan A T. Inhibition of repair of X-ray-induced DNA double-strand breaks in human lymphocytes exposed to sodium butyrate. Int J Radiat Biol 76:1485-1491, 2000.
41. Kim I A, Shin J H, Kim I H, Kim J H, Kim J S, Wu H G, Chie E K, Ha S W, Park C I, Kao G D. Histone deacetylase inhibitor-mediated radiosensitization of human cancer cells: class differences and the potential influence of p53. Clin Cancer Res 12: 940-949, 2006.
42. Munshi A, Kurland J F, Nishikawa T, Tanaka T, Hobbs M L, Tucker S L, Ismail S, Stevens C, Meyn R E. Histone deacetylase inhibitors radiosensitize human melanoma cells by suppressing DNA repair activity. Clin Cancer Res 11:4912-4922, 2005.
43. Shiloh Y. ATM and related protein kinases: safeguarding genome integrity. Nat Rev Cancer 3:155-68. Review, 2003.
44. Abraham R T, Tibbetts R S. Cell biology. Guiding ATM to broken DNA. Science 308:510-511, 2005.
45. Uziel T, Lerenthal Y, Moyal L, Andegeko Y, Mittelman L, Shiloh Y. requirement of the MRN complex for ATM activation by DNA damage. EMBO 22:5612-5621, 2003.
46. Tauchi H, Matsuura S, Kobayashi J, Sakamoto S, Komatsu K. Nijmegen breakage syndrome gene, NBS1, and molecular links to factors for genome stability. Oncogene 21:8967-80. Review, 2002.
47. Bakkenist C J, Kastan M B. DNA damage activates ATM through intermolecular autophosphorylation and dimer dissociation. Nature 421:499-506, 2003.
48. Kao G D, McKenna W G, Guenther M G, Muschel R J, Lazar M A, Yen T J. Histonedeacetylase 4 interacts with 53BP1 to mediate the DNA damage response. J Cell Bio 1160:1017-1027, 2003.
49. Geng L, Cuneo K C, Fu A, Tu T, Atadja P W, Hallahan D E. Histone deacetylase (HDAC) inhibitor LBH589 increases duration of gamma-H2AX foci and confines HDAC4 to the cytoplasm in irradiated non-small cell lung cancer. Cancer Res 66:11298-304, 2006.
50. Zhang Y, Jung M, Dritschilo A, Jung M. Enhancement of radiation sensitivity of human squamous carcinoma cells by histone deacetylase inhibitors. Radiat Res 161: 667-674, 2004.
51. Camphausen K, Scott T, Sproull M, Tofilon P J. Enhancement of xenograft tumor radiosensitivity by the histone deacetylase inhibitor MS-275 and correlation with histone hyperacetylation. Clin Cancer Res 10:6066-6071, 2004.
52. Kim J H, Shin J H, Kim I H. Susceptibility and radiosensitization of human glioblastoma cells to trichostatin A, a histone deacetylase inhibitor. Int J Radiat Oncol Biol Phys 59:1174-1180, 2004.
53. Adimoolan S, Sirisawad M, Chen J, Thiemann P, Ford J M, Buggy J J. HDAC inhibitor PC1-24781 decreases RAD51 expression and inhibits homologous recombination. Proc Natl Acad Sci USA 104: 19482-19487, 2007.
54. Chinnaiyan P, Vallabhaneni G, Armstrong E, Huang S M, Harari P M. Modulation of radiation response by histone deacetylase inhibition. Int J Radiat Oncol Biol Phys 62:223-229, 2005.
55. Karagiannis T C, Kn H, El-Osta A. The epigenetic modifier, valproic acid, enhances radiation sensitivity. Epigenetics 1:131-137, 2006.
56. Banuelos C A, Banath J P, MacPhail S H, Zhao J, Reitsema T, Olive P L. Radiosensitization by the histone deacetylase inhibitor PCI-24781. Clin Cancer Res 13:6816-6826, 2007.
57. Ashburner B P, Westerheide S D, Baldwin A S Jr. the p65 (RelA) subunit of NF-kappaB interacts with the histone deacetylase (HDAC) corepressors HDAC1 and HDAC2 to negatively regulate gene expression MCB 21:7065-7077, 2001.
58. Naryzhny S N, Lee H. The post-translational modifications of proliferating cell nuclear antigen: acetylation, not phosphorylation, plays an important role in the regulation of its function. JBC 279: 20,194-20,199, 2004.
59. Varshochi R, Halim F, Sunters A, Alao J P, Madureira P A, et al. ICI182,780 induces p21Waf1 gene transcription through releasing histone deaceytlase 1 and estrogen receptor alpha from SpI sites to induce cell cycle arrest in MCF-7 breast cancer cell line. J Biol Chem 280: 3185-96, 2005.
60. Blagosklonny M V, Robey R, Sackett D L, Du L, Traganos F, Darzynkiewicz Z, Fojo T, Bates S E Histone deacetylase inhibitors all induce p21 but differentially cause tubulin acetylation, mitotic arrest, and cytotoxicity. Mol Cancer Ther 1:937-941, 2002.
61. Jung M, Kozikowski A, Dritschilo A. Rational design and development of radiation-sensitizing histone deacetylase inhibitors. Chemistry and Biodiversity, 2:1452-1461, 2005.
62. Kozikowski A, Dritschilo A, Jung M, Petukov P A, Chen, B. Histone deacetylase isoform specific inhibitors and methods of use thereof. U.S. patent application Ser. No. 10/614,498.
63. Kozikowski A, Dritschilo A, Jung M, Bakin R E, Tueckmantel W, Gaysin A. Isoform selective HDAC inhibitors. U.S. Patent Application No. 60/835,259.
64. Brown M, Jung M, Dritschilo A, Kong Y. Histone deacetylase inhibitor. U.S. Patent Application No. 61,013, 866.
65. Kozikowski A, Jung M, Dritschilo A, Gaysin A, Petukov P A, Tueckmantel W, Yuan H. Isoform selective HDAC inhibitors. U.S. patent application Ser. No. 12/375,348.
66. Chen B, Petukhov P A, Jung M, Velena A, Eliseeva E, Dritschilo A, Kozikowski A P. Chemistry and biology of mercaptoacetamides as novel histone deacetylase inhibitors. Bioorg Med Chem Let 15:1389-1392, 2005.
67. Chinnaiyan P, Cerna D, Burgan W E, Beam K, Williams E S, Camphausen K, Tofilon P J. Postradiation sensitization of the histone deacetylase inhibitor valproicacid. Clin Cancer Res 14:5410-5415, 2008.
68. Karagiannis T C, El-Osta A. Modulation of cellular radiation responses by histone deacetylase inhibitors. Oncogene 25:3885-3893, Review, 2006.
69. Cerna D, Camphausen K, Tofilon P J. Histone deacetylation as a target for radiosensitization. Curr Top Dev Biol. 73:173-204, 2006.
70. Chinnaiyan P, Vallabhaneni G, Armstrong E, Huang S M, Harari P M. Modulation of radiation response by histone deacetylase inhibition. Int J Radiat Oncol Biol Phys 62(1):223-229, 2005.
71. Camphausen K, Tofilon P J. Inhibition of histone deacetylation: a strategy for tumor radiosensitization. Review. J Clin Oncol 25(26):4051-4056, 2007.
72. Chung Y L, Wang A J, Yao L F. Antitumor histone deacetylase inhibitors suppress cutaneous radiation syndrome: Implications for increasing therapeutic gain in cancer radiotherapy. Mol Cancer Ther 3:317-325, 2004.
73. Chang B K, Timmerman R D. Stereotatic body radiation therapy: a comprehensive review. Am J Clin Oncol 30:637-644, 2007.
74. Fakiris A J, McGarry R C, Yiannoutsos C T, Papiez L, Williams M, Henderson M A, Timmerman R. Stereotactic Body Radiation Therapy for Early-Stage Non-Small-Cell Lung Carcinoma: Four-Year Results of a Prospective Phase II Study. Int J Radiat Oncol Biol Phys, pp 1-6, 2009 [Epub ahead of print].

75. Barzilai A, Rotman G, Shiloh Y. ATM deficiency and oxidative stress: a new dimension of defective response to DNA damage. DNA Repair (Amst) 2002; 1:3-25. [PMID: 12509294]
76. Watters D J. Oxidative stress in ataxia telangiectasia. Redox Rep 2003; 8:23-29. Review. [PMID: 12631440]
77. Reliene R, Schiestl R H. Antioxidants suppress lymphoma and increase longevity in Atm-deficient mice. J Nutr 2007; 137 (1 Suppl):2295-232S. Review. [PMID: 17182831]
78. Guo Z, Kozlov S, Lavin M F, Person M D, Paull T T. ATM activation by oxidative stress. Science 2010; 330: 517-521. [PMID: 20966255]
79. Kruger A, Raiser M. ATM is a redox sensor linking genome stability and carbon metabolism. Sci Signal 2011; 4:pe17. [PMID: 21467295]
80. Fan S(1), Meng Q, Xu J, Jiao Y, Zhao L, Zhang X, Sarkar F H, Brown M L, DritschiloA, Rosen EM.DIM (3,3'-diindolylmethane) confers protection against ionizing radiation by aunique mechanism. Proc Natl Acad Sci USA. 2013 Nov. 12; 110 (46):18650-5. doi:10.1073/pnas.1308206110. Epub 2013 Oct. 14.
81. Yuan, H. Et al., Use of Reprogrammed Cells to Identify Therapy for Respiratory Papillomatosis, N. Engl. J. Med. 2012 Sep. 27; 367(13): 1220-7.

What is claimed is:

1. A compound of the formula:

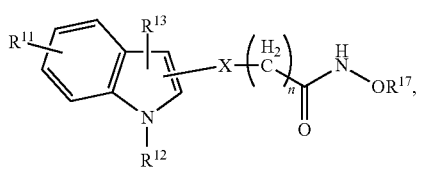

wherein $R^{11}$, $R^{13}$, $R^{14}$ and $R^{16}$ are independently selected from the group consisting of H, hydroxy, halogen, optionally substituted alkyl, optionally substituted alkenyl, optionally substituted alkynyl, optionally substituted cycloalkyl, optionally substituted aryl, optionally substituted heterocycle, optionally substituted heteroaryl, optionally substituted amino, optionally substituted alkoxy, optionally substituted carboxy, optionally substituted carbalkoxy, optionally substituted carboxamido, substituted sulfonyl, substituted sulfinyl, optionally substituted monoalkylaminosulfinyl, optionally substituted dialkylaminosulfinyl, optionally substituted monoalkylaminosufonyl, optionally substituted dialkylamninosulfonyl, optionally substituted alkyl sulfonylamino, optionally substituted hydroxysulfonyloxy, optionally substituted alkoxysulfonyloxy, optionally substituted alkylsulfonyloxy, optionally substituted hydroxysulfonyl, optionally substituted alkoxysulfonyl, optionally substituted alkylsulfonylalkyl, optionally substituted monoalkylaminosulfonylalkyl, optionally substituted dialkylaminosulfonylalkyl, optionally substituted monoalkylaminosulfinylalkyl, and optionally substituted dialkylaminosulfinylalkyl;

X is selected from the group consisting of:

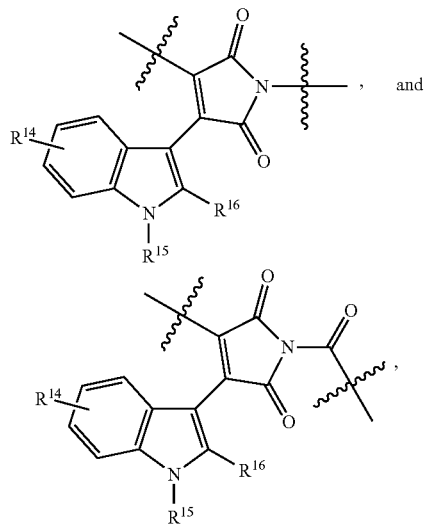

$R^{12}$ and $R^{15}$ may be independently selected from the group consisting of H, optionally-substituted alkyl, substituted sulfinyl, and substituted sulfonyl;

$R^{17}$ may be selected from the group consisting of H and optionally substituted alkyl;

n is an integer from 3 to 10; the dashed line indicates the presence of a single bond or a double bond as allowed; or the pharmaceutically acceptable salts thereof.

2. The compound of claim 1, wherein the compound is selected from the group consisting of:

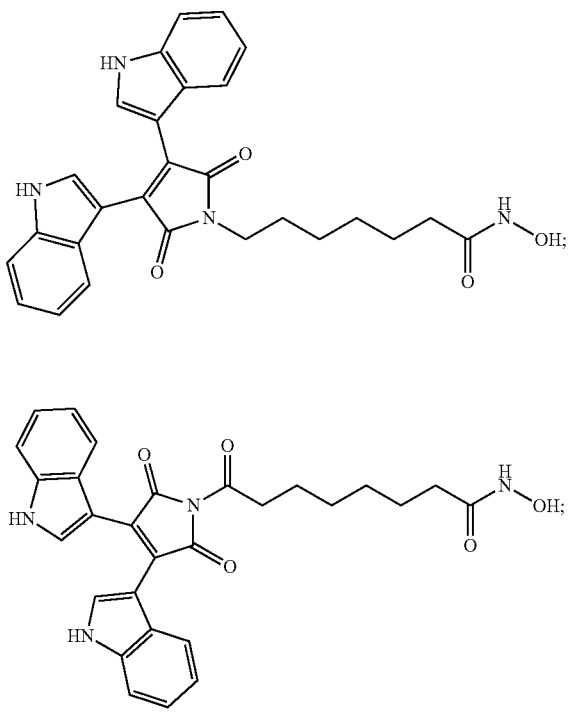

and the pharmaceutically acceptable salts thereof.

3. The compound of claim 1, wherein the compound is
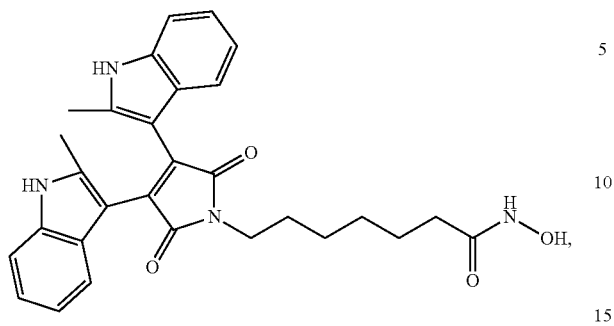
or a pharmaceutically acceptable salt thereof.
4. A pharmaceutical formulation comprising a compound of claim 1 in an amount effective to inhibit histone deacetylase (HDAC) and activate ataxia telangiectasia mutated (ATM) in a patient in need thereof and at least one physiologically compatible carrier medium.
* * * * *